US010088752B2

(12) United States Patent
Yamanaka et al.

(10) Patent No.: US 10,088,752 B2
(45) Date of Patent: Oct. 2, 2018

(54) METHOD FOR MANUFACTURING ORGANIC PROCESSING FLUID FOR PATTERNING OF CHEMICAL AMPLIFICATION TYPE RESIST FILM, ORGANIC PROCESSING FLUID FOR PATTERNING OF CHEMICAL AMPLIFICATION TYPE RESIST FILM, PATTERN FORMING METHOD, METHOD FOR MANUFACTURING ELECTRONIC DEVICE, AND ELECTRONIC DEVICE

(71) Applicant: FUJIFILM Corporation, Tokyo (JP)

(72) Inventors: Tsukasa Yamanaka, Shizuoka (JP); Takashi Kawamoto, Shizuoka (JP); Naoya Iguchi, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/872,726

(22) Filed: Oct. 1, 2015

(65) Prior Publication Data
US 2016/0026088 A1 Jan. 28, 2016

Related U.S. Application Data

(63) Continuation of application No. PCT/JP2014/058118, filed on Mar. 24, 2014.

(30) Foreign Application Priority Data

Apr. 2, 2013 (JP) .................................. 2013-076735

(51) Int. Cl.
C07C 45/78 (2006.01)
G03F 7/32 (2006.01)
G03F 7/038 (2006.01)
G03F 7/039 (2006.01)
C07C 29/76 (2006.01)
C07C 67/48 (2006.01)
C07C 67/56 (2006.01)

(52) U.S. Cl.
CPC ............... *G03F 7/32* (2013.01); *C07C 29/76* (2013.01); *C07C 45/786* (2013.01); *C07C 67/48* (2013.01); *C07C 67/56* (2013.01); *G03F 7/0382* (2013.01); *G03F 7/0397* (2013.01); *G03F 7/325* (2013.01)

(58) Field of Classification Search
CPC ......... G03F 7/32; G03F 7/325; C07C 45/786; C07C 67/56
USPC ....................................................... 430/322
See application file for complete search history.

(56) References Cited

U.S. PATENT DOCUMENTS 4,665,006 A * 5/1987 Sachdev et al. ........... 430/270.1
2002/0187439 A1 12/2002 Oberlander 2006/0014098 A1 * 1/2006 Hada et al. ................. 430/270.1
2006/0040203 A1 2/2006 Kodama et al.
2006/0194982 A1 8/2006 Harada et al.
2006/0264528 A1 11/2006 Wada
2008/0261150 A1 10/2008 Tsubaki et al.
2009/0045140 A1 * 2/2009 Zahka et al. ................... 210/718
2010/0190106 A1 7/2010 Tsubaki
2010/0323305 A1 12/2010 Tsubaki et al.
2012/0052449 A1 3/2012 Kato et al.

FOREIGN PATENT DOCUMENTS

| JP | 2000-5546 A | 1/2000 |
| JP | 2000267269 A | 9/2000 |
| JP | 2004-195427 A | 7/2004 |
| JP | 2004-533639 A | 11/2004 |
| JP | 2005-266766 A | 9/2005 |
| JP | 2006-257078 A | 9/2006 |
| JP | 2006-330098 A | 12/2006 |
| JP | 2007-325915 A | 12/2007 |
| JP | 2009-25708 A | 2/2009 |
| JP | 2010-39146 A | 2/2010 |
| JP | 2010-164958 A | 7/2010 |
| JP | 2011-138148 A | 7/2011 |
| JP | 2012-47896 A | 3/2012 |
| JP | 2013-218308 A | 10/2013 |
| JP | 2013218308 A | 10/2013 |

(Continued)

OTHER PUBLICATIONS

Office Action dated Aug. 9, 2016, by the Japanese Patent Office in counterpart Japanese Application No. 2015-224263.
Decision of Refusal dated Apr. 26, 2016, by the Japanese Patent Office in counterpart Japanese Application No. 2015-002259.
Communication dated Sep. 23, 2016 issued by the Korean Intellectual Property Office in counterpart Korean Patent Application No. 10-2015-7027078.
International Preliminary Report of Patentability and Written Opinion dated Oct. 15, 2015, issued by the International Searching Authority in counterpart International Application No. PCT/JP2014/058118 (PCT/IB/338, PCT/IB/373, & PCT/ISA/237).
Int. Search Report and Written Opinion dated Apr. 15, 2014 issued by the Int. Searching Authority in corresponding Application No. PCT/JP2014/058118 (PCT/ISA/210 & 237).

(Continued)

Primary Examiner — Daborah Chacko-Davis
(74) Attorney, Agent, or Firm — Sughrue Mion, PLLC

(57) ABSTRACT

There is disclosed a method for manufacturing an organic processing fluid for patterning of a chemical amplification type resist film, comprising a step of causing a fluid containing an organic solvent to pass through a filtration device having a fluid input portion, a fluid output portion, and a filtration filter film provided in a flow path that connects the fluid input portion and the fluid output portion with each other, wherein an absolute value ($|T_I - T_o|$) of a difference between a temperature ($T_I$) of the fluid in the fluid input portion and a temperature ($T_o$) of the fluid in the fluid output portion is 3° C. or lower, a filtration speed of the fluid in the filtration device is 0.5 L/min/m² or greater, and a filtration pressure by the fluid in the filtration device is 0.10 MPa or lower.

19 Claims, 1 Drawing Sheet

(56) References Cited

FOREIGN PATENT DOCUMENTS

KR    10-2012-0022662 A    3/2012
WO    2008/153110 A1    12/2008

OTHER PUBLICATIONS

Office Action dated Nov. 18, 2014 issued by the Japanese Patent Office in corresponding Application No. 2013-076735.
Office Action dated Sep. 15, 2015 issued by the Japanese Patent Office in corresponding Application No. 2015-002259.
Office Action dated Jun. 14, 2017 issued by the Taiwanese Patent Office in counterpart Taiwanese Patent Application No. 103112155.
Office Action dated Aug. 30, 2017, issued by the State Intellectual Property Office of the People's Republic of China in counterpart Chinese Patent Application No. 201510952485.9.
Office Action dated Apr. 3, 2018, issued by The State Intellectual Property Office of the People's Republic of China in counterpart Chinese application No. 201510952485.9.

* cited by examiner

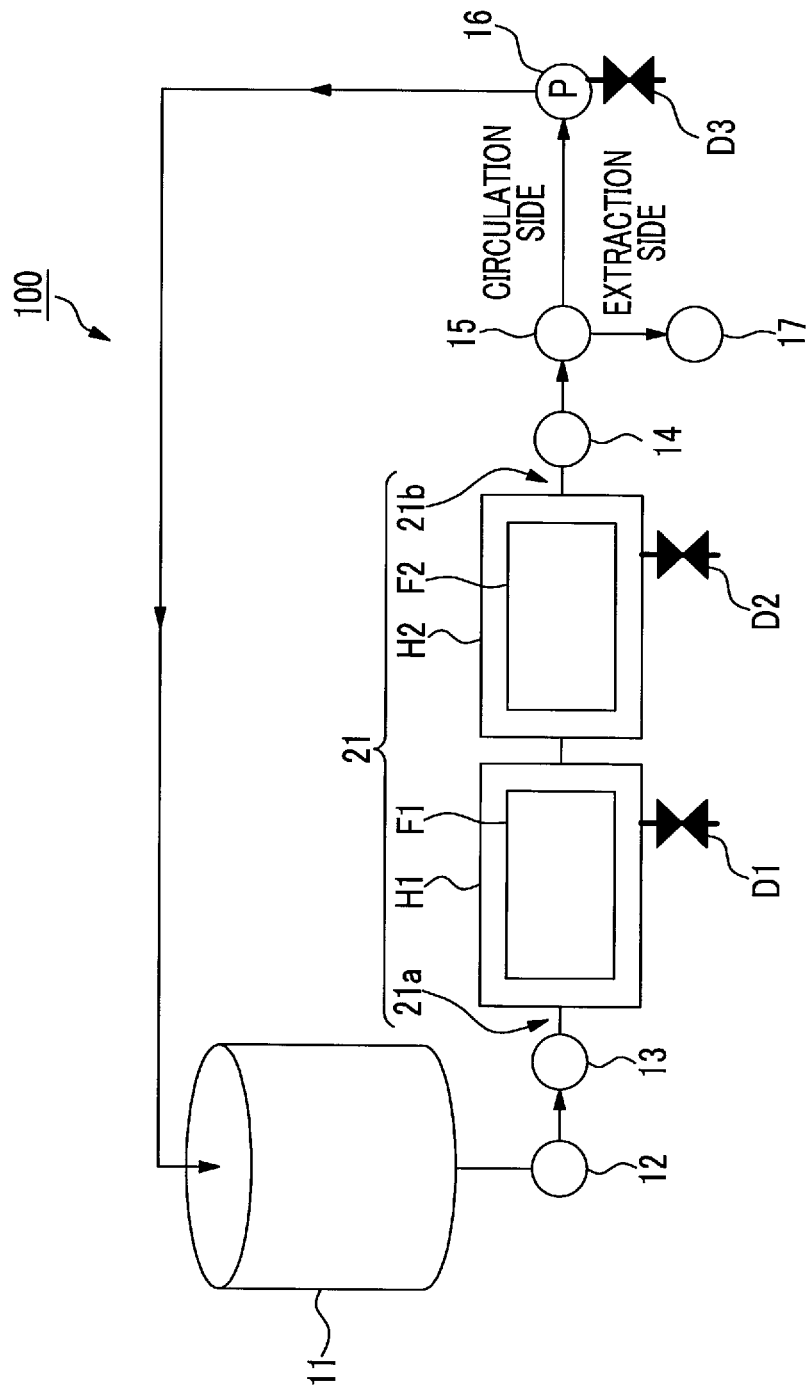

METHOD FOR MANUFACTURING ORGANIC PROCESSING FLUID FOR PATTERNING OF CHEMICAL AMPLIFICATION TYPE RESIST FILM, ORGANIC PROCESSING FLUID FOR PATTERNING OF CHEMICAL AMPLIFICATION TYPE RESIST FILM, PATTERN FORMING METHOD, METHOD FOR MANUFACTURING ELECTRONIC DEVICE, AND ELECTRONIC DEVICE

CROSS REFERENCE TO RELATED APPLICATION

This is a continuation of International Application No. PCT/JP2014/058118 filed on Mar. 24, 2014, and claims priority from Japanese Patent Application No. 2013-076735 filed on Apr. 2, 2013, the entire disclosures of which are incorporated therein by reference.

BACKGROUND OF THE INVENTION

1. Field of the Invention

The invention relates to a method for manufacturing an organic processing fluid for patterning of a chemical amplification type resist film, an organic processing fluid for patterning of a chemical amplification type resist film, a pattern forming method, a method for manufacturing an electronic device, and an electronic device. Specifically, the invention relates to a method for manufacturing an organic processing fluid for patterning of a chemical amplification type resist film, an organic processing fluid for patterning of a chemical amplification type resist film, a pattern forming method, a method for manufacturing an electronic device, and an electronic device, which are preferable for a semiconductor manufacturing step of IC or the like, manufacturing of a circuit substrate such as liquid crystal and a thermal head, and further, a lithography step of other photofabrication. Particularly, the invention relates to a method for manufacturing an organic processing fluid for patterning of a chemical amplification type resist film, an organic processing fluid for patterning of a chemical amplification type resist film, a pattern forming method, a method for manufacturing an electronic device, and an electronic device, which are preferable for exposure in an ArF exposing device and an ArF immersion type projection and exposure device, using a far ultraviolet ray having a wavelength of 300 nm or shorter, as a light source.

2. Description of the Related Art

In the related art, various configurations are suggested as a positive pattern forming method using an alkaline developer and a positive resist composition used therein (for example, refer to JP2006-257078A, JP2005-266766A, and JP2006-330098A). In addition to this, recently, a negative pattern forming method using an organic developer and a negative resist composition used therein of which a major use is to form a fine contact hole or a trench pattern that may not be achieved in a positive resist composition are developed (for example, refer to JP2007-325915A, WO2008-153110A, JP2010-039146A, JP2010-164958A).

The resist composition or the developer used in the positive or negative pattern forming method are generally used after fine particles in the resist composition or the developer are removed by a filter (for example, JP2000-005546A and JP2004-195427A).

SUMMARY OF THE INVENTION

However, recently, when the contact hole or the trench pattern is formed, the need for further refinement (for example, nodes of 30 nm or lower) has rapidly increased. Accordingly, the generation of the particles that easily has influence particularly on the performance of the fine pattern is required to be further suppressed.

The invention has been provided in view of the problems described above, and the object is to provide a method for manufacturing an organic processing fluid for patterning of a chemical amplification type resist film, an organic processing fluid for patterning of the chemical amplification type resist film using the same, a pattern forming method, a method for manufacturing an electronic device, and an electronic device, which can reduce the generation of particles in a technique for forming a negative pattern that forms a fine (for example, nodes of 30 nm or lower) pattern particularly by using an organic developer.

The inventors of the invention earnestly have reviewed so as to find that if a low molecular organic matter is eluted to an organic solvent from a filter by the contact between the organic solvent and the filter, though the amount is very small, and also the organic solvent is used as an organic developer in the negative pattern forming technique described above so as to form a fine pattern, the low molecular organic matter becomes a cause of the generation of particles that are not negligible on a fine pattern or a substrate. Also, the inventors have completed the invention by setting filtration conditions to be specific in the manufacturing of the organic processing fluid of an organic developer or an organic rinse fluid using a filtration device, such that fine particles in the organic processing fluid are removed by a filter, the low molecular organic matter is prevented from being eluted from the filter, and the generation of the particles that cause a problem in the forming of a fine pattern by the use of the organic processing fluid is reduced.

That is, the invention has the following configurations, and the object of the invention is achieved by the configurations.

[1]

A method for manufacturing an organic processing fluid for patterning of a chemical amplification type resist film including a step of causing a fluid containing an organic solvent to pass through a filtration device having a fluid input portion, a fluid output portion, and a filtration filter film provided in a flow path that connects the fluid input portion and the fluid output portion with each other, in which an absolute value ($|T_I - T_o|$) of a difference between a temperature ($T_I$) of the fluid in the fluid input portion and a temperature ($T_o$) of the fluid in the fluid output portion is 3° C. or lower, a filtration speed of the fluid in the filtration device is 0.5 L/min/m$^2$ or greater, and a filtration pressure by the fluid in the filtration device is 0.10 MPa or lower.

[2]

The method for manufacturing an organic processing fluid for patterning of a chemical amplification type resist film according to [1], in which the organic processing fluid is an organic developer.

[3]

The method for manufacturing an organic processing fluid for patterning of a chemical amplification type resist film according to [2], in which the fluid containing the organic solvent is butyl acetate.

[4]

The method for manufacturing an organic processing fluid for patterning of a chemical amplification type resist film according to [1], in which the organic processing fluid is an organic rinse fluid.

[5]

The method for manufacturing an organic processing fluid for patterning of a chemical amplification type resist film according to [4], in which the fluid containing the organic solvent is 4-methyl-2-pentanol or butyl acetate.

[6]

The method for manufacturing an organic processing fluid for patterning of a chemical amplification type resist film according to any one of [1] to [5], in which the filtration filter film is a polyethylene resin film, a fluorine resin film, or a polyamide resin film, of which a pore size is 50 nm or lower.

[7]

The method for manufacturing an organic processing fluid for patterning of a chemical amplification type resist film according to any one of [1] to [6], in which the temperature ($T_I$) of the fluid in the fluid input portion is in a range of 20° C. to 30° C.

[8]

An organic processing fluid for patterning of a chemical amplification type resist film, which is manufactured by the method for manufacturing an organic processing fluid for patterning of a chemical amplification type resist film according to any one of [1] to [7].

[9]

A pattern forming method, including: (A) a step of forming a film with a chemical amplification type resist composition; (B) a step of exposing the film; and (C) a step of developing the exposed film by using an organic developer, in which the organic developer is an organic developer manufactured by the method for manufacturing an organic processing fluid for patterning of a chemical amplification type resist film according to [2] or [3].

[10]

The pattern forming method according to [9], further including: a step of washing the exposed film by using an organic rinse fluid after the step of developing the exposed film by using the organic developer, in which the organic rinse fluid is an organic rinse fluid manufactured by the method for manufacturing an organic processing fluid for patterning of a chemical amplification type resist film according to [4] or [5].

[11]

The pattern forming method according to [10], in which the organic developer is an organic developer manufactured by the method for manufacturing an organic processing fluid for patterning of a chemical amplification type resist film according to [3], and the organic rinse fluid is an organic rinse fluid manufactured by the method for manufacturing an organic processing fluid for patterning of a chemical amplification type resist film according to [5].

[12]

The pattern forming method according to any one of [9] to [11], in which the step of developing the film by using the organic developer is a step of developing a film by using a developing device with a filter for the processing fluid, and the organic developer is used for development by being passed through the filter for the processing fluid.

[13]

A method for manufacturing an electronic device, including: the pattern forming method according to any one of [9] to [12].

[14]

An electronic device manufactured by the method for manufacturing an electronic device according to [13].

According to the invention, it is possible to provide a method for manufacturing an organic processing fluid for patterning of a chemical amplification type resist film, an organic processing fluid for patterning of the chemical amplification type resist film using the same, a pattern forming method, a method for manufacturing an electronic device, and an electronic device, which can reduce the generation of particles in a technique for forming a negative pattern that forms a fine (for example, nodes of 30 nm or lower) pattern particularly by using an organic developer.

BRIEF DESCRIPTION OF THE DRAWING

FIGURE is a diagram schematically illustrating a method for manufacturing an organic processing fluid for patterning a chemical amplification type resist film according to an embodiment of the invention.

DESCRIPTION OF THE PREFERRED EMBODIMENTS

Hereinafter, the embodiments of the invention are described in detail.

In the specification, with respect to an expression of a group (atomic group) in this specification, expressions without "substituted" or "unsubstituted" include a group not having a substituent or a group having a substituent. For example, an expression "alkyl group" includes an alkyl group not having a substituent (unsubstituted alkyl group) and an alkyl group having a substituent (substituted alkyl group).

An "active ray" or a "radiant ray" in the specification means, for example, a bright line spectrum of a mercury lamp, or a far ultraviolet ray, an extreme ultraviolet ray (EUV ray), an X ray, or an electron ray (EB) represented by an excimer laser. In addition, according to the invention, light refers to an active ray or a radiant ray.

In addition, with respect to the "exposure" in this specification, unless described otherwise, in addition to exposure by a mercury lamp or a far ultraviolet ray, an extreme ultraviolet ray, an X ray, and a EUV ray represented by an excimer laser, drawing by a particle ray such as an electron ray, an ion beam, or the like is included in the exposure.

FIGURE is a diagram schematically illustrating a method for manufacturing an organic processing fluid for patterning of a chemical amplification type resist film according to an embodiment of the invention.

As schematically illustrated in the drawing of FIGURE, an organic processing fluid manufacturing system 100 includes a fluid tank 11 that can store a fluid containing an organic solvent, a fluid amount adjusting valve 12, a pressure/flow rate/fluid temperature meter 13, a filtration device 21, a flow rate/fluid temperature meter 14, a flow switching valve 15, and a pump 16. Also, the organic processing fluid manufacturing system 100 is configured so that the fluid can circulate in a sequence of the fluid tank 11, the fluid amount adjusting valve 12, the pressure/flow rate/fluid temperature meter 13, the filtration device 21, the flow rate/fluid temperature meter 14, the flow switching valve 15, the pump 16, the fluid tank 11, and the like.

The fluid tank 11 can store a "fluid containing the organic solvent" (hereinafter, referred to as an "organic fluid to be filtrated") provided for the filtration, and is generally accompanied with a temperature regulator that can adjust a temperature of the organic fluid to be filtrated.

As the fluid tank 11, a well-known product may be employed. A preferable material of the fluid tank 11 is described below in detail, together with the preferable materials of the other members constituting the organic processing fluid manufacturing system 100.

The organic fluid to be filtrated is a fluid that becomes an organic processing fluid for patterning of a chemical amplification type resist film by being filtrated by the filtration device 21 of the organic processing fluid manufacturing system 100, and preferably a fluid that becomes an organic developer or an organic rinse fluid of a chemical amplification type resist film.

The organic processing fluid for patterning of the chemical amplification type resist film is typically an "organic developer" in a pattern forming method including (A) a step of forming a film by a chemical amplification type resist composition; (B) a step of exposing the film; and (C) a step of developing the exposed film by using an organic developer, or an "organic rinse fluid" in a step of washing the film by using an organic rinse fluid, which may be performed in the pattern forming method after the step (C).

The organic developer means a developer containing an organic solvent.

The organic fluid to be filtrated for manufacturing the organic developer to be filtrated (or the organic developer) may contain one or more kinds of organic solvents.

The used amount of the organic solvent of the organic fluid to be filtrated for manufacturing the organic developer (or the organic developer) is preferably 90% by mass to 100% by mass, and more preferably 95% by mass to 100% by mass with respect to the total amount of the organic fluid to be filtrated (or the organic developer).

As the organic fluid to be filtrated for manufacturing the organic developer (or the organic developer), a polar solvent such as a ketone-based solvent, an ester-based solvent, an alcohol-based solvent, an amide-based solvent, or an ether-based solvent or a hydrocarbon-based solvent can be used.

As the ketone-based solvent, for example, 1-octanone, 2-octanone, 1-nonanone, 2-nonanone, acetone, 2-heptanone (methyl amyl ketone), 4-heptanone, 1-hexanone, 2-hexanone, diisobutyl ketone, cyclohexanone, methyl cyclohexanone, phenyl acetone, methyl ethyl ketone, methyl isobutyl ketone, acetylacetone, acetonylacetone, ionone, diacetonyl alcohol, acetyl carbinol, acetophenone, methyl naphthyl ketone, isophorone, and propylene carbonate are included.

As the ester-based solvent, for example, methyl acetate, butyl acetate, ethyl acetate, isopropyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxybutyl acetate, 3-methyl-3-methoxybutyl acetate, methyl formate, ethyl formate, butyl formate, propyl formate, ethyl lactate, butyl lactate, and propyl lactate are included.

As the alcohol-based solvent, for example, an alcohol such as methyl alcohol, ethyl alcohol, n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol, n-decanol, and 4-methyl-2-pentanol, a glycol-based solvent such as ethylene glycol, diethylene glycol, and triethylene glycol, and a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxy methyl butanol are included.

As the ether-based solvent, for example, in addition to the glycol ether-based solvent, dioxane and tetrahydrofuran are included.

As the amide-based solvent, for example, N-methyl-2-pyrrolidone, N,N-dimethylacetamide, N,N-dimethylformamide, hexamethylphosphoric triamide, and 1,3-dimethyl-2-imidazolidinone are included.

As the hydrocarbon-based solvent, for example, an aromatic hydrocarbon-based solvent such as toluene and xylene, an aliphatic hydrocarbon-based solvent such as pentane, hexane, octane, and decane are included.

Plural kinds of the solvents may be mixed, or the solvent may be mixed with a solvent other than the solvents described above or water to be used. However, in order to sufficiently achieve the effect of the invention, the water content of the entire organic fluid to be filtrated for manufacturing the organic developer (or the organic developer) is preferably less than 10% by mass, and it is more preferable that water is not substantially contained.

Particularly, the organic fluid to be filtrated for manufacturing the organic developer (or organic developer) preferably contains at least one kind of the organic solvent selected from the group consisting of a ketone-based solvent, an ester-based solvent, an alcohol-based solvent, an amide-based solvent, and an ether-based solvent.

The steam pressure of the organic fluid to be filtrated for manufacturing the organic developer (or the organic developer) is preferably 5 kPa or lower, more preferably 3 kPa or lower, and particularly preferably 2 kPa or lower at 20° C. If the steam pressure is 5 kPa or lower, the evaporation of the developer on the substrate or in a development cup is suppressed, and thus the temperature uniformity in the wafer surface increases, and as a result, the dimension uniformity in the wafer surface improves.

In the organic fluid to be filtrated for manufacturing the organic developer (or the organic developer), if necessary, the surfactant can be added in an appropriate amount.

The surfactant is not particularly limited, but, for example, ionic or nonionic and fluorine-based and/or silicon-based surfactant can be used. As the fluorine-based and/or silicon-based surfactant, for example, surfactants disclosed in, for example, JP-S62-36663A, JP-S61-226746A, JP-S61-226745A, JP-S62-170950A, JP-S63-34540A, JP-H7-230165A, JP-H8-62834A, JP-H9-54432A, JP-H9-5988A, U.S. Pat. No. 5,405,720A, U.S. Pat. No. 5,360,692A, U.S. Pat. No. 5,529,881A, U.S. Pat. No. 5,296,330A, U.S. Pat. No. 5,436,098A, U.S. Pat. No. 5,576,143A, U.S. Pat. No. 5,294,511A, and U.S. Pat. No. 5,824,451A can be included, and a nonionic surfactant is preferable. The nonionic surfactant is not particularly limited, but a fluorine-based surfactant or a silicon-based surfactant is more preferably used.

The used amount of the surfactant is generally in the range of 0.001% by mass to 5% by mass, preferably in the range of 0.005% by mass to 2% by mass, and more preferably in the range of 0.01% by mass to 0.5% by mass with respect to the total amount of the organic fluid to be filtrated for manufacturing the organic developer (or the organic developer).

The organic fluid to be filtrated for manufacturing the organic developer (or the organic developer) is preferably butyl acetate or 2-heptanone (methyl amyl ketone), and is more preferably butyl acetate.

In addition, the organic fluid to be filtrated for manufacturing the organic developer or the organic developer may include a nitrogen-containing compound exemplified in paragraphs 0041 to 0063 of JP5056974B. In addition, in view of the storage stability or the like of the organic fluid to be filtrated for manufacturing the organic developer or the organic developer, the nitrogen-containing compound is preferably added to the organic fluid to be filtrated for manufacturing the organic developer or the organic developer right before the pattern forming method is performed.

In addition, the organic rinse fluid means a rinse fluid that contains the organic solvent.

The organic fluid to be filtrated for manufacturing the organic rinse fluid (or the organic rinse fluid) may contain one or more kinds of the organic solvents.

The used amount of the organic solvent in the organic fluid to be filtrated for manufacturing the organic rinse fluid (or the organic rinse fluid) is preferably 90% by mass to 100% by mass and more preferably 95% by mass to 100% by mass with respect to the total amount of the organic fluid to be filtrated (or the organic rinse fluid).

The organic fluid to be filtrated (or the organic rinse fluid) is not particularly limited, as long as the organic fluid does not dissolve a resist pattern, and a solution containing a general organic solvent can be used. The rinse fluid preferably contains at least one kind of organic solvent selected from the group consisting of a hydrocarbon-based solvent, a ketone-based solvent, an ester-based solvent, an alcohol-based solvent, an amide-based solvent, and an ether-based solvent.

As specific examples of the hydrocarbon-based solvent, the ketone-based solvent, the ester-based solvent, the alcohol-based solvent, the amide-based solvent, and the ether-based solvent, the same products as those described for the organic fluid to be filtrated for manufacturing the organic developer can be included.

Among them, the organic fluid to be filtrated (or the organic rinse fluid) preferably contains the alcohol-based solvent or the ester-based solvent, more preferably contains a univalent alcohol, and still more preferably contains a univalent alcohol having 5 or more carbon atoms.

As the univalent alcohol, a linear, branched, or cyclic univalent alcohol is included, specifically, 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, 4-octanol, or the like can be used, and as the univalent alcohol having 5 or more carbon atoms which is particularly preferable, 1-hexanol, 2-hexanol, 4-methyl-2-pentanol, 1-pentanol, 3-methyl-1-butanol, or the like can be used.

As the organic rinse fluid, 4-methyl-2-pentanol or butyl acetate is preferable.

The water content in the organic fluid to be filtrated (or the organic rinse fluid) is preferably 10% by mass or lower, more preferably 5% by mass or lower, and particularly preferably 3% by mass or lower. If the water content is 10% by mass or lower, favorable developing characteristics can be obtained.

The steam pressure of the organic fluid to be filtrated (or the organic rinse fluid) is preferably in the range of 0.05 kPa to 5 kPa, more preferably in the range of 0.1 kPa to 5 kPa, and most preferably in the range of 0.12 kPa to 3 kPa at 20° C. If the steam pressure is in the range of 0.05 kPa to 5 kPa, the temperature uniformity in the wafer surface improves, the swelling caused by the penetration of the rinse fluid is suppressed, and the dimension uniformity in the wafer surface is improved.

The surfactants described above may be added in an appropriate amount to the organic fluid to be filtrated (or the organic rinse fluid), to be used.

The fluid configuring the organic fluid to be filtrated is preferably a distilled fluid. Accordingly, the organic processing fluid with higher purity which is appropriate for the use of patterning the chemical amplification type resist film can be manufactured.

The distillation may be performed once, or may be performed two or more times. As the distillation method, well-known methods can be appropriately applied. For example, the distillation may be performed according to the methods disclosed in JP2006-305573A, JP-S62-161736A, and JP-S58-211000A, but the method is not limited thereto.

The fluid amount adjusting valve 12 controls the flow rate of the organic fluid to be filtrated, and well-known valves may be employed.

As described below, the filtration speed and the filtration pressure of the organic fluid to be filtrated can be adjusted by causing the fluid amount adjusting valve 12 to control the flow rate of the organic fluid to be filtrated.

The filtration device 21 includes a fluid input portion 21a, a first stage filter F1 connected to the fluid input portion 21a, a second stage filter F2 connected to the first stage filter F1, and a fluid output portion 21b connected to the second stage filter F2.

Here, the fluid input portion 21a is connected to the fluid amount adjusting valve 12 side, and the fluid output portion 21b is connected to the flow switching valve 15 side.

In addition, the first stage filter F1 and the second stage filter F2 are stored inside of a first filter housing H1 and a second filter housing H2, respectively.

Also, drains D1 and D2 for performing an air bleeding operation inside the filters and filter housings which is required at the time of exchanging the filter F1 and the filter F2 or for discharging a fluid from a circulation line of the organic processing fluid manufacturing system 100 are provided in the first filter housing H1 and the second filter housing H2, respectively.

As described above, a two-stage filtration method in which two filters F1 and F2 are used in series in the organic processing fluid manufacturing system 100 is employed.

The shapes of the filters F1 and F2 are not particularly limited, and are generally a disk type or a cartridge type.

The filters F1 and F2 each are configured with a media support, a core or a cage that constitute a filter shape, an end cap, and an O ring in addition to filtration filter films (filter media) (not illustrated).

Accordingly, the filtration filter films in the filters F1 and F2 are provided in the flow path that connects the fluid input portion 21a and the fluid output portion 21b.

The members that constitute the filter are preferably made of a fluorine resin such as polytetrafluoroethylene (PTFE), a polyolefin resin such as polyethylene (PE) and polypropylene (PP), and a polyamide resin such as Nylon 6 and Nylon 66, preferably made of a fluorine resin, a high density polyethylene, polypropylene, or a polyamide resin, and particularly preferably made of fluorine resin.

However, the fluorine resin has high hydrophobicity, and may have a restriction to a solvent that can be filtrated (for example, solvent having high polarity). In this case, if the filter is configured with a fluorine resin of which the surface can be hydrophilized, the fluid having high polarity can be easily filtrated.

The pore sizes of the filtration filter films in the filters F1 and F2 each are preferably 200 nm or lower, more preferably 50 nm or lower, and still more preferably 20 nm or lower.

Here, if the pore size is 200 nm or lower, the fine particles in the fluid containing the organic solvent can be sufficiently removed by a filtration filter film.

The pore sizes of the filtration filter film in the filters F1 and F2 are preferably as small as possible, but generally are 5 nm or greater.

The filtration filter films in the filters F1 and F2 are preferably made of a polyethylene resin film, a fluorine resin film, or a polyamide resin film which have a pore size of 50 nm or lower.

In addition, in the present specification, the pore size of the filtration filter film means an average pore diameter of the filter, and a nominal hole diameter value of a manufacturer.

Since the filtration pressure has influence on the filtration precision, it is preferable that the pulsation of the pressure at the time of filtration is as small as possible.

In addition, particularly when the amount of the fine particles contained in the organic fluid to be filtrated is great, if the particles are removed sequentially from the largest, the clogging of the filter can be prevented, such that the manufacturing productivity of the organic processing fluid can be improved.

From this point of view, it is preferable that the multi-stage filtration method in which plural filers are connected in series, and the pore size of the filtration filter film is caused to be larger as the filtration is closer to the first stage filtration is employed as the filtration method.

That is, in the filtration device 21, the pore size of the filtration filter film in the first stage filter F1 that performs the first stage filtration is preferably larger than the pore size of the filtration filter film in the second stage filter F2 that performs the second stage filtration.

In addition, as a method of removing a foreign substance such as fine particles from the fluid with the filtration filter film, in addition to a method of using the sieving effect by causing the pore size of the filtration filter film to be smaller than the size of the foreign substance, a method of causing foreign substances to be adsorbed on the surface of the filtration filter film is known, and a filtration filter film that can adsorb and remove the low molecular organic matter (for example, low molecular olefin compound) considered as a target object to be removed according to the invention is also preferable.

As cartridge filters that are commercially available and can be used as the filters F1 and F2, for example, Microgard Plus and Fluorogard AT/ATX manufactured by Nihon Entegris K.K., and PE-Kleen, Emflon PF, UltiKleen Excellar, and Ultipleat P-Nylon manufactured by Pall Corporation are included.

The pressure/flow rate/fluid temperature meter 13 is a measuring apparatus that measures the pressure, the flow rate, and the temperature of the fluid in the fluid input portion 21a of the filtration device 21, and any well-known products can be employed.

The flow rate/fluid temperature meter 14 is a measuring apparatus that measures the temperature of the fluid in the fluid output portion 21b of the filtration device 21, and any well-known products can be employed. The pressure/flow rate/fluid temperature meter 13 and the flow rate/fluid temperature meter 14 are mainly meters for checking the absolute value ($|T_I-T_o|$) of the difference between the temperature ($T_I$) of the fluid in the fluid input portion 21a and the temperature ($T_o$) of the fluid in the fluid output portion 21b, the filtration speed of the fluid in the filtration device 21, and the filtration pressure by the fluid in the filtration device 21, which are described below, and the pressure/flow rate/fluid temperature meter 13 and the flow rate/fluid temperature meter 14 are not necessary for the manufacturing of the organic processing fluid. Therefore, in cases other than the time for checking the manufacturing conditions, the pressure/flow rate/fluid temperature meter 13 and the flow rate/fluid temperature meter 14 can be omitted.

The flow switching valve 15 is a valve for switching the flow of the fluid from the filtration device 21 to the pump 16 side (circulation side) and a fluid extraction opening 17 side (extraction side), and any well-known products can be employed.

The pump 16 is a pump for transferring the fluid from the flow switching valve 15 to the fluid tank 11, and a drain D3 for discharging the fluid from the circulation line of the organic processing fluid manufacturing system 100 is provided. As the pump 16, any well-known products can be employed, but in view of minimizing the carrying of contamination from the inside of the organic processing fluid manufacturing system 100 to the fluid, a pump which has little bubble generation and pulsation is particularly preferable.

In the organic processing fluid manufacturing system 100, raw materials that constitute inner walls which come into contact with the fluid of the fluid tank 11 and surfaces of flow paths (pipes, seal portion, joint member, and the like) which come into contact with the fluid, other than the filtration device 21 described above, are preferably resins different from "one or more kinds of resins selected from the group consisting of a polyethylene resin, a polypropylene resin, and a polyethylene-polypropylene resin", or metals subjected to rust preventing and metal elution preventing treatments.

In addition, with respect to the fluid tank 11, if the fluid tank 11 further includes a seal portion that seals the organic fluid to be filtrated, the seal portion is also preferably formed of resins different from "one or more kinds of resins selected from the group consisting of a polyethylene resin, a polypropylene resin, and a polyethylene-polypropylene resin", or metals subjected to rust preventing and metal elution preventing treatments.

Here, the seal portion means a member that can insulate the outside air, and a packing, an O ring, or the like are preferably included.

The resins different from one or more kinds of resins selected from the group consisting of a polyethylene resin, a polypropylene resin, and a polyethylene-polypropylene resin is preferably a perfluoro resin.

The perfluoro resin includes a tetrafluoroethylene resin (PTFE), a tetrafluoroethylene-perfluoroalkyl vinyl ether copolymer (PFA), a tetrafluoroethylene-hexafluoropropylene copolymer resin (FEP), a tetrafluoroethylene-ethylene copolymer resin (ETFE), a trifluorochloroethylene-ethylene copolymer resin (ECTFE), a vinylidene fluoride resin (PVDF), a trifluorochloroethylene copolymer resin (PCTFE), and a vinyl fluoride resin (PVF).

As a particularly preferable perfluoro resin, a tetrafluoroethylene resin, a tetrafluoroethylene-perfluoroalkyl vinyl ether copolymer, and a tetrafluoroethylene-hexafluoropropylene copolymer resin are included.

As metal for the metals subjected to rust preventing and metal elution preventing treatments, carbon steel, alloy steel, nickel-chrome steel, nickel-chrome-molybdenum steel, chrome steel, chrome-molybdenum steel, manganese steel, and the like are included.

As the rust preventing and metal elution preventing treatments, a coating technique is preferably applied.

The coating technique is broadly classified into three kinds of metal coating (various kinds of plating), inorganic coating (various chemical conversion coating, glass, concrete, ceramics, and the like), and organic coating (rust preventing oil, paint, rubber, and plastics).

As a preferable coating technique, surface treatments with rust preventing oil, a rust preventing agent, a corrosion inhibitor, a chelate compound, strippable plastic, and a lining agent are included.

Among them, carboxylic acids such as various kinds of chromate, nitrite, silicate, phosphate, oleic acid, dimer acid, and naphthenic acid, corrosion inhibitors such as carboxylic acid metal soaps, sulfonate, amine salt, and ester (glycerol ester and phosphoric acid ester of higher fatty acids), chelate compounds such as ethylenediaminetetraacetic acid, gluconic acid, nitrilotriacetic acid, hydroxyethyl ethylene diamine triacetic acid, and diethylenetriamine pentaacetic acid, and fluorine resin lining are preferable. Phosphate treatment and fluorine resin lining are particularly preferable.

In addition, compared with a direct coating treatment, though rust is not directly prevented, the "pre-treatment" which is a step before the rust preventing treatment is performed is preferably employed as a treatment method for extending the rust prevention period by a coating treatment.

As a specific example of the pre-treatment, treatments for removing various corrosion factors such as chloride or sulfate which exist on metal surfaces by washing or polishing are preferably included.

In the organic processing fluid manufacturing system 100, the organic processing fluid for patterning of the chemical amplification type resist film is manufactured by driving the pump 16 such that the fluid circulate inside of the system, and the organic fluid to be filtrated which is stored in the fluid tank 11 passes through the filtration device 21.

The manufactured organic processing fluid is extracted from the fluid extraction opening 17 by switching the flow switching valve 15 to the fluid extraction opening 17 side.

In view of improving uniformity of the filtration precision, if the pump is driven for a certain period of time or longer, the fluid may be caused to circulate in the system for a certain period of time or longer. In addition, the fluid coming out from the extraction opening 17 is periodically examined, after particle examination results become stable, the pump is stopped, and the filtrated fluid may be extracted from the extraction opening 17.

Generally, the organic fluid to be filtrated has small specific heat and high volatility. Therefore, in a portion in which a fluid temperature is not sufficiently controlled (particularly, at the time of passing through the filter), the fluid temperature changes. In addition, if the organic fluid to be filtrated is a solvent having high viscosity, the filtration time becomes long, and thus the fluid temperature change influences more.

The inventors of the invention have found that the suppression of the temperature change contributes to the reduction of the generation of the particles in a technique for forming a negative pattern that forms a fine (for example, nodes of 30 nm or lower) pattern particularly by using an organic developer.

That is, in the method for manufacturing the organic processing fluid for patterning of the chemical amplification type resist film according to the invention, first, the absolute value ($|T_I-T_o|$) of the difference between the temperature ($T_I$) of the fluid in the fluid input portion 21a of the filtration device 21 and the temperature ($T_o$) of the fluid in the fluid output portion 21b of the filtration device 21 is 3° C. or lower.

If the absolute value $|T_I-T_o|$ is greater than 3° C., it becomes difficult to reduce the generation of the particles that cause a problem in the technique for forming the negative pattern that forms the fine pattern by using an organic developer.

As described above, the filter is formed of various components such as a filtration filter film (filter media), a media support, a core or a cage that constitute a filter shape, an end cap, and an O ring. Because of the limitation of the use of manufacturing a semiconductor which detests metal contamination, the filter configuration member is basically a resin. Generally, various additives are added to a resin in order to secure durability of the resin. In addition, in a resin synthesization method which is widely used in general (radical method and thermal polymerization method), a lot of polymers having a lower molecular weight than an objective resin molecular weight are included. These additives or low molecular polymers are soluble in the organic processing fluid, and become contamination of the processing fluid. Particularly, it is considered that this contamination is not negligible in the organic processing fluid used in the technique for forming the negative pattern that forms the fine (for example, nodes of 30 nm or lower) pattern by using the organic developer. It is assumed that, since this contamination is caused by the solubility of a material, if the fluid temperature management (specifically, temperature management such that the absolute value $|T_I-T_o|$ is 3° C. or lower) during the filtration is performed in order to control the contamination to be minimized or to be constant, the generation of the particles is reduced.

The absolute value $|T_I-T_o|$ is preferably 2° C. or lower, more preferably 1° C. or lower, still more preferably 0.5° C. or lower, and particularly preferably 0° C.

In addition, the temperature of the fluid has influence on the viscosity of the fluid to be filtrated and the mixed amount of impurities from equipment that constitutes the manufacturing system to the organic processing fluid.

If the temperature of the fluid is low, the viscosity of the fluid to be filtrated becomes too high, and the filtration flow rate decreases, such that the filtration pressure increases. Therefore, the compatibility between the filtration precision and the productivity tends to be difficult.

Meanwhile, the solubility of the material in the fluid is generally small when the temperature of the fluid is low, and thus it is preferable that the temperature of the fluid supplied for the filtration is low to a certain degree, since the mixed amount of the impurities from the equipment that constitutes the manufacturing system to the organic processing fluid decreases.

Accordingly, in order to satisfy the filtration precision, the mixed amount of the contamination from the manufacturing process equipment to the organic treatment, and the productivity, in addition to the absolute value $|T_I-T_o|$, it is preferable to manage the temperature of the fluid during the filtration.

Specifically, the temperature of the fluid before the filter passage, that is, the temperature ($T_I$) of the fluid in the fluid input portion 21a of the filtration device 21 is preferably in the range of 15° C. to 35° C., more preferably in the range of 20° C. to 30° C., and most preferably 20° C. to 25° C.

As the method of adjusting the absolute value $|T_I-T_o|$ and the temperature $T_I$, for example, a method of adjusting temperatures in the respective positions by mounting heat insulation equipment (well-known equipment such as heater or water jacket) on at least one of the tank 11, the fluid input portion 21a of the filtration device 21, the first filter housing H1, the second filter housing H2, and the fluid output portion 21b, and a method of installing the organic processing fluid manufacturing system 100 in a clean room in which a temperature is managed are preferably included.

In addition, the filtration speed has influence on filtration precision, the mixed amount of the impurities from the filter to the organic processing fluid, and the productivity.

Generally, low filtration speed is preferable in that filtration precision is enhanced, but may cause increase of the mixed amount of the impurities from the filter to the organic processing fluid and decrease of the productivity.

The inventors of the invention earnestly have reviewed to find out that, as described above, as the absolute value ($|T_f-T_o|$) of the difference between the temperature ($T_f$) of the fluid in the fluid input portion 21a of the filtration device 21 and the temperature ($T_o$) of the fluid in the fluid output portion 21h of the filtration device 21 is 3° C. or lower, the filtration pressure is a low value, and the filtration speed is a certain value or higher, and thus the generation of the particles can be reduced (in addition, productivity is satisfied) in the technique for forming the negative pattern that forms the fine (for example, nodes of 30 nm or lower) pattern particularly by using the organic developer.

That is, in the method for manufacturing the organic processing fluid for patterning of the chemical amplification type resist film according to the invention, the filtration speed of the fluid in the filtration device 21 is 0.5 L/min/m² or higher, and the filtration pressure by the fluid in the filtration device 21 is 0.10 MPa or lower.

Meanwhile, if the filtration speed is less than 0.5 L/min/m², or the filtration pressure is greater than 0.10 MPa, it becomes difficult to reduce the generation of the particles that may cause a problem in the technique for forming the negative pattern that forms the fine pattern by using the organic developer.

The filtration speed is preferably 0.6 L/min/m² or higher, more preferably 0.75 L/min/m² or higher, and still more preferably 1.0 L/min/m² or higher.

In the filter, differential pressure resistance that secures filter performance (filter is not broken) is set. Therefore if the value is high, the filtration speed can be increased by increasing the filtration pressure. That is, the upper limit of the filtration speed generally depends on the differential pressure resistance of the filter, but is preferably 10.0 L/min/m² or lower, in general.

The filtration pressure is preferably in the range of 0.01 MPa to 0.10 MPa, more preferably in the range of 0.03 MPa to 0.08 MPa, and particularly preferably in the range of 0.03 MPa to 0.06 MPa.

In addition, if the pore size of the filtration filter film becomes small, the filtration speed decreases, but, for example, if plural filters to which the same kind of the filtration filter films are mounted are connected in parallel, the filtration area is enlarged and the filtration pressure decreases. Accordingly, the decrease of the filtration speed can be compensated for.

The filtration speed of the fluid in the filtration device can be obtained by using the filtration flow rate of the fluid flowing through the filtration device.

The filtration speed of the fluid in the filtration device can be defined as expressed by an equation described below.

Filtration speed (L/min/m²) of fluid in filtration device=filtration flow rate of fluid flowing though filtration device (L/min)/total surface area of filtration of entire filtration filter film in filtration device (m²)

Here, the filtration flow rate of the fluid flowing though the filtration device can be measured by a flow rate meter (the pressure/flow rate/fluid temperature meter 13 or the flow rate/fluid temperature meter 14 in the organic processing fluid manufacturing system 100) equipped with the fluid input portion or the fluid output portion of the filtration device.

The filtration surface area (m²) of the filtration filter film can typically employ a value represented by a manufacturer of the filtration filter film.

Regardless of how the filtration filter film is arranged, the filtration pressure by the fluid in the filtration device is the pressure of the fluid in the fluid input portion of the filtration device, and the pressure value measured by the pressure/flow rate/fluid temperature meter 13 can be filtration pressure by the fluid in the filtration device 21 in the organic processing fluid manufacturing system 100.

The filtration speed and the filtration pressure of the fluid in the filtration device can be respectively adjusted by controlling the flow rate of the organic fluid to be filtrated by the fluid amount adjusting valve 12 or changing the kind of the filter, the arrangement method of the filter, and the like.

In the above, the method for manufacturing the organic processing fluid for patterning of the chemical amplification type resist film according to the embodiment of the invention is described, but the method for manufacturing the organic processing fluid for patterning of the chemical amplification type resist film according to the invention is not limited to the embodiments described above, and may be appropriately modified or improved.

For example, according to the embodiment described above, the organic processing fluid manufacturing system 100 is configured such that the fluid passing through the filtration device 21 is returned to the fluid tank 11, that is, the circulation line is formed. However, a non-circulation-type organic processing fluid manufacturing system may be employed.

In addition, for example, in the embodiments described above, two-stage filtration method in which two filters are used in series is performed, but one-stage filtration in which plural filters are not used in series (for example, only one filter is used) may be performed, or multi-stage filtration in which three or more filters are used in series may be performed.

Unless having adverse influence on the compatibility between the manufacturing productivity and the manufacturing cost of the organic processing fluid, a filtration method having four or more stages may be performed, but in view of the manufacturing productivity and the manufacturing cost, a two-stage or three-stage filtration method is preferably employed.

In addition, for example, in the organic processing fluid manufacturing system 100 described above, the pump 16 is provided between the flow switching valve 15 and the fluid tank 11 and may be provided between the fluid tank 11 and the filtration device 21.

In addition, the invention relates to organic processing fluid for patterning of the chemical amplification type resist film manufactured by the method for manufacturing the organic processing fluid for patterning of the chemical amplification type resist film according to the embodiment of the invention described above.

Subsequently, a pattern forming method, in which the organic processing fluid manufactured by the method for manufacturing the organic processing fluid for patterning of the chemical amplification type resist film according to the invention is used, is described.

The pattern forming method according to the invention includes (A) a step of forming a film (chemical amplification type resist film) by a chemical amplification type resist composition, (B) a step of exposing the film, and (C) a step of developing the exposed film by using an organic developer.

Here, the organic developer in the step (A) is organic developer manufactured by the method for manufacturing the organic processing fluid for patterning of the chemical amplification type resist film according to the invention described above, and specific examples and preferred examples thereof are as described above.

The exposure in the exposing step may be liquid immersion exposure.

After the exposing step, the pattern forming method according to the invention preferably includes a baking step.

In addition, the pattern forming method according to the invention may further include a developing step by using an alkaline developer.

The pattern forming method according to the invention may include plural exposing steps.

The pattern forming method according to the invention may include plural baking steps.

In the pattern forming method of the invention, the exposing step and the developing step can be performed by methods which are generally known.

After the film is manufactured, before the exposing step, prebake (PB) is preferably included.

In addition, after the exposing step and before the developing step, post exposure bake (PEB) is preferably included.

Both of the PB and PEB are performed at the baking temperature preferably in the range of 70° C. to 130° C. and more preferably in the range of 80° C. to 120° C.

The baking time is preferably in the range of 30 seconds to 300 seconds, more preferably in the range of 30 seconds to 180 seconds, and more preferably in the range of 30 seconds to 90 seconds.

The baking can be performed by means included in general exposing and developing machines, and may be performed by using a hot plate or the like.

The reaction of an exposure portion is promoted by the baking such that sensitivity and a pattern profile is improved.

The light source wavelength used in the exposure device according to the invention is not particularly limited, and an infrared ray, a visible ray, an ultraviolet ray, a far ultraviolet ray, an extreme ultraviolet ray, an X ray, an electron ray, and the like can be included, and a far ultraviolet ray having a wavelength preferably in the range of 250 nm or lower, more preferably in the range of 220 nm or lower, and particularly preferably in the range of 1 nm or 200 nm is included. Specifically, KrF excimer laser (248 nm), ArF excimer laser (193 nm), $F_2$ excimer laser (157 nm), an X ray, EUV (13 nm), an electron ray, and the like are included, and KrF excimer laser, ArF excimer laser, EUV or an electron ray are preferable, and ArF excimer laser is more preferable.

In addition, in the exposing step according to the invention, a liquid immersion exposure method can be applied.

Further, super-resolution techniques such as a phase shift method, a deformed illumination method, and the like, which are currently reviewed, can be combined.

If the liquid immersion exposure is performed, (1) before the exposing step after the film is formed on the substrate and/or (2) before the step of baking the film after the step of exposing the film through the immersion fluid, a step of washing the surface of the film with an aqueous chemical fluid may be performed.

As the immersion fluid, a liquid which is transparent to an exposure wavelength and has as small temperature coefficient of a refractive index as possible such that the deformation of an optical image that is projected on the film is minimized is preferable. However, particularly, if the exposure light source is the ArF excimer laser (wavelength; 193 nm), in addition to the points of view described above, since the acquisition is easy and dealing is easy, water is preferably used.

If water is used, a small percentage of an additive (liquid) that decreases the surface tension of water and also increases surface activity may be added. The additive preferably does not dissolve a resist layer on a wafer and has a negligible influence on an optical coat on the lower surface of a lens element.

As the additive, for example, aliphatic alcohol having substantially the same refractive index as water is preferable, and specifically, methyl alcohol, ethyl alcohol, isopropyl alcohol, and the like are included. If the alcohol having substantially the same refractive index as water is added, there is an advantage in that, even if the alcohol content in water evaporates and the concentration changes, the change of refractive index in the entire liquid can be caused to be as small as possible.

Meanwhile, in a case where materials which are opaque to 193 nm light or impurities which have different refractive index from water are mixed, an optical image which is projected on a resist is deformed. Therefore, as the water used, distilled water is preferable. Further, pure water subjected to filtration by an ion exchange filter or the like may be used.

With respect to water used as the immersion fluid, the electric resistance is preferably 18.3 MΩ cm or greater, TOC (organic matter density) is preferably 20 ppb or lower, and a deaeration treatment is preferably performed.

In addition, if the refractive index of the immersion fluid is increased, the lithography performance can be enhanced. From this point of view, an additive that increases refractive index may be added, or heavy water ($D_2O$) may be used instead of water.

If the film formed by using the composition according to the invention is exposed through an immersion medium, a hydrophobic resin (D) which is described below can be further added, if necessary. If the hydrophobic resin (D) is added, the retreating contact angle of the surface improves. The retreating contact angle of the film is preferably in the range of 60° to 90°, and more preferably in the range of 70° or higher.

In the liquid immersion exposure step, an exposure head performs scanning an area on a wafer at a high speed, and immersion fluid is required to move on the wafer along the movement of the formation of the exposure pattern. Therefore, the contact angle of the immersion fluid to the resist film in a dynamic state becomes important, and thus the resist requires a performance that follows to the high speed scanning of the exposure head.

Between the film formed by using the composition according to the invention and the immersion fluid, a sparingly soluble film in the immersion fluid (hereinafter, also referred to as "top coat") may be provided in order not to cause the film to directly come into contact with the immersion fluid. As a function required for the top coat, application suitability to the upper layer of the resist, transparency to a radiant ray, particularly a radiant ray having a wavelength of 193 nm, and sparingly soluble properties in the immersion fluid are included. It is preferable that the top coat is not mixed with the resist, and also that the top coat can be evenly applied on the upper layer of the resist.

In view of the transparency in 193 nm, the top coat is preferably a polymer that does not contain an aromatic group.

Specifically, a hydrocarbon polymer, an acrylic acid ester polymer, a polymethacrylic acid, polyacrylic acid, polyvinyl ether, a silicon-containing polymer, and a fluorine-containing polymer are included. The hydrophobic resin (D) described above is also preferable as the top coat. If the impurities are eluted from the top coat to the immersion fluid, an optical lens is polluted, and thus it is preferable that remaining monomer components of the polymer included in the top coat are small.

When the top coat is peeled off, a developer may be used, or a separate peeling agent may be used. As the peeling agent, the solvent that penetrates the film less is preferable.

Difference between the refractive indexes of the top coat and the immersion fluid is preferably none or small. In this case, the resolving power can be improved. If the exposure light source is ArF excimer laser (wavelength: 193 nm), since water is preferably used as the immersion fluid, the top coat for the ArF immersion exposure is preferably close to the refractive index (1.44) of water. In addition, in view of the transparency and the refractive index, the top coat is preferably a thin film.

It is preferable that the top coat is not mixed with the film and further is not mixed with the immersion fluid. From this point of view, if the immersion fluid is water, it is preferable that the solvent used in the top coat is sparingly soluble in a dissolving agent used in the composition according to the invention and is a water insoluble medium. Further, if the immersion fluid is an organic solvent, the top coat may be water soluble or water insoluble.

The substrate that forms the film in the invention is not particularly limited, and a substrate that is generally used in a step of manufacturing a semiconductor such as an IC, a step of manufacturing a circuit substrate of liquid crystal, a thermal head, or the like, and a lithography step of other photofabrication, such as an inorganic substrate such as silicon, $SiO_2$, or SiN, or an application-type inorganic substrate such as SOG, can be used. Further, a well-known inorganic or organic antireflective film may be formed between a film and a substrate as necessary.

If a developing step by using an alkaline developer is further performed in the pattern forming method according to the invention, as the alkaline developer, for example, an alkaline aqueous solution such as inorganic alkalis such as sodium hydroxide, potassium hydroxide, sodium carbonate, sodium silicate, sodium metasilicate, and aqueous ammonia, primary amines such as ethylamine, and n-propylamine, secondary amines such as diethylamine, and di-n-butylamine, tertiary amines such as triethylamine and methyl diethylamine, alcohol amines such as dimethyl ethanolamine and triethanolamine, quaternary ammonium salt such as tetramethyl ammonium hydroxide and tetraethyl ammonium hydroxide, and cyclic amines such as pyrrole and piperidine can be used.

Further, appropriate amounts of alcohols and surfactants may be added to the alkaline aqueous solution to be used.

The alkali concentration of the alkaline developer is generally in the range of 0.1% by mass to 20% by mass.

The pH of the alkaline developer is generally in the range of 10.0 to 15.0.

Particularly, 2.38% by mass of the aqueous solution of tetramethyl ammonium hydroxide is preferable.

In addition, if the development by an organic developer and the development by the alkaline developer are combined, it can be expected that a pattern having a line width of ½ of a mask pattern can be resolved as described in FIGS. 1 to 11 and the like of U.S. Pat. No. 8,227,183B.

As the rinse fluid in a rinse treatment performed after the alkali development, pure water is used, and an appropriate amount of a surfactant can be added to be used.

In addition, after the development treatment or the rinse treatment, a treatment of removing the developer or the rinse fluid attached to the pattern with a supercritical fluid can be performed.

As described above, the organic developer in the step of developing the exposed film by using the organic developer is an organic developer manufactured by the method for manufacturing the organic processing fluid for patterning of the chemical amplification type resist film according to the invention. As the developing method, for example, a method of dipping a substrate in a tank filled with a developer for a certain period of time (dip method), a developing method performed by heaping up a developer on a substrate surface by a surface tension and causing the developer to rest for a certain period of time (paddle method), a method of spraying a developer on a substrate surface (spray method), and a method of continuously discharging a developer while scanning a developer discharging nozzle at a certain speed on a substrate rotating at a certain speed (dynamic disperse method) can be applied.

If the various developing methods include a step of discharging a developer from a developing nozzle of a developing device to a resist film, a discharge pressure of a discharged developer (flow velocity for unit area of a discharged developer) is preferably 2 $mL/sec/mm^2$ or lower, more preferably 1.5 $ml/sec/mm^2$ or lower, and still more preferably 1 $mL/sec/mm^2$ or lower. The lower limit of the flow velocity is not particularly limited, and is preferably 0.2 $mL/sec/mm^2$ or higher considering throughput.

If the discharge pressure of the discharged developer to be in the range described above, a defect of the pattern caused by a resist residue after the development can be remarkably reduced.

The specific mechanism is not clear, but it is probably considered that, if the discharge pressure is in the range described above, the pressure applied by the developer to the resist film becomes small and the resist film or the resist pattern is prevented from being carelessly sharpened or ruined.

In addition, a discharge pressure ($mL/sec/mm^2$) of the developer is a value in a developing nozzle outlet in the developing device.

As a method of adjusting the discharge pressure of the developer, for example, a method of adjusting the discharge pressure by a pump or the like and a method of changing the pressure by adjusting the pressure by a supply from a pressure tank and the like are included.

In addition, after the developing step by using the developer including the organic solvent, a step of stopping the development while substituting the developer with another dissolving agent may be performed.

The developing device using the developing step by using the organic developer is preferably an application developing device that can apply an organic developer, and as the application developing device, LITHIUS, LITHIUS i+, LITHIUS Pro, LITHIUS Pro-i, LITHIUS Pro V, and LITHIUS Pro V-i, manufactured by Tokyo Electron Limited, and $RF^{3S}$, and SOKUDO DUO manufactured by SOKUDO are included.

Filters for connection chemical fluids (filters for processing fluid) called POU filters are typically mounted on these application developing devices.

Accordingly, in the developing step, together with using a POU-mounted application developing device (developing device on which a filter for processing fluid is mounted), the organic processing fluid for patterning (particularly, organic developer) according to the invention may be caused to pass through the POU filter to be used in the development.

When the organic processing fluid for patterning according to the invention is used in the POU-mounted application developing device, two methods described below are preferably performed.

1. When a new POU filter is used, 30 L or more of the processing fluid used right after the device is set is caused to pass through the POU filter.

2. If unused time is 6 hours or longer, 1 L or more of dummy dispensation is performed right before the use.

The pattern forming method according to the invention further preferably includes a washing step by using the organic rinse fluid, after the developing step using the organic developer.

Here, the organic rinse fluid is an organic rinse fluid manufactured by the method for manufacturing the organic processing fluid for patterning of the chemical amplification type resist film according to the invention described above, and specific examples and preferred examples are as described above.

In the rinsing step, a wafer in which the development is performed by using the developer including the organic solvent is subjected to the washing treatment by using the rinse fluid including the organic solvent. The method of the washing treatment is not particularly limited, and, for example, a method of continuously discharging a rinse fluid on a substrate rotating at a certain speed (rotation application method), a method of dipping a substrate in a tank filled with a rinse fluid for a certain period of time (dip method), and a method of spraying a rinse fluid on a substrate surface (spray method) can be applied. Among them, it is preferable that the washing treatment is performed by the rotation application method, the substrate after the washing is caused to rotate at a rotation speed of 2,000 rpm to 4,000 rpm, and the rinse fluid is removed from the substrate. In addition, after the rinsing step, a baking step (Post Bake) is preferably included. By the baking, the developer and the rinse fluid remaining between the patterns and inside of the pattern are removed. The baking step after the rinsing step is performed generally in a range of 40° C. to 160° C., and preferably in a range of 70° C. to 95° C., and performed generally in the range of 10 seconds to 3 minutes, and preferably in the range of 30 seconds to 90 seconds.

The pattern forming method according to the invention further includes a washing step by using the organic rinse fluid after the developing step by using the organic developer, in which the organic developer is butyl acetate as the organic processing fluid obtained by the method for manufacturing the organic processing fluid for patterning of the chemical amplification type resist film according to the invention described above, and the organic rinse fluid is butyl acetate as the organic processing fluid obtained by the method for manufacturing the organic processing fluid for patterning of the chemical amplification type resist film according to the invention described above.

The chemical amplification type resist composition used in the pattern forming method according to the invention is not particularly limited as long as the composition is the type of resist composition of which the chemical reactions in a system which has the exposure as a momentum are catalytically chained, and typically a chemical amplification type resist having a portion or all of components described below is preferably used.

[1] (A) Resin of which polarity increases and solubility in a developer including an organic solvent decreases by an action of an acid As the resin (A) of which polarity increases and solubility in a developer including an organic solvent decreases by an action of an acid, for example, a resin (hereinafter, referred to as an "acid-decomposable resin" or the "resin (A)") having a group (hereinafter, referred to as an "acid-decomposable group") that is decomposed by an action of an acid and produces a polar group in a main chain, a side chain, or both of the main chain and the side chain of the resin can be included.

The acid-decomposable group preferably has a structure protected by a group that decomposes a polar group by an action of an acid and is released. As a preferable polar group, a carboxyl group, a phenolic hydroxyl group, a fluorinated alcohol group (preferably, a hexafluoroisopropanol group), and a sulfonic acid group are included.

A group which is preferable as the acid-decomposable group is a group substituted with the group of releasing a hydrogen atom of this group by an acid.

As the group which is released by an acid, for example, —C($R_{36}$)($R_{37}$)($R_{38}$), —C($R_{36}$)($R_{37}$)(O$R_{39}$), and —C($R_{01}$)($R_{02}$)(O$R_{39}$) can be included.

In the formula, $R_{36}$ to $R_{39}$ independently represent an alkyl group, a cycloalkyl group, an aryl group, an aralkyl group, or an alkenyl group. $R_{36}$ and $R_{37}$ may be combined with each other, so as to form a ring.

$R_{01}$ and $R_{02}$ independently represent a hydrogen atom, an alkyl group, a cycloalkyl group, an aryl group, an aralkyl group, or an alkenyl group.

As the acid-decomposable group, a cumyl ester group, an enol ester group, an acetal ester group, and a tertiary alkyl ester group are preferable. A tertiary alkyl ester group is more preferable. In addition, when the pattern forming method according to the invention is performed by the exposure by a KrF ray or a EUV ray or the irradiation with an electron ray, an acid-decomposable group in which a phenolic hydroxyl group is protected by an acid releasing group.

The resin (A) preferably has a repeating unit having an acid-decomposable group.

As the repeating unit, the following are included.

In the specific examples, Rx represents a hydrogen atom, $CH_3$, $CF_3$, or $CH_2OH$. Rxa and Rxb each represent alkyl groups having 1 to 4 carbon atoms. $Xa_1$ represents a hydrogen atom, $CH_3$, $CF_3$, or $CH_2OH$. Z represents a substituent, and if there are plural Zs, the plural Zs may be identical to or different from each other. p represents 0 or a positive integer. Specific examples and preferred examples of Z are the same as the specific examples and preferred examples of substituents which respective groups of $Rx_1$ to $Rx_3$ may include.

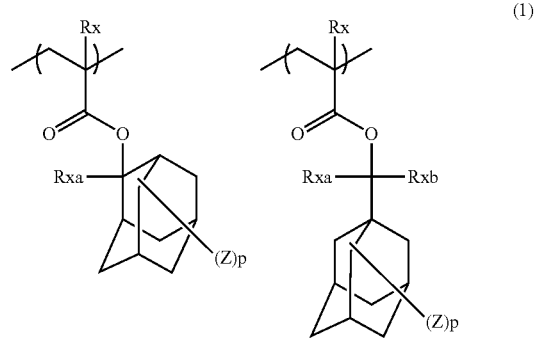

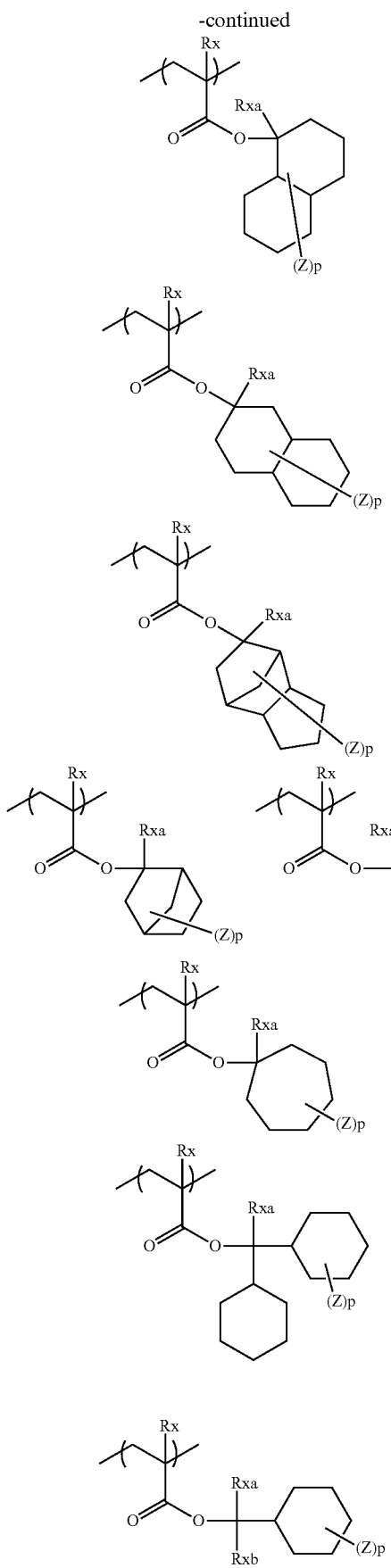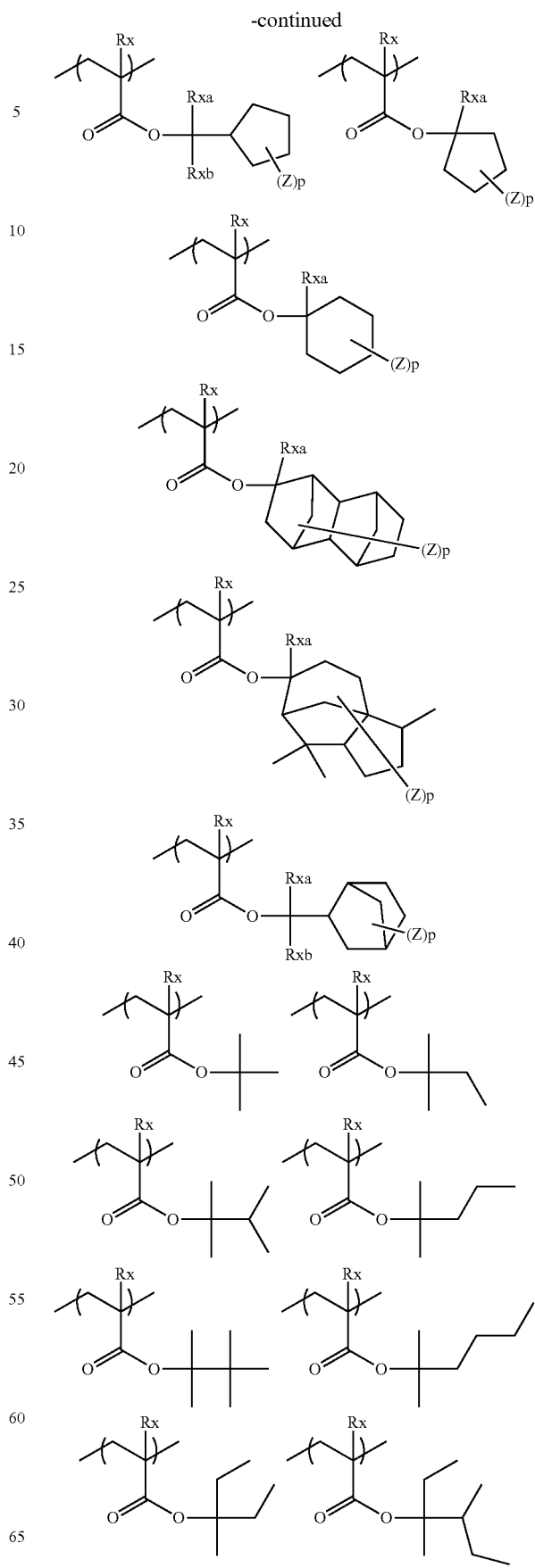

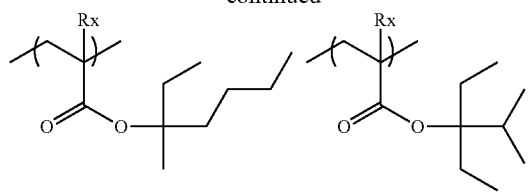
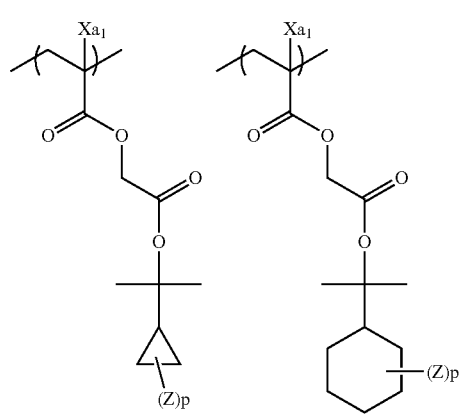
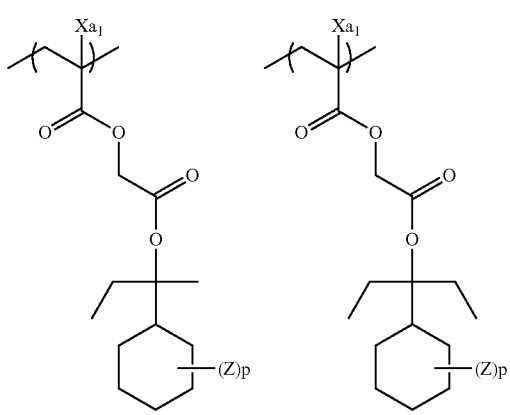
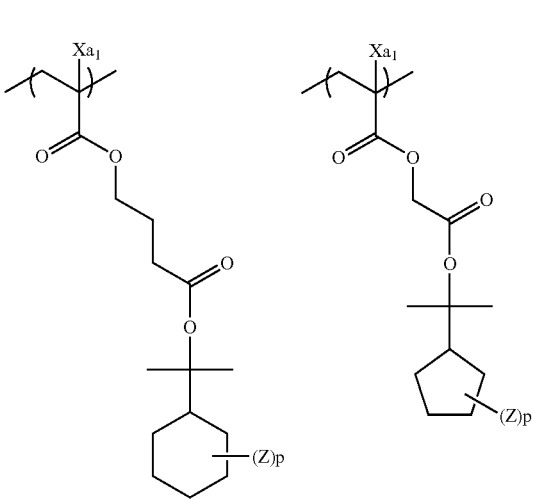
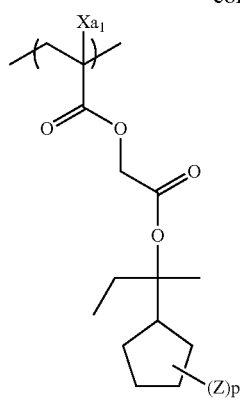
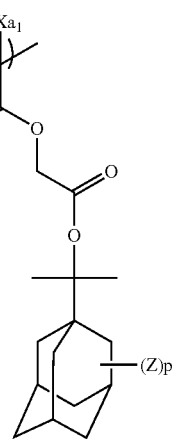
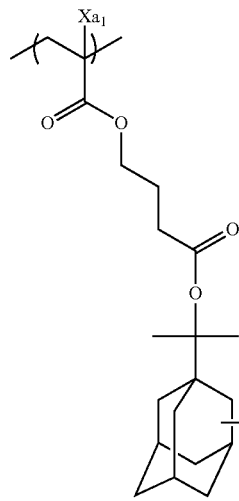
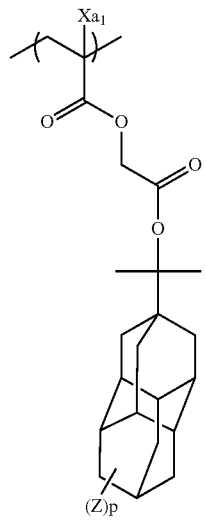
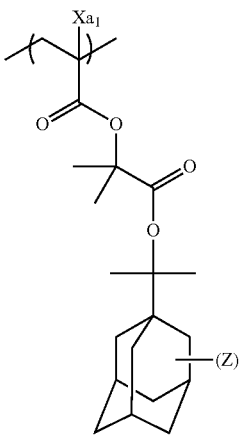
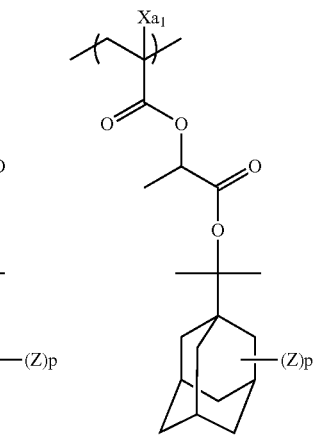

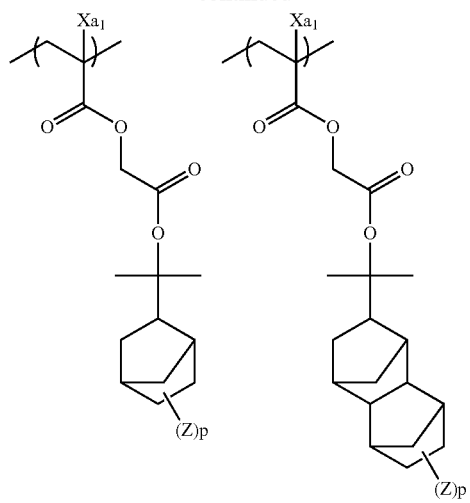
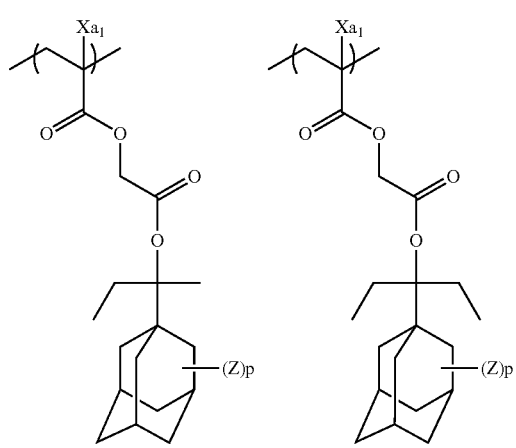
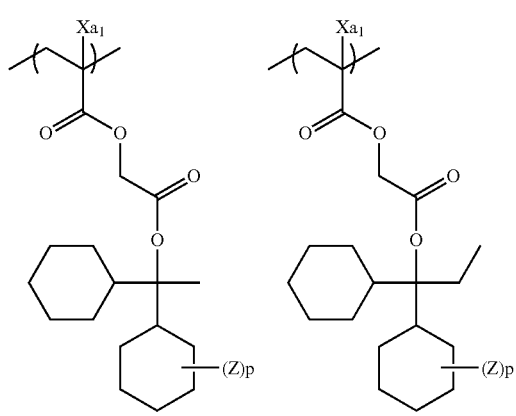
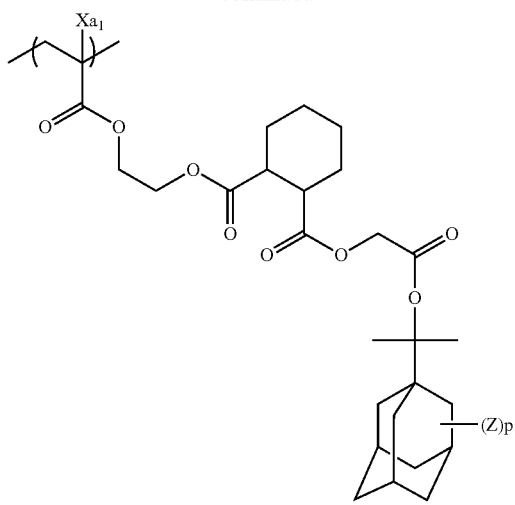
(3)
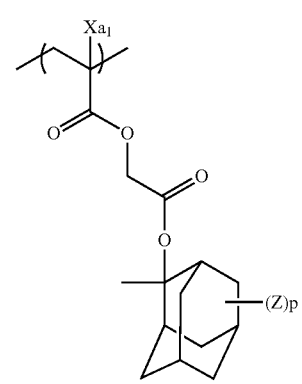
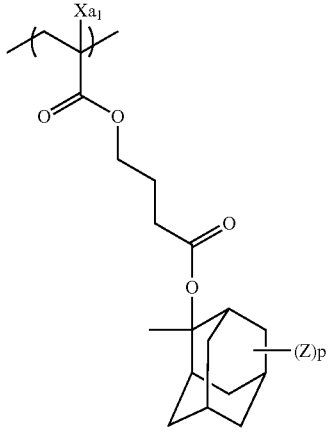
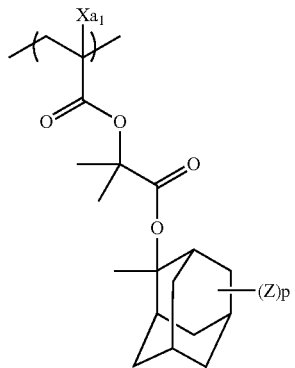

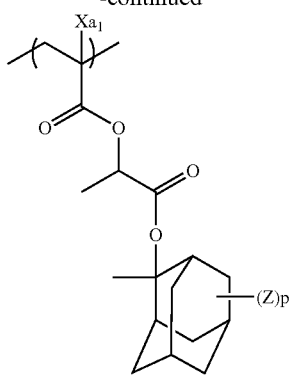
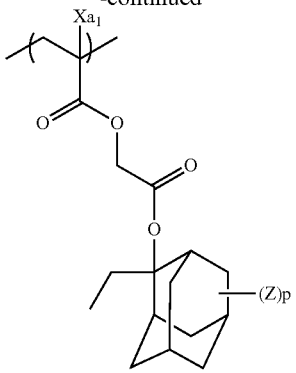
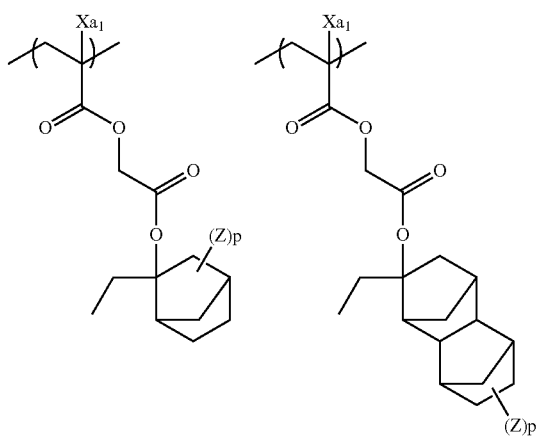
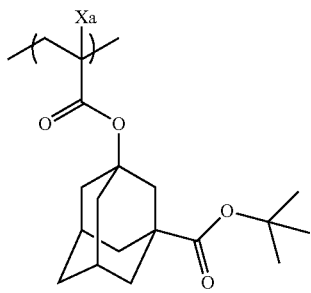
In the specific examples described below, Xa refers to a hydrogen atom, an alkyl group, a cyano group, or a halogen atom.
(4)
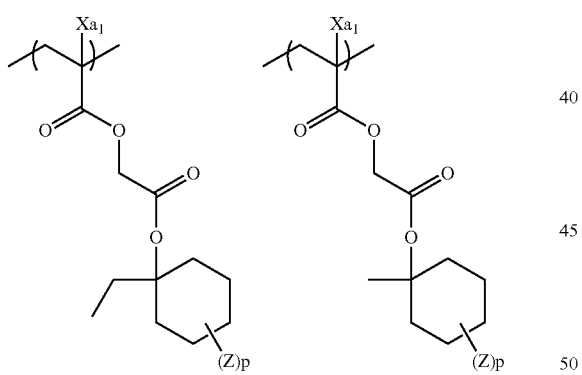
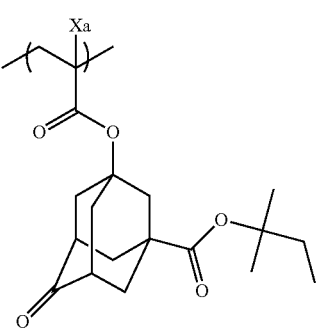
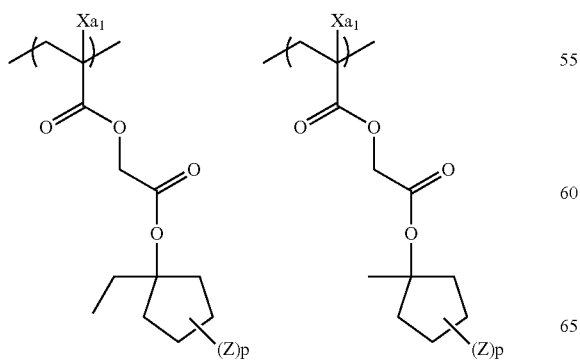

-continued
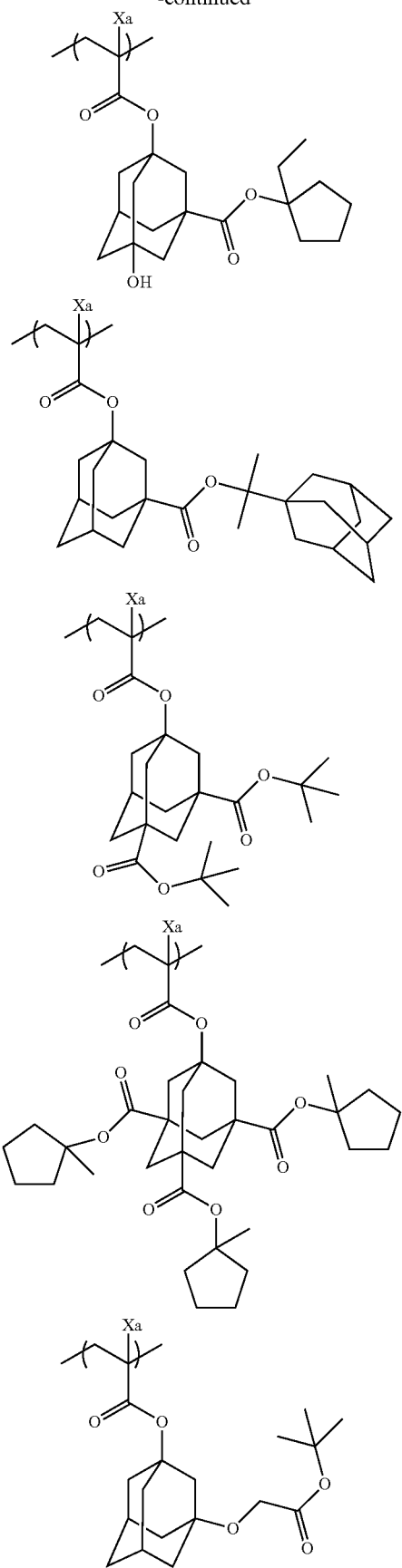
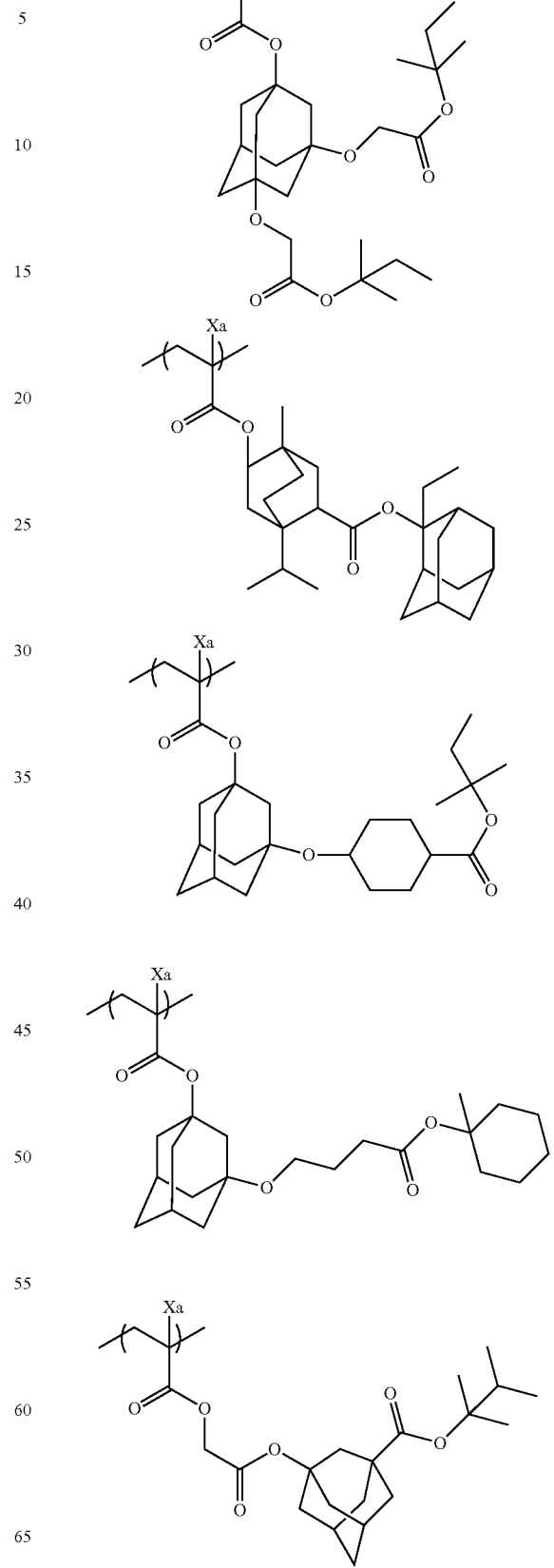

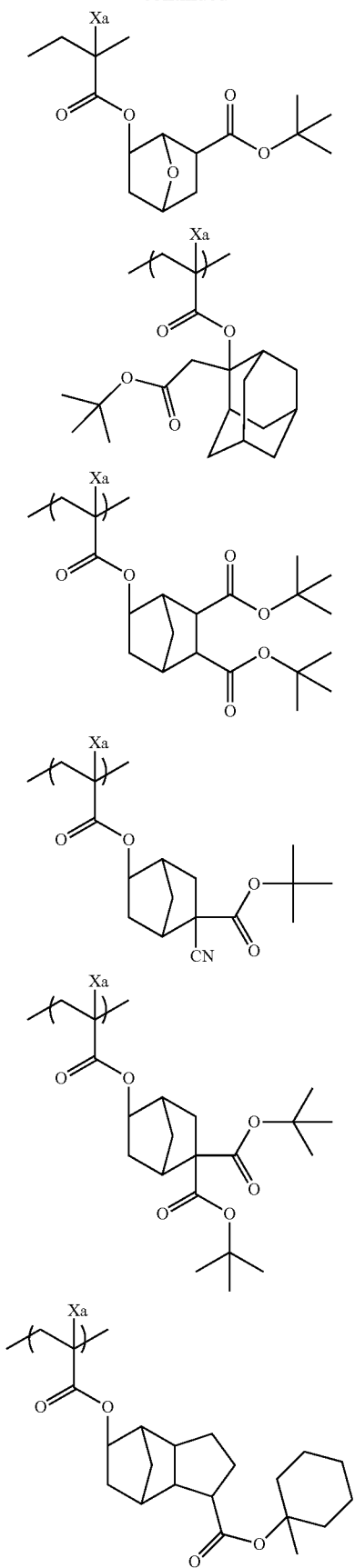
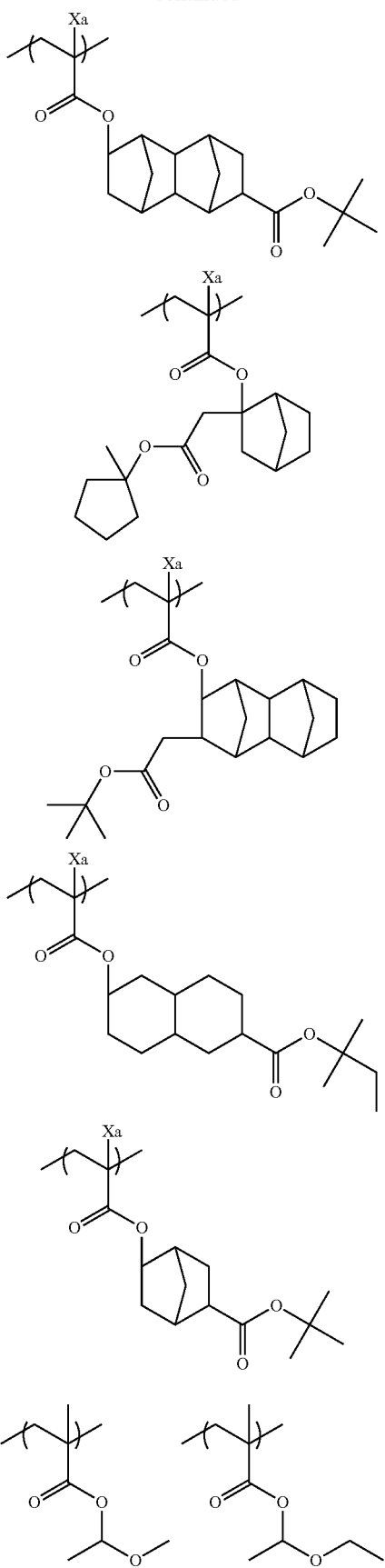
(5)

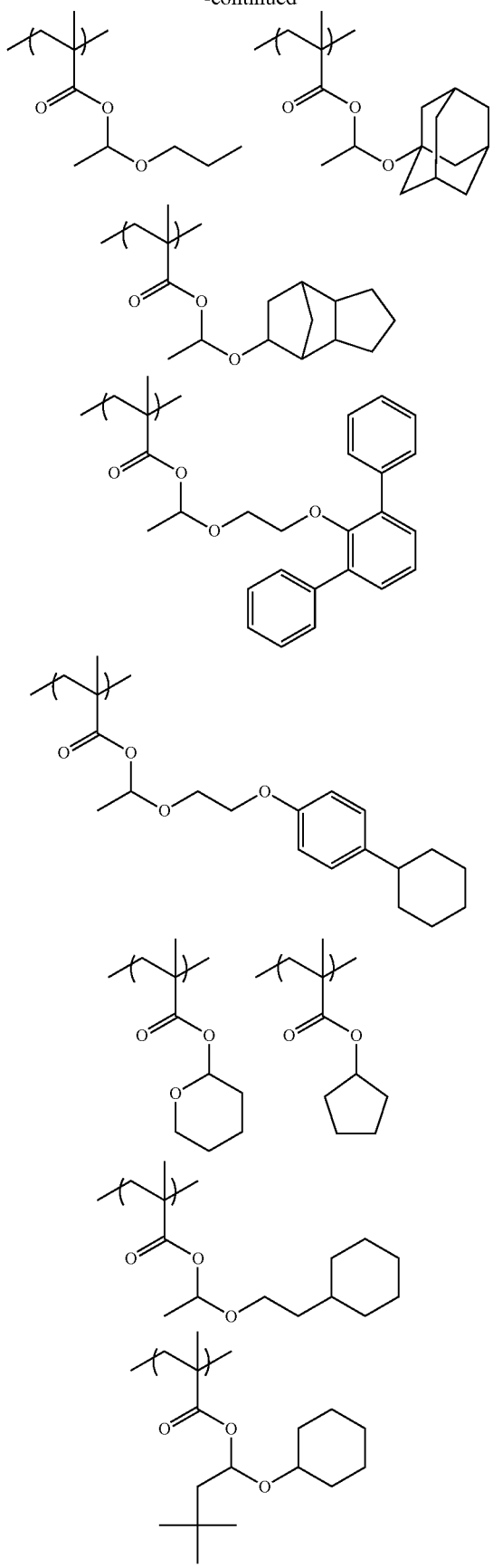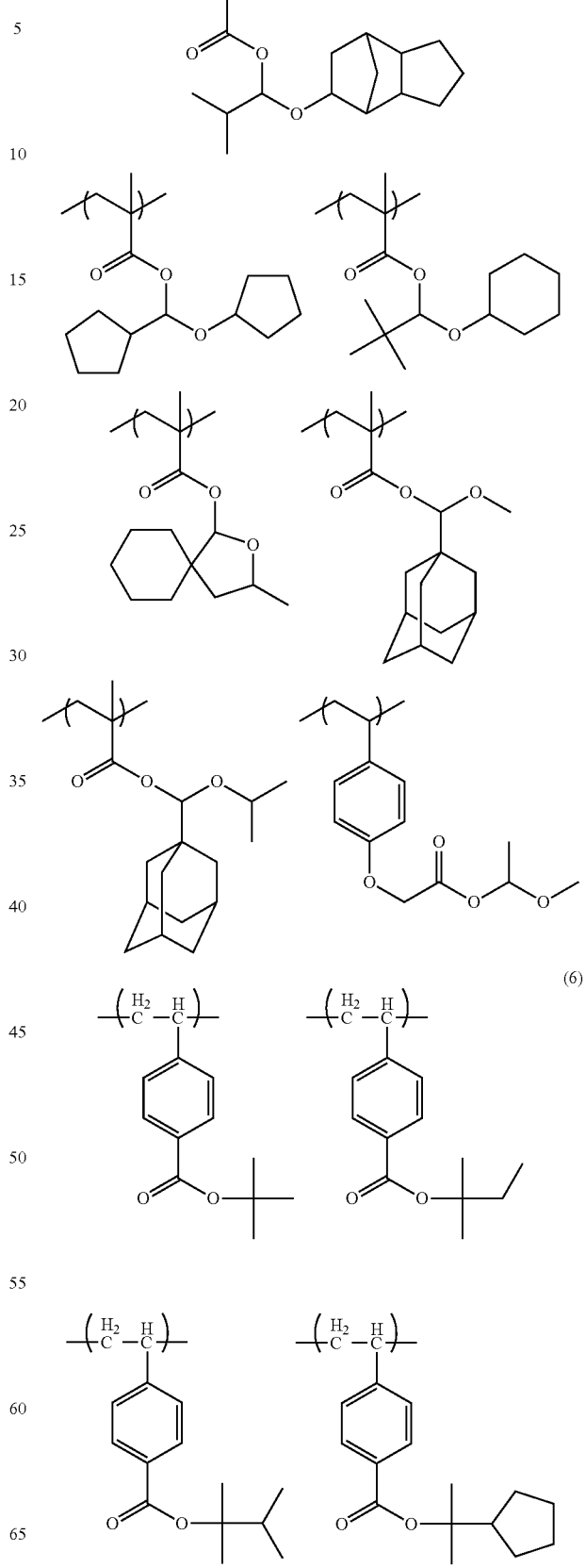

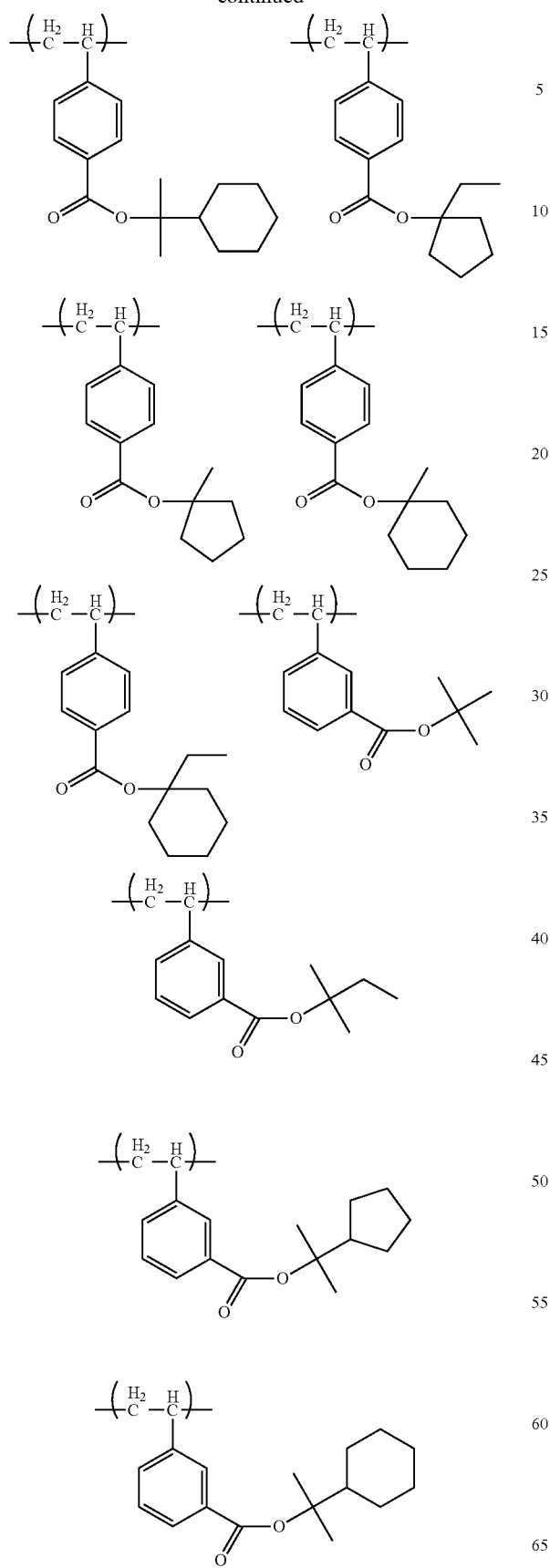
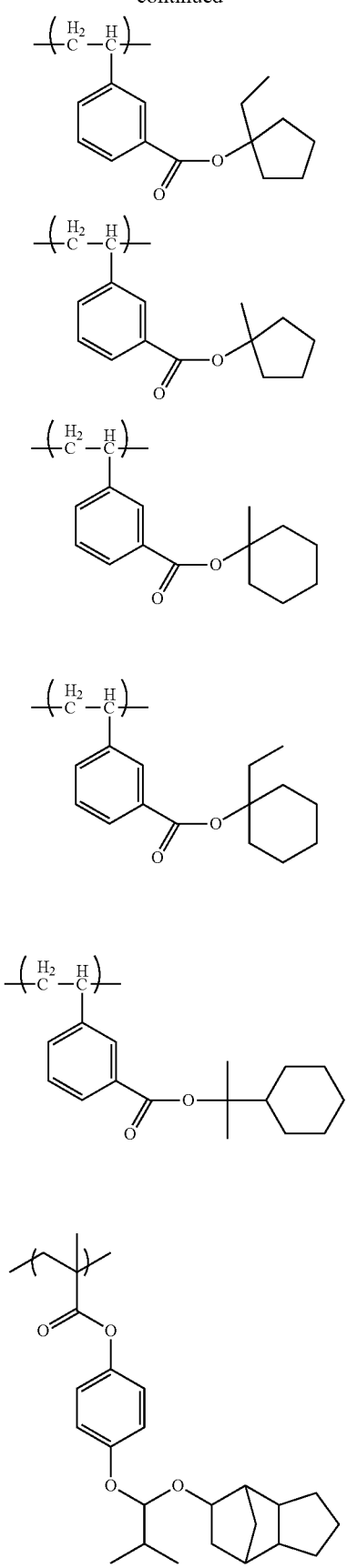
(7)

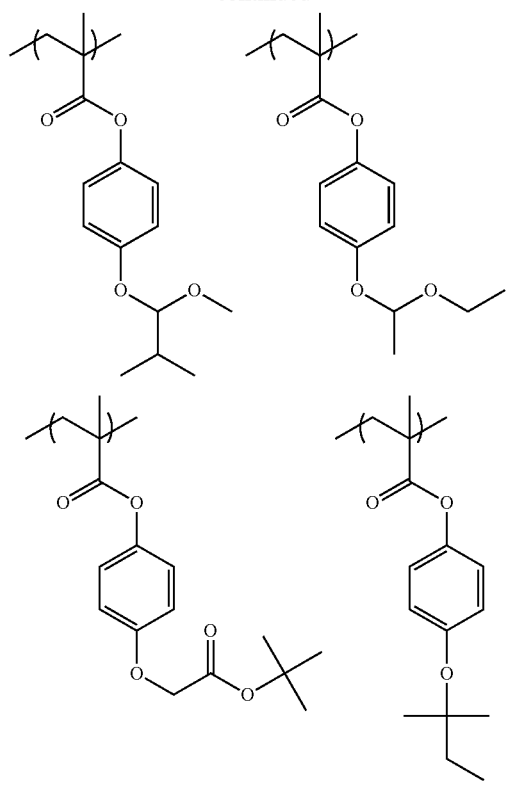
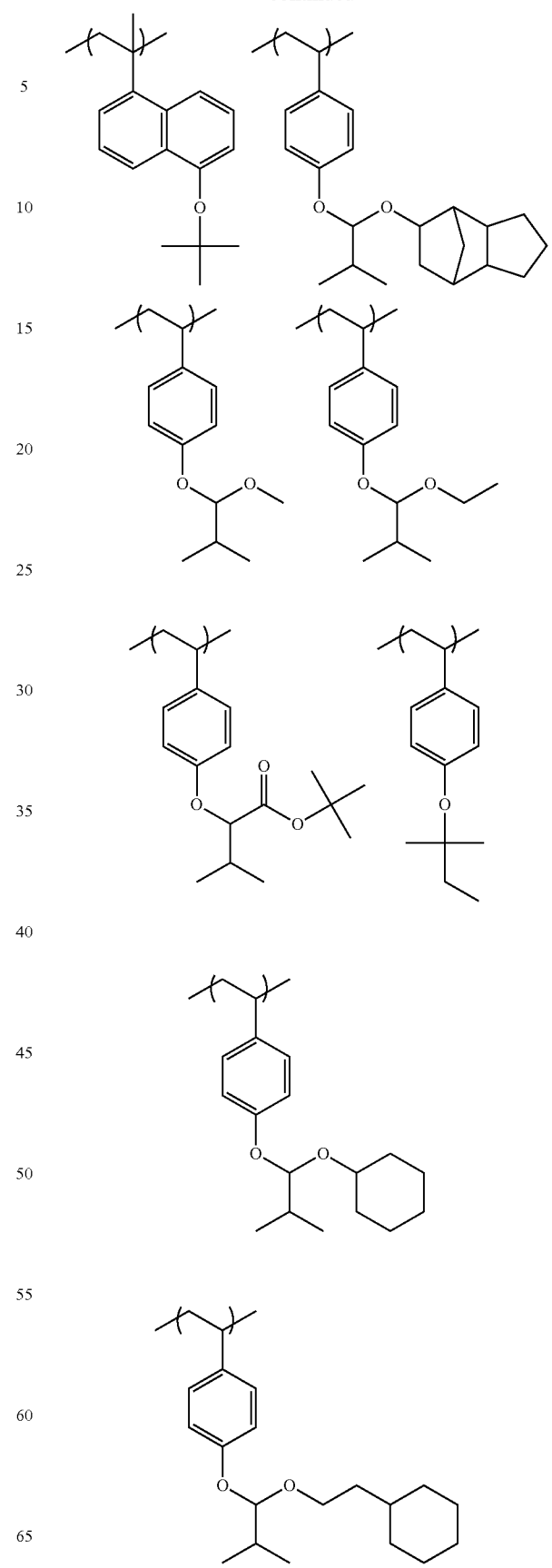

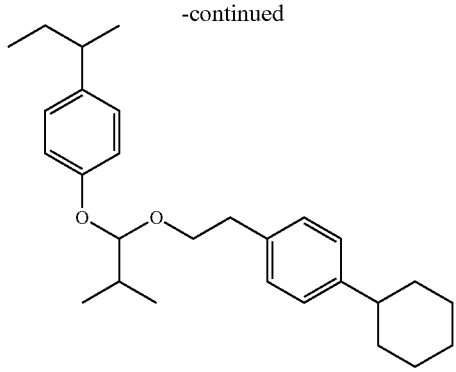
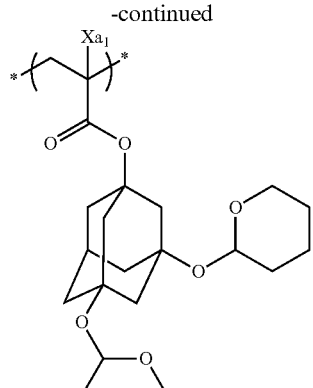
In the specific examples described below, $Xa_1$ represents a hydrogen atom, $CH_3$, $CF_3$, or $CH_2OH$.
(8)
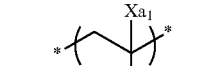
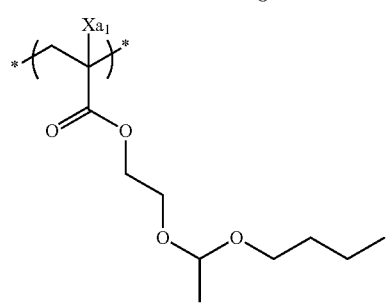
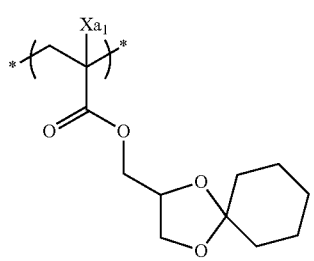 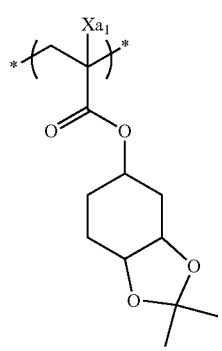
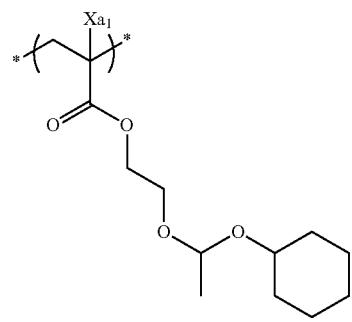
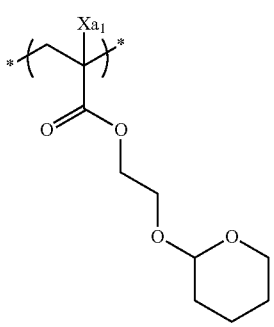
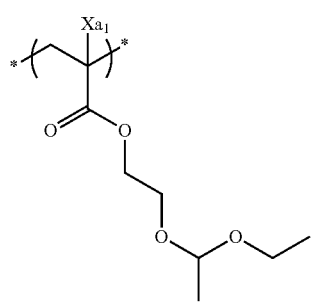

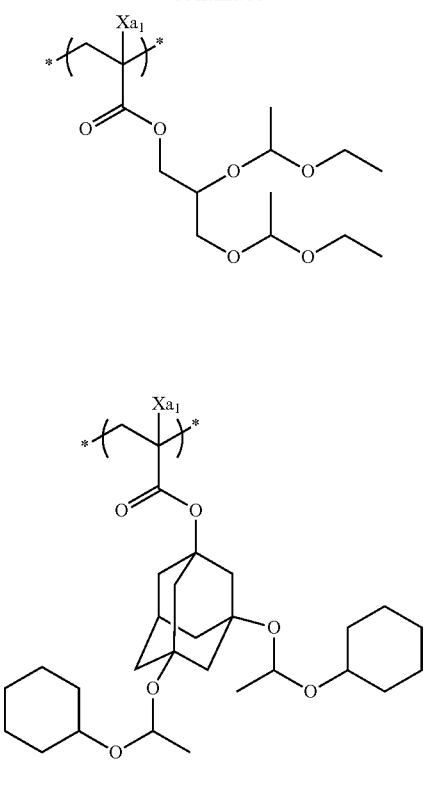

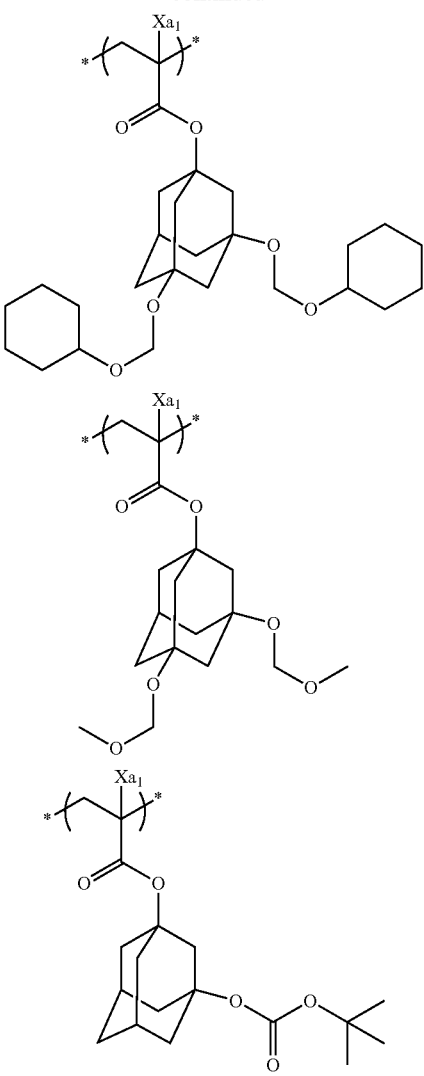

The repeating unit having the acid-decomposable group may be used singly, or two or more types thereof may be used in combination. The combination in which two types thereof are used in combination is not particularly limited, and, for example, the following combinations are considered. In the formulae described below, R independently represents a hydrogen atom or a methyl group.

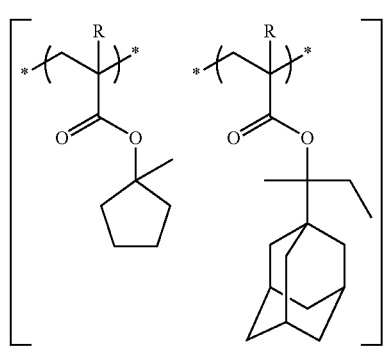

(9)

-continued
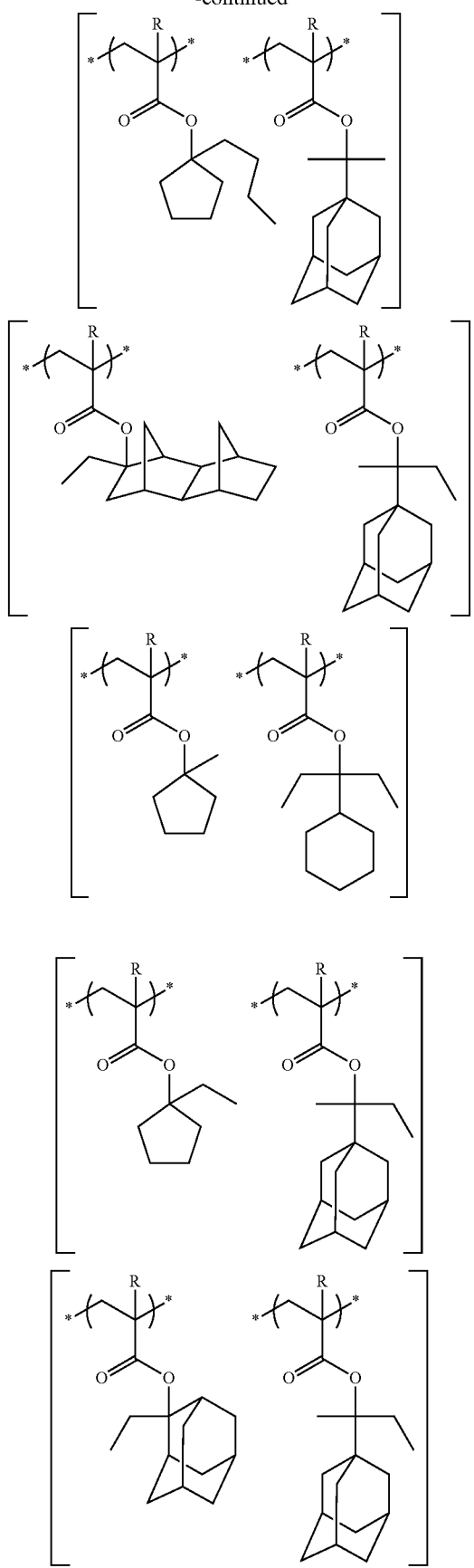
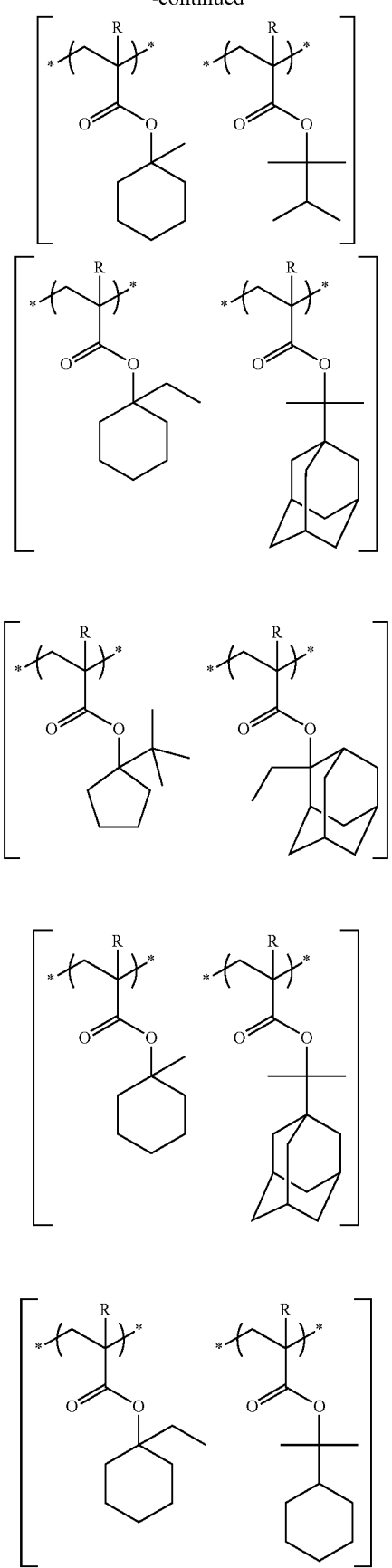

-continued
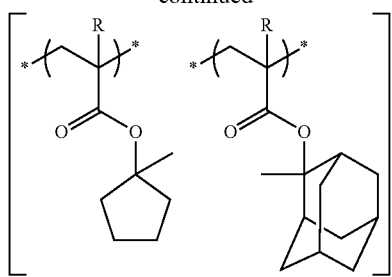
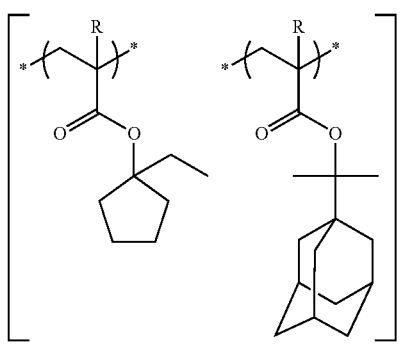
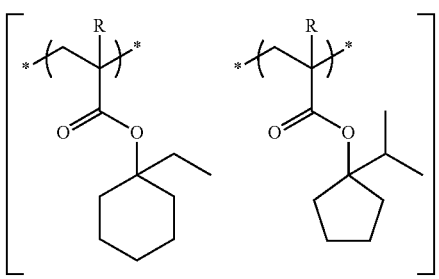
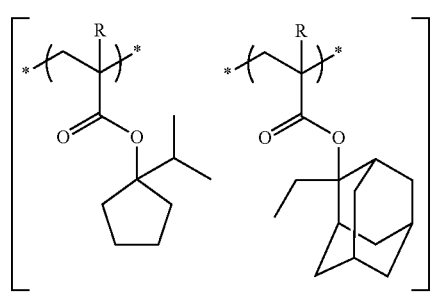
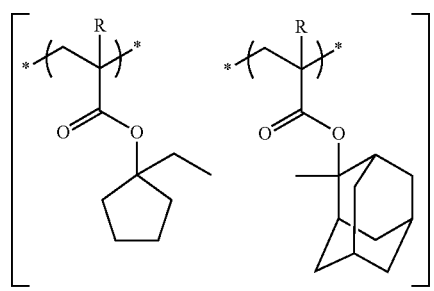
-continued
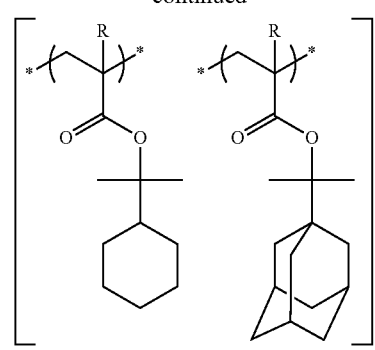
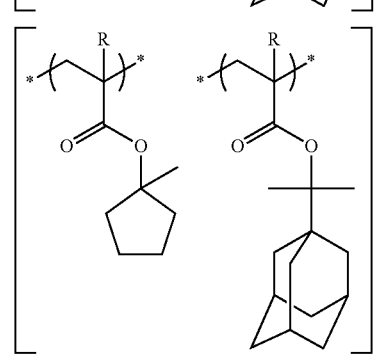
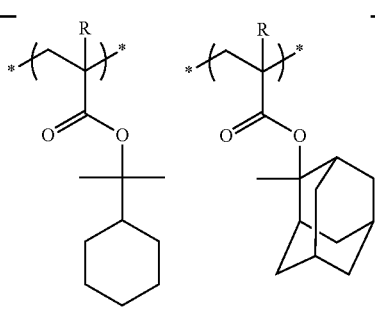
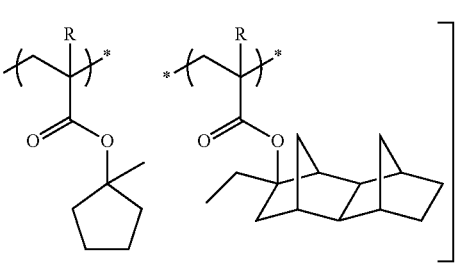
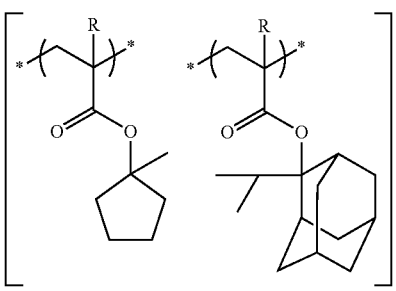

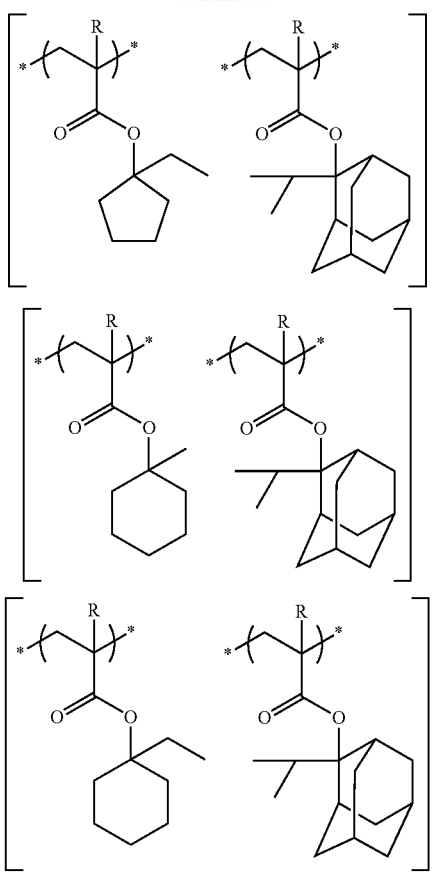

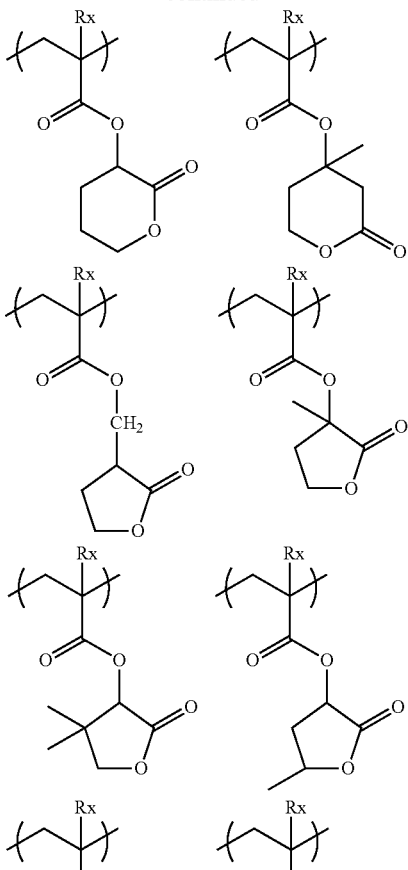

The content (the total amount of the repeating unit if plural repeating units having the acid-decomposable groups exist) of the repeating unit having the acid-decomposable group included in the resin (A) is preferably 15% by mol or more, more preferably 20% by mol or more, still more preferably 25% by mol or more, and particularly preferably 40% by mol or more with respect to the total repeating units of the resin (A).

The resin (A) may contain a repeating unit having a lactone structure or a sultone structure.

Hereinafter, specific examples of the repeating units having groups having a lactone structure or a sultone structure are described, but the invention is not limited thereto.

(In the formula, Rx represents H, CH$_3$, CH$_2$OH, or CF$_3$.)

(10)

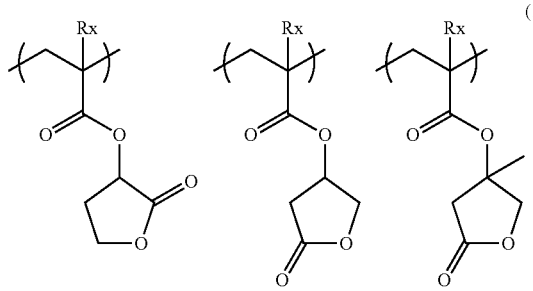

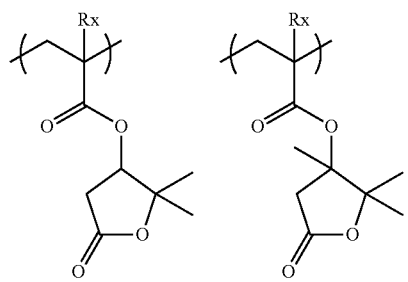

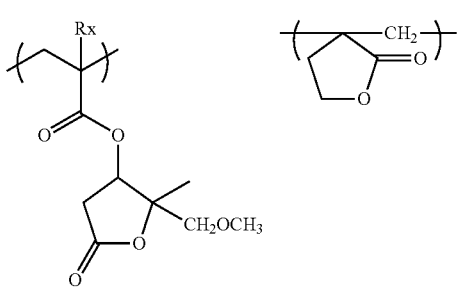

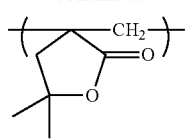
(In the formula, Rx represents H, CH₃, CH₂OH, or CF₃.)
(11)
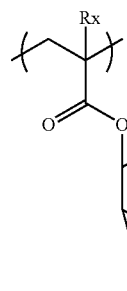 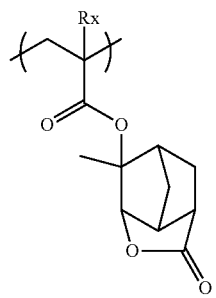
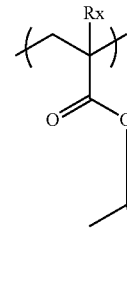
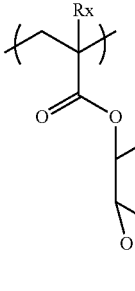
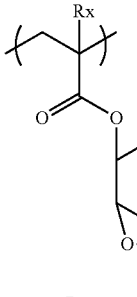 
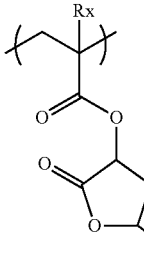 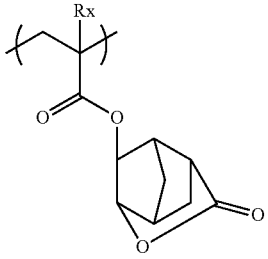
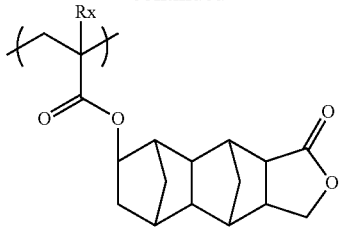
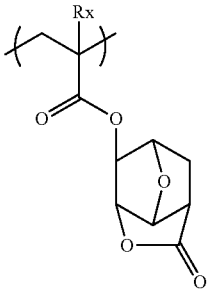 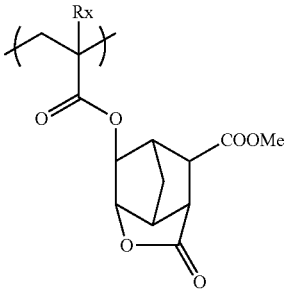
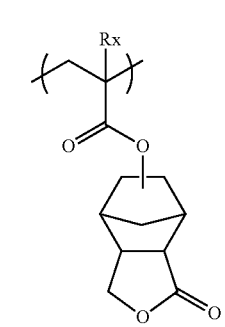 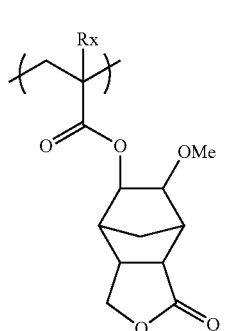
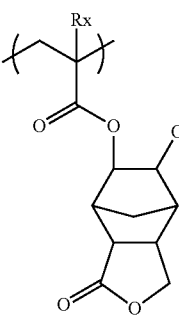 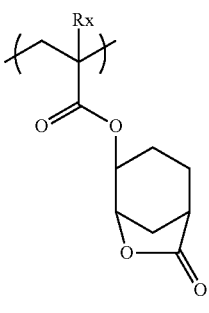
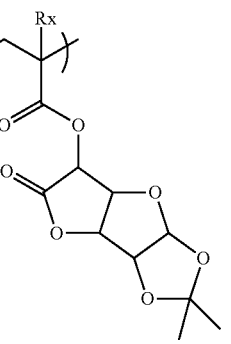 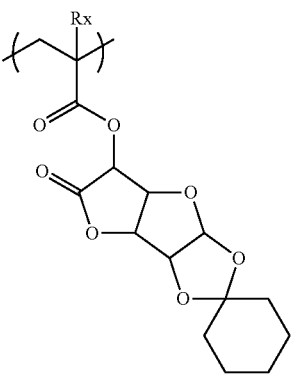

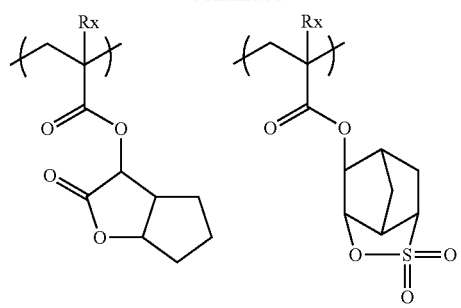
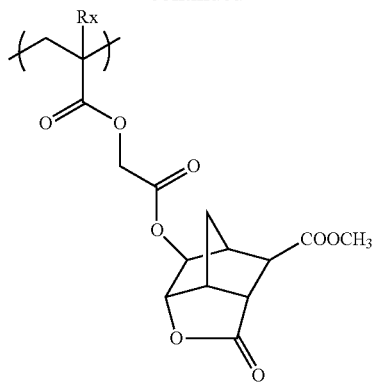
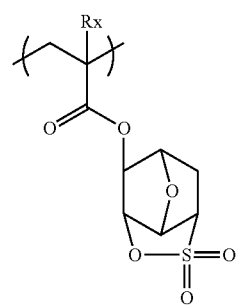
(In the formula, Rx represents H, CH$_3$, CH$_2$OH, or CF$_3$.)
(12)
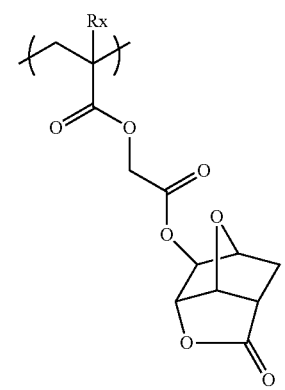
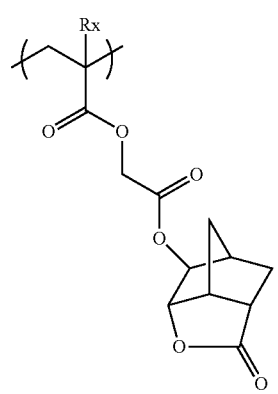
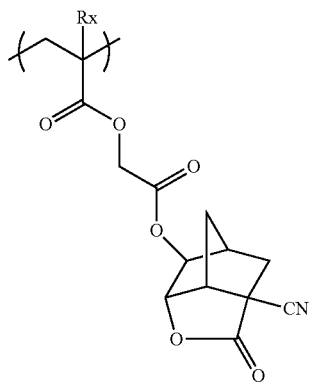
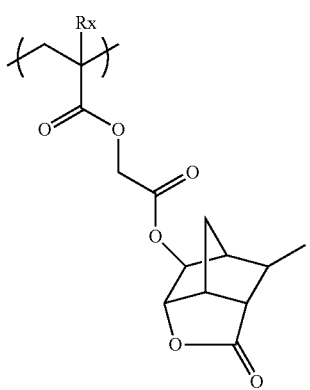
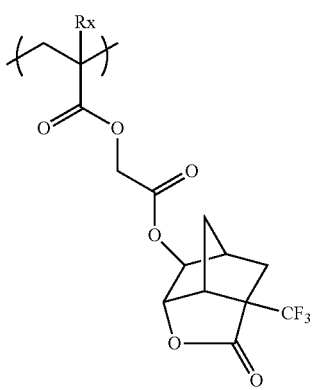

53
-continued
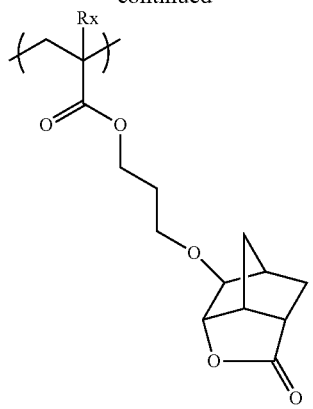
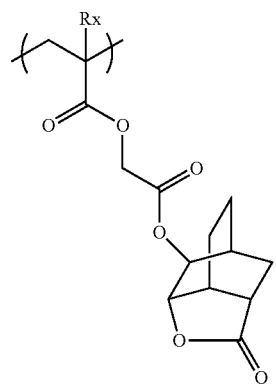
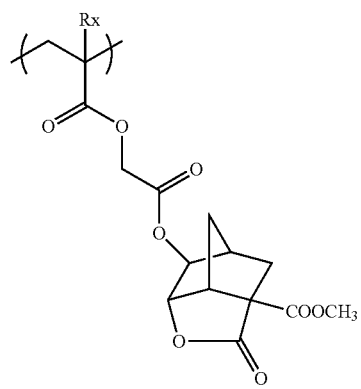
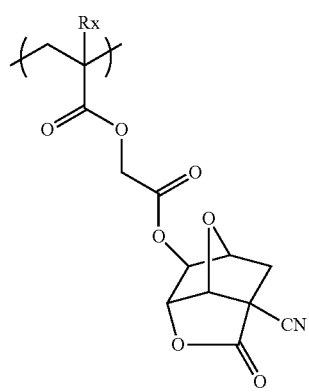
54
-continued
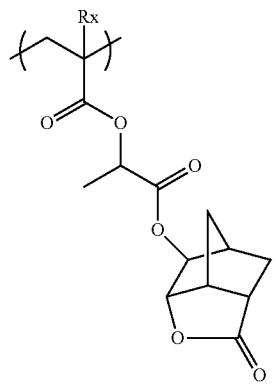
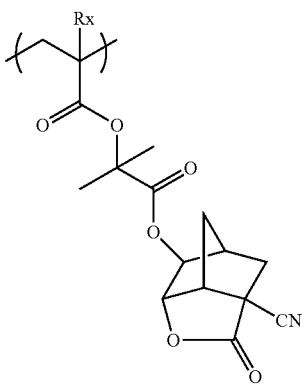
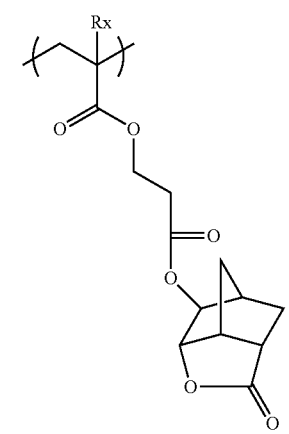
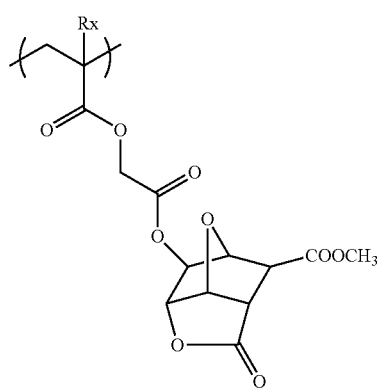

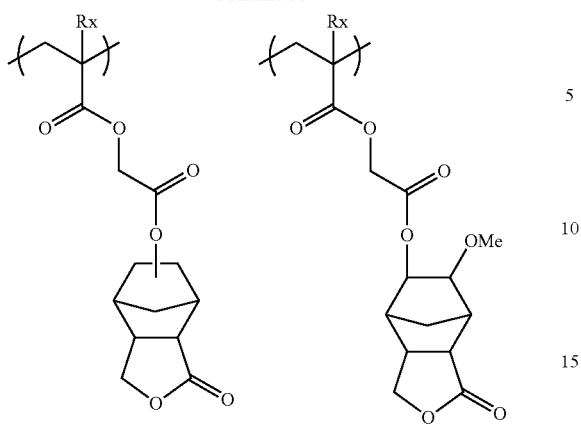

2 or more kinds of repeating units having a lactone structure or a sultone structure may be used in combination.

If the resin (A) contains a repeating unit having a lactone structure or a sultone structure, the content of the repeating unit having a lactone structure or a sultone structure is preferably 5% by mol to 60% by mol, more preferably 5% by mol to 55% by mol, and still more preferably 10% by mol to 50% by mol, with respect to the total repeating units in the resin (A).

In addition, the resin (A) may include a repeating unit having a cyclic carbonic acid ester structure. Specific examples are presented below, but the invention is not limited thereto.

In addition, $R_A^1$ in specific examples described below represents a hydrogen atom or an alkyl group (preferably, methyl group).

(13)

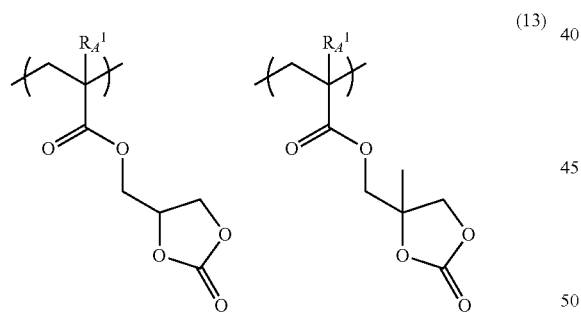

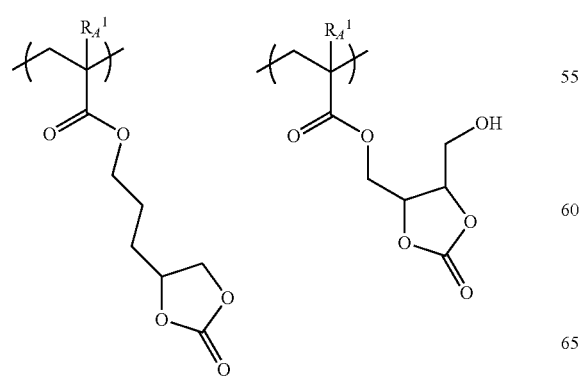

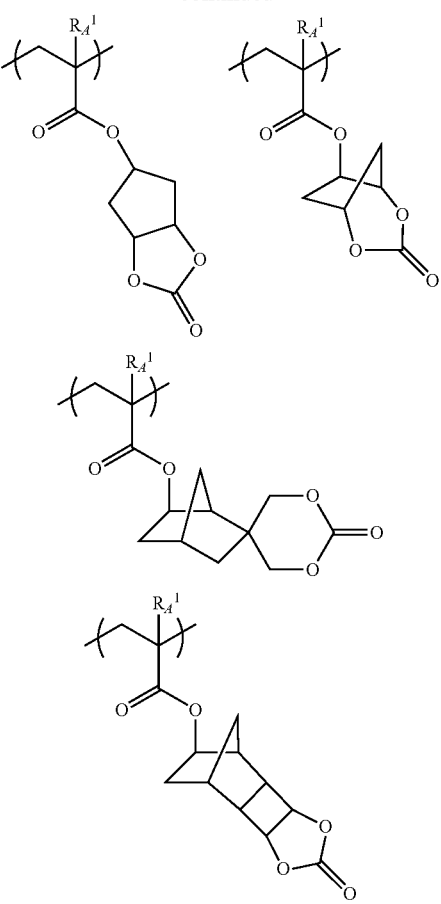

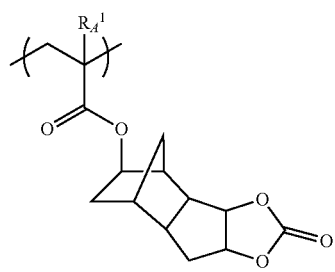

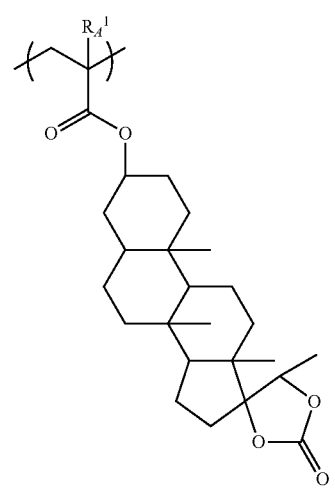

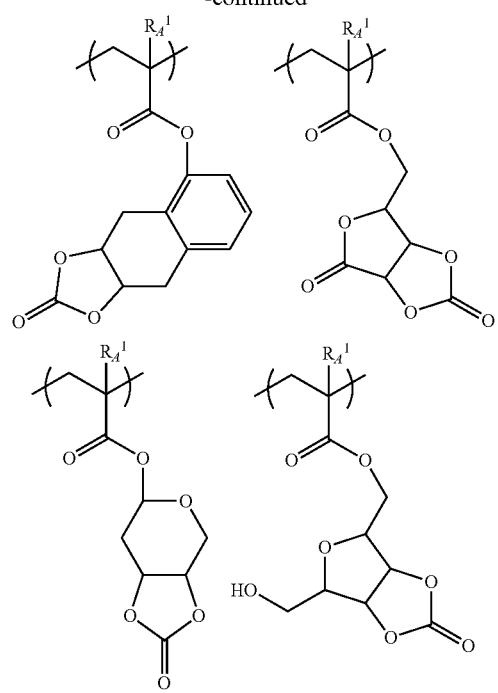
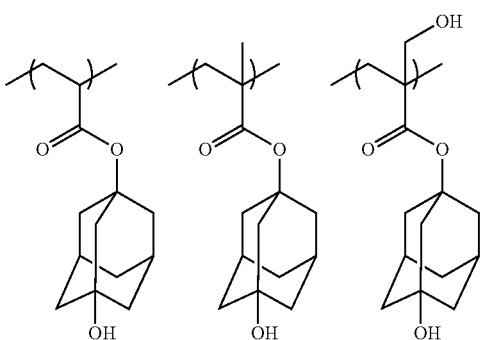
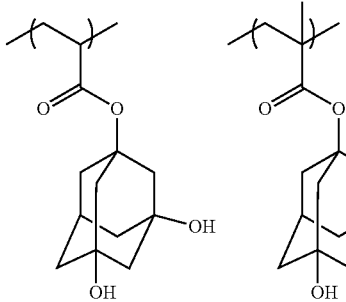
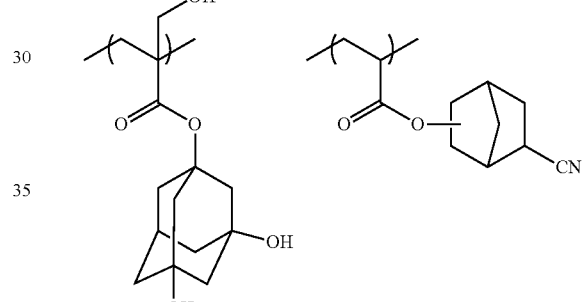
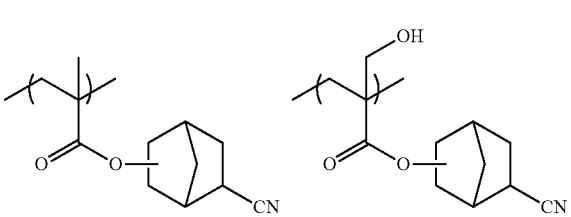
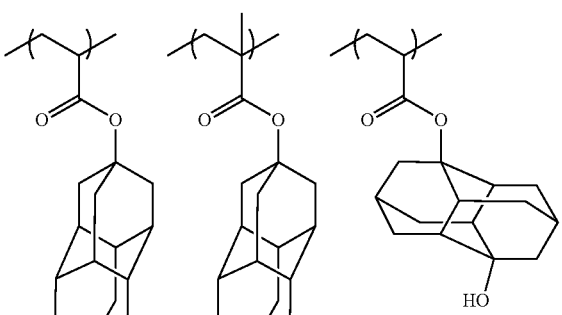
The resin (A) may include a repeating unit having a hydroxyl group or a cyano group.
Specific examples of the repeating unit having a hydroxyl group or a cyano group are described below, but the invention is not limited thereto.

-continued

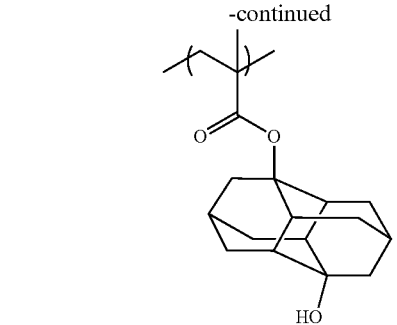

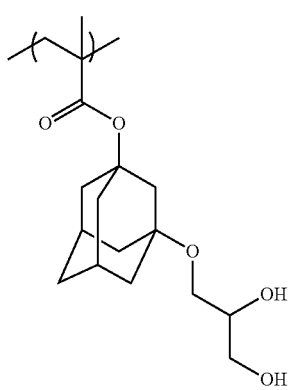

(15)

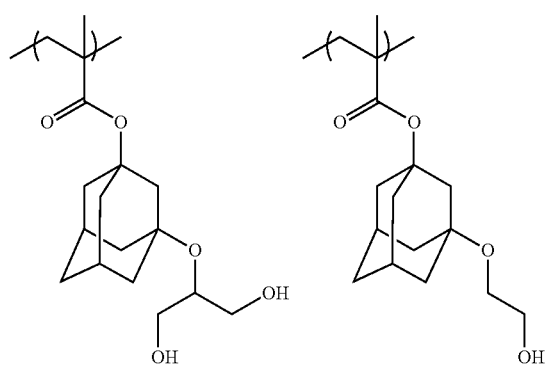

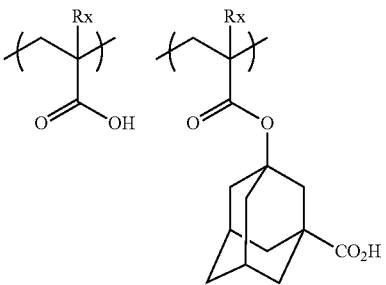

(16)

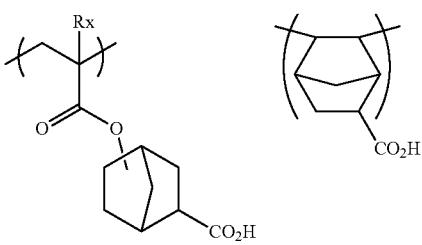

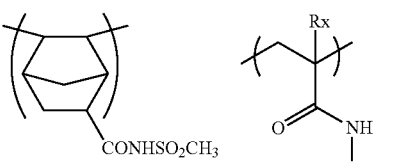

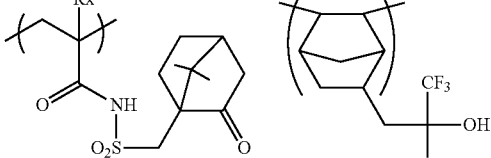

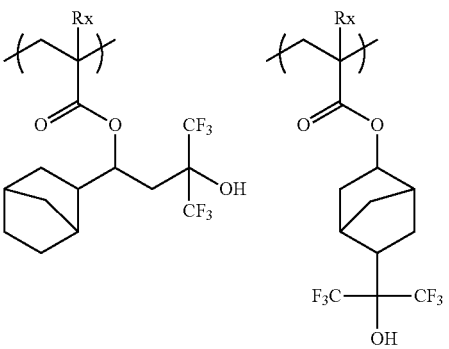

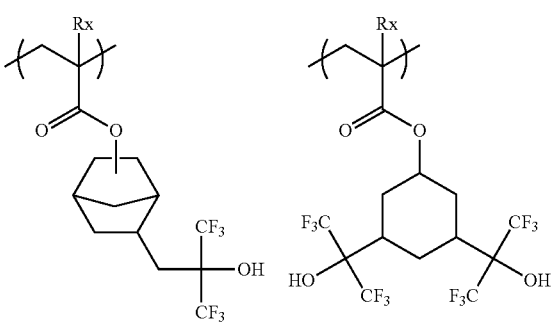

The resin (A) may include a repeating unit having an acid group.

The resin (A) may not contain a repeating unit having an acid group, but if the resin (A) contains a repeating unit having an acid group, the content of the repeating unit having the acid group is preferably 25% by mol or lower and more preferably 20% by mol or lower with respect to the total repeating units in the resin (A). If the resin (A) contains a repeating unit having an acid group, the content of the repeating unit having the acid group in the resin (A) is generally 1% by mol or more.

The specific examples of the repeating unit having the acid group is described below, but the invention is not limited thereto.

In the specific examples, Rx represents H, $CH_3$, $CH_2OH$, and $CF_3$.

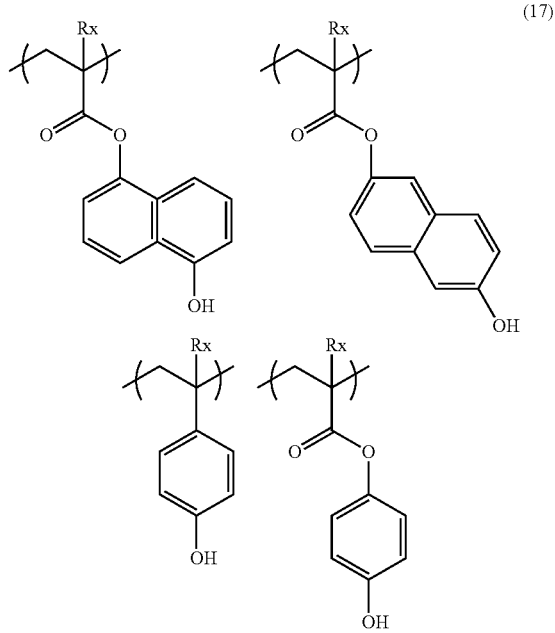

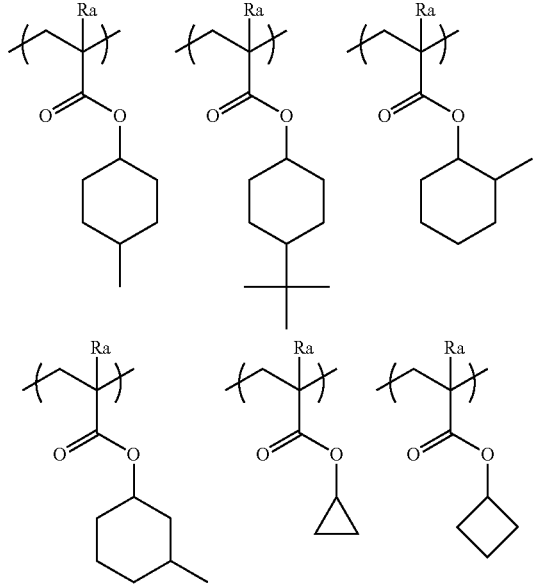

(17)

The resin (A) may further include an alicyclic hydrocarbon structure and/or an aromatic ring structure that does not include a polar group (for example, the acid group, a hydroxyl group, and a cyano group), and may have a repeating unit that does not represent acid decomposable properties.

The resin (A) may not have the repeating unit, but, if resin (A) has the repeating unit, the content thereof is preferably in the range of 2% by mol to 40% by mol, and more preferably in the range of 5% by mol to 30% by mol with respect to the total repeating units of the resin (A).

Specific examples of a repeating unit which has an alicyclic hydrocarbon structure without a polar group and which does not have acid decomposable properties are described below, but the invention is not limited thereto. In the formulae, Ra represents H, $CH_3$, $CH_2OH$, or $CF_3$.

(18)

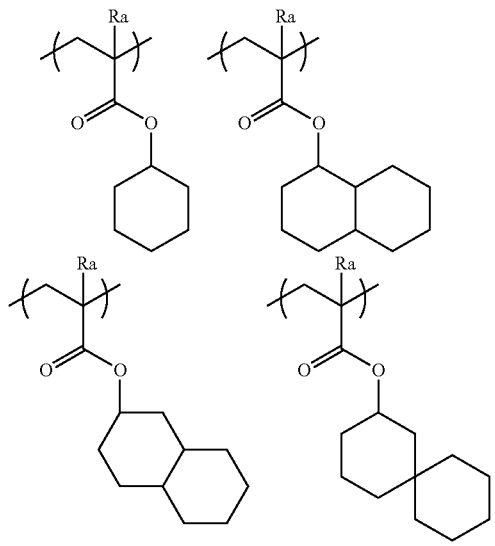

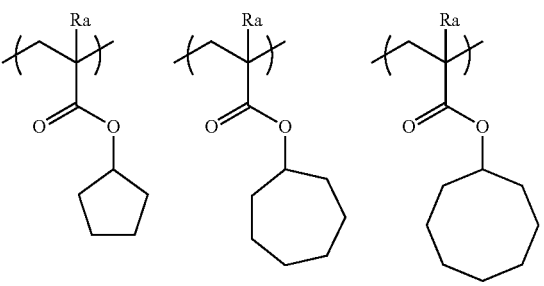

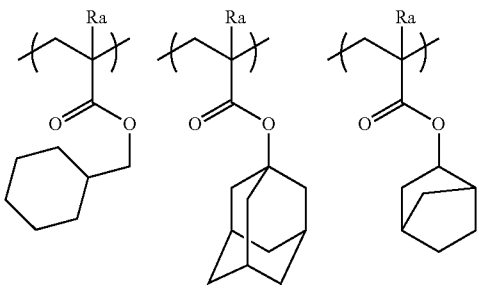

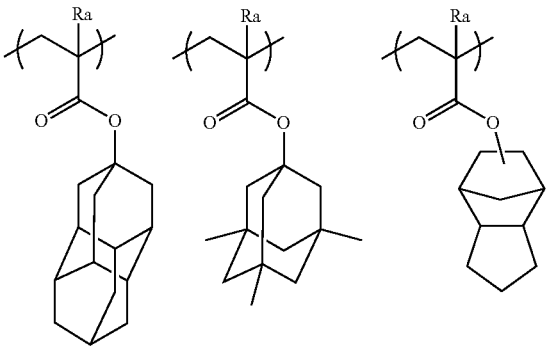

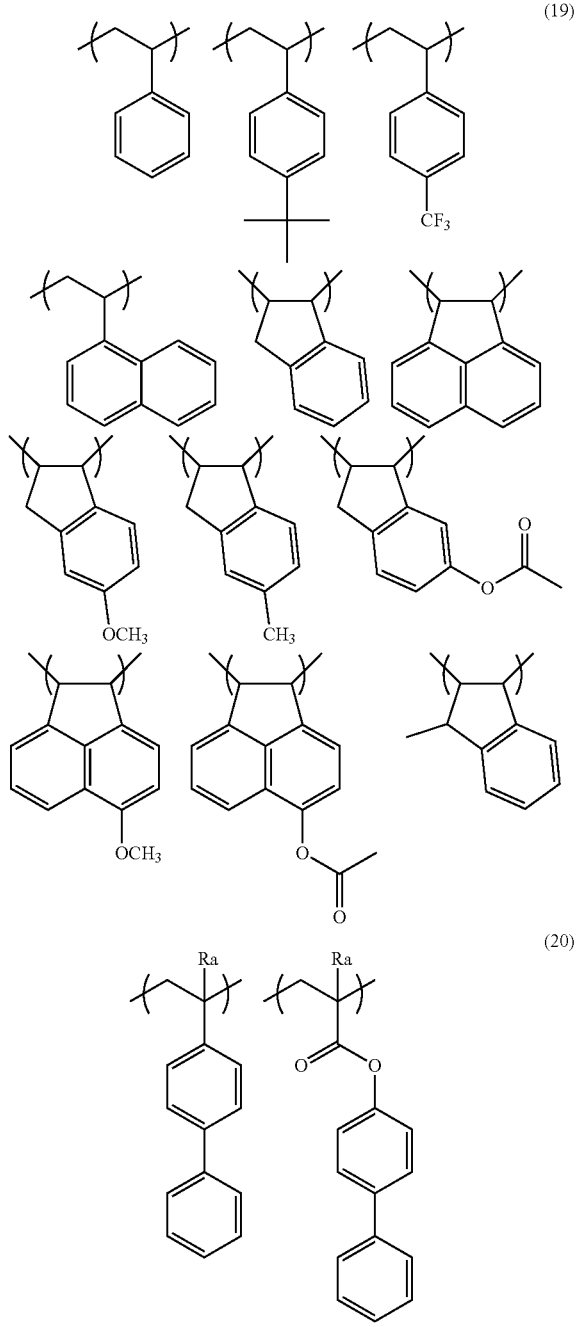

If the composition according to the invention is used for the ArF exposure, in view of the transparency to the ArF ray, it is preferable that the resin (A) used in the composition according to the invention does not substantially have an aromatic ring (specifically, in the resin, the ratio of the repeating unit having an aromatic group is preferably 5% by mol or lower, more preferably 3% by mol or lower, and ideally 0% by mol, that is, an aromatic group is not included), and the resin (A) preferably has a monocyclic or a polycyclic alicyclic hydrocarbon structure.

The formation of the resin (A) according to the invention may be any one of a random shape, a block shape, a comb shape, and a star shape. For example, the resin (A) can be synthesized by radical, cation, or anion polymerization of an unsaturated monomer corresponding to each structure. In addition, after the polymerization is performed by using an unsaturated monomer corresponding to a precursor of each structure, a polymer reaction is performed such that an objective resin can be obtained.

If the composition according to the invention is used for the ArF exposure, in view of the transparency to the ArF ray, it is preferable that the resin (A) used in the composition according to the invention does not substantially have an aromatic ring (specifically, in the resin, the ratio of the repeating unit having an aromatic group is preferably 5% by mol or lower, more preferably 3% by mol or lower, and ideally 0% by mol, that is, an aromatic group is not included), and the resin (A) preferably has a monocyclic or a polycyclic alicyclic hydrocarbon structure.

If the composition according to the invention includes a resin (D) described below, in view of the compatibility with the resin (D), it is preferable that the resin (A) does not contain a fluorine atom and a silicon atom.

As the resin (A) used in the composition according to the invention, it is preferable that all repeating units are configured with (meth)acrylate-based repeating units. In this case, any one of the resins of which all the repeating units are methacrylate-based repeating units, of which all the repeating units are acrylate-based repeating units, or of which all the repeating units are methacrylate-based repeating units and acrylate-based repeating units can be used, but the resin of which acrylate-based repeating units are 50% by mol or lower with respect to all repeating units is preferable.

If the composition according to the invention is irradiated with a KrF excimer laser ray, an electron ray, an X ray, or a high energy light beam (EUV or the like) having a wavelength of 50 nm or lower, the resin (A) may include a repeating unit having an aromatic ring. The repeating unit having an aromatic ring is not particularly limited, and, as exemplified in the description relating to the respective repeating units described above, a styrene unit, a hydroxystyrene unit, a phenyl (meth)acrylate unit, a hydroxyphenyl (meth)acrylate unit, and the like are included. As the resin (A), more specifically, a resin having a hydroxystyrene-based repeating unit and a hydroxystyrene-based repeating unit protected by an acid-decomposable group, a resin having a repeating unit having an aromatic ring and a repeating unit in which a carboxylic acid position of (meth) acrylic acid is protected by an acid-decomposable group, and the like are included.

The resin (A) according to the invention can be synthesized or refined by a usual method (for example, radical polymerization). As the synthesization method and the refinement method, for example, the description in paragraphs 0201 and 0202 of JP2008-292975A may be referred to.

The weight average molecular weight of the resin (A) according to the invention is 7,000 or greater as described above, preferably in the range of 7,000 to 200,000, more preferably in the range of 7,000 to 50,000, still more preferably in the range of 7,000 to 40,000, and particularly preferably in the range of 7,000 to 30,000, in terms of polystyrene according to a GPC method. If the weight average molecular weight is smaller than 7,000, the solubility in the organic developer becomes too high, and there is a concern that thus a precise pattern may not be formed.

The dispersion degree (molecular weight distribution) is generally in the range of 1.0 to 3.0, preferably in the range of 1.0 to 2.6, more preferably in the range of 1.0 to 2.0, and particularly preferably in the range of 1.4 to 2.0. As the molecular weight distribution is smaller, a resolution and a resist shape are excellent, a sidewall of a resist pattern is smooth, and roughness properties are excellent.

In the chemical amplification type resist composition according to the invention, a compounding ratio of the resin (A) to the total composition is preferably in the range of 30% by mass to 99% by mass and more preferably in the range of 60% by mass to 95% by mass in the total solid content.

In addition, according to the invention, the resin (A) may be used singly, or two or more types thereof may be used in combination.

Hereinafter, specific examples (a composition ratio of a repeating unit is a molar ratio) of the resin (A) are included, but the invention is not limited thereto. In addition, hereinafter, an embodiment in a case where the structure corresponding to an acid generating agent (B) is carried in the resin (A) is exemplified.

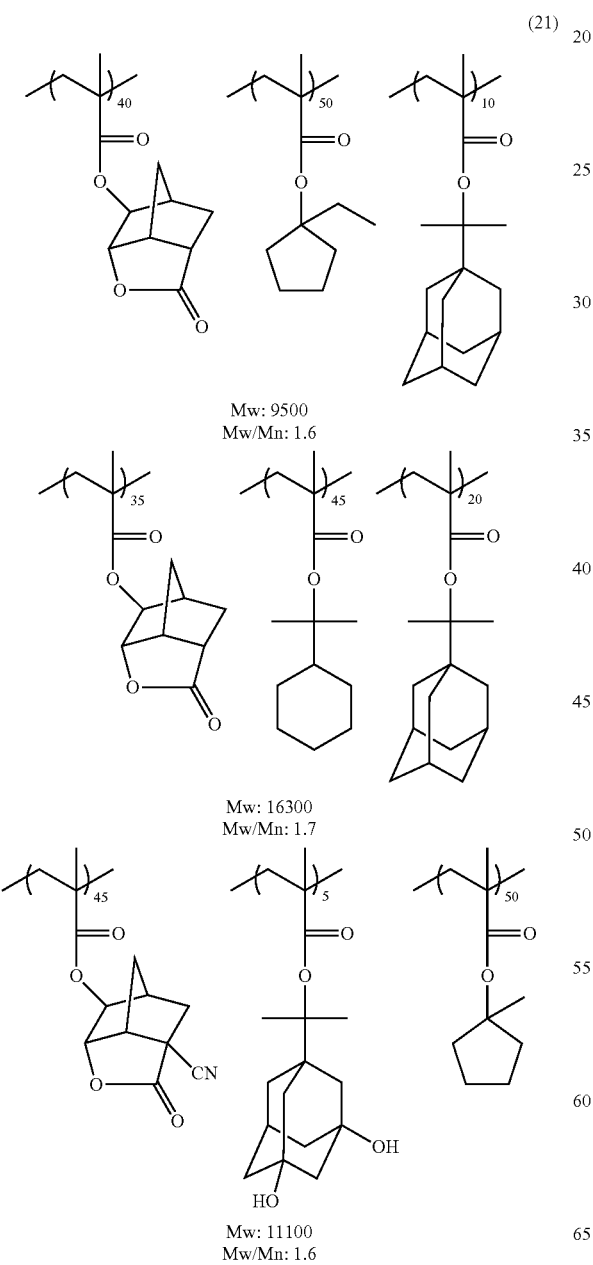

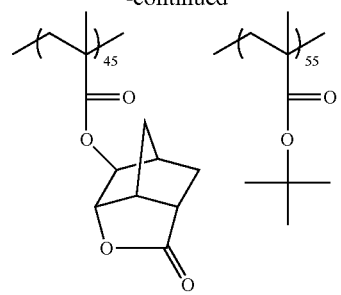

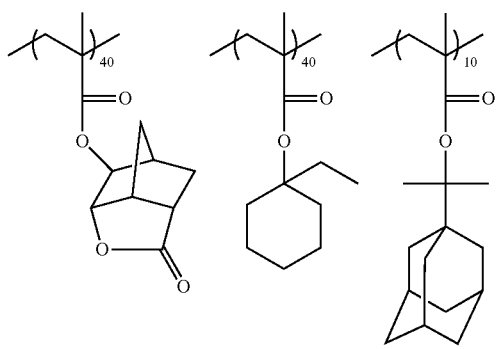

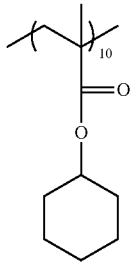

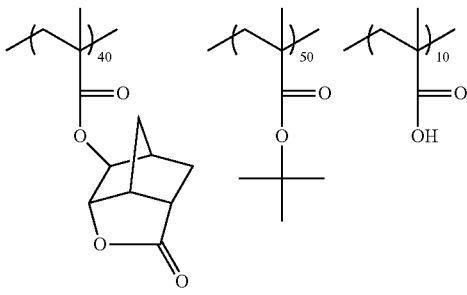

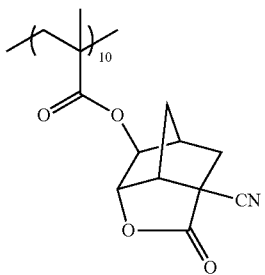

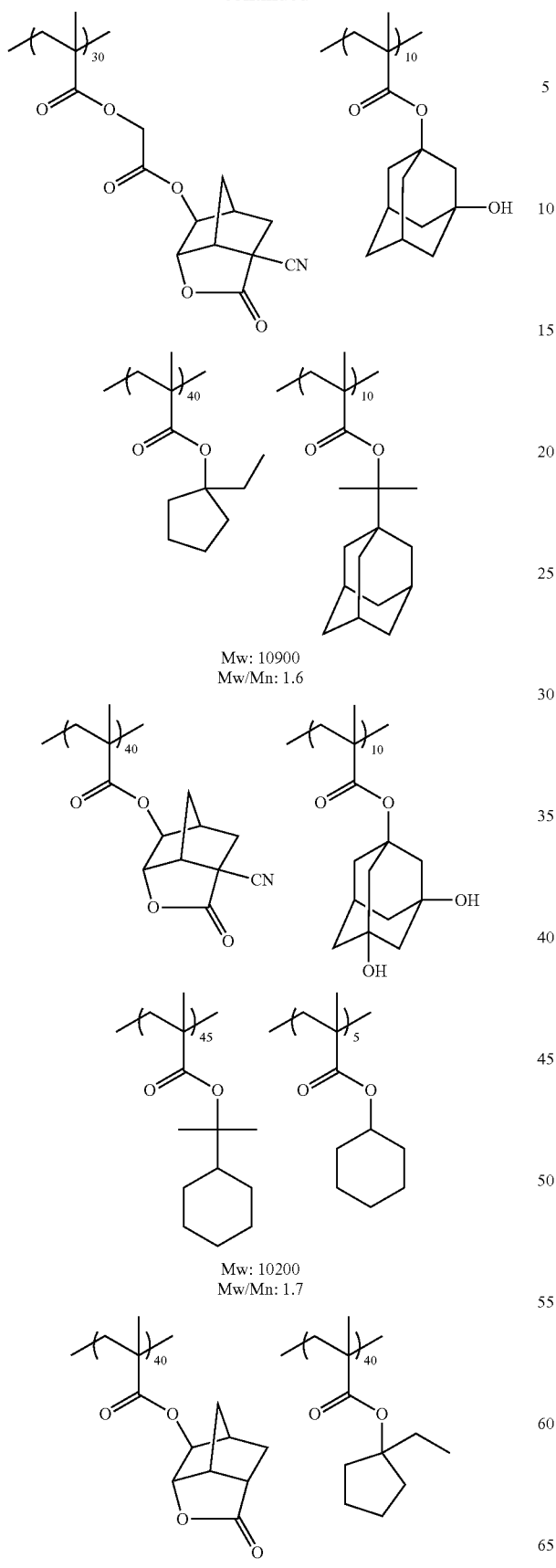
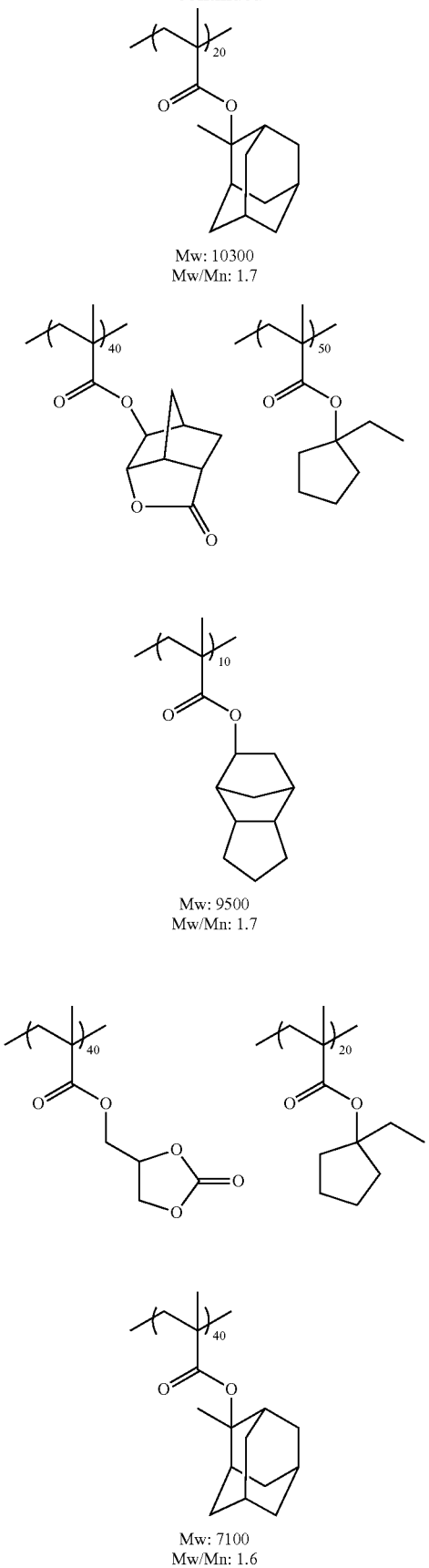

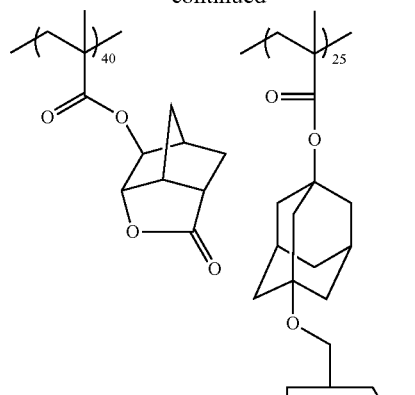
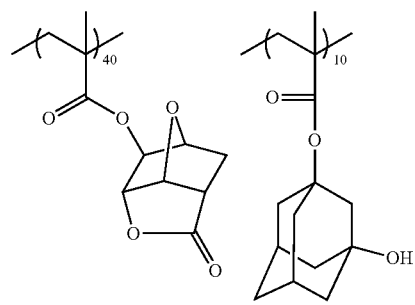
Mw: 6800
Mw/Mn: 1.6
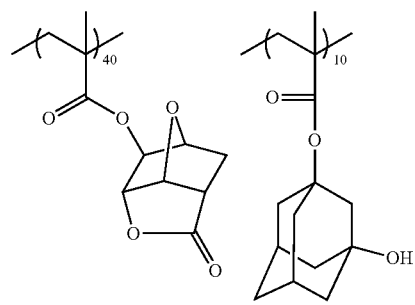
Mw: 10800
Mw/Mn: 1.7
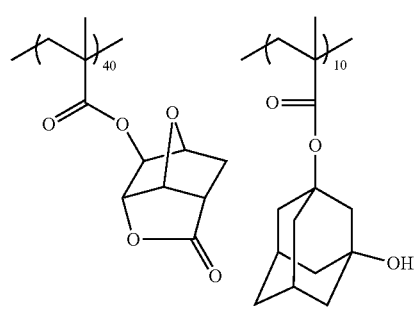
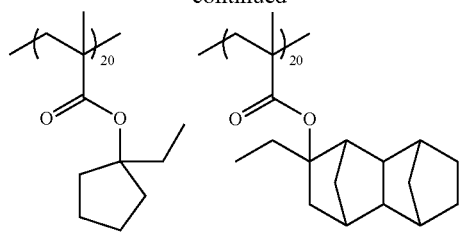
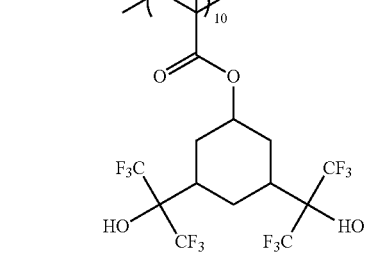
Mw: 9600
Mw/Mn: 1.7
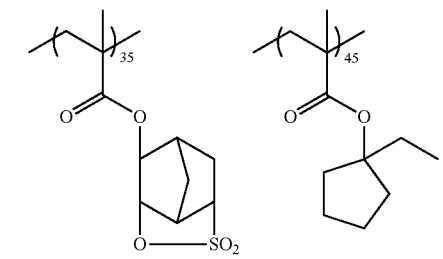
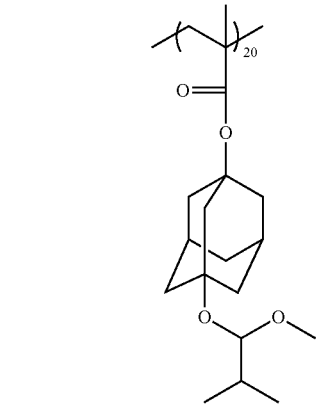
Mw: 10500
Mw/Mn: 1.6
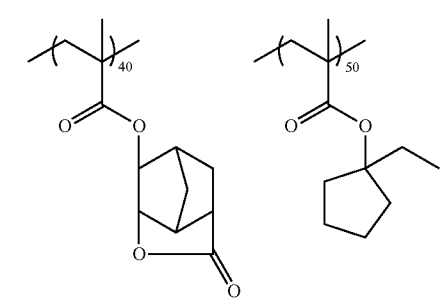

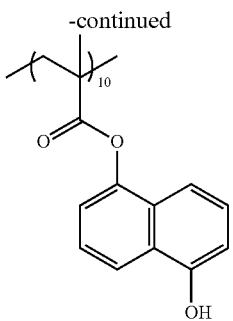
Mw: 8900
Mw/Mn: 1.7
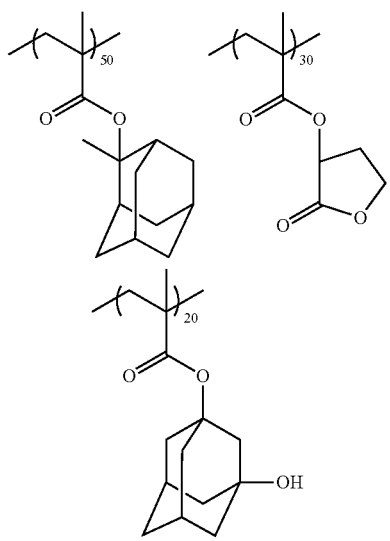
Mw: 11000
Mw/Mn: 1.7
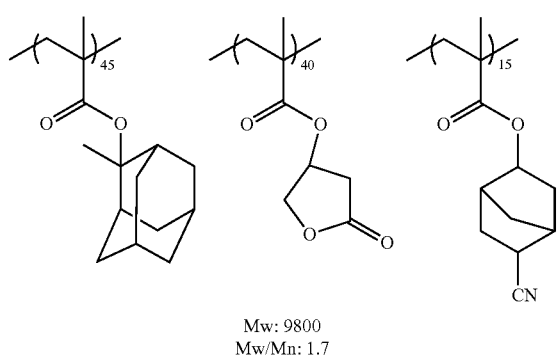
Mw: 9800
Mw/Mn: 1.7
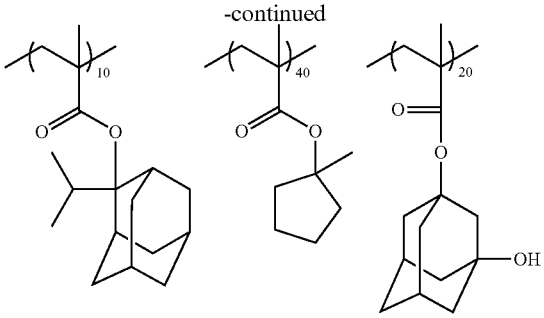
Mw: 11200
Mw/Mn: 1.6
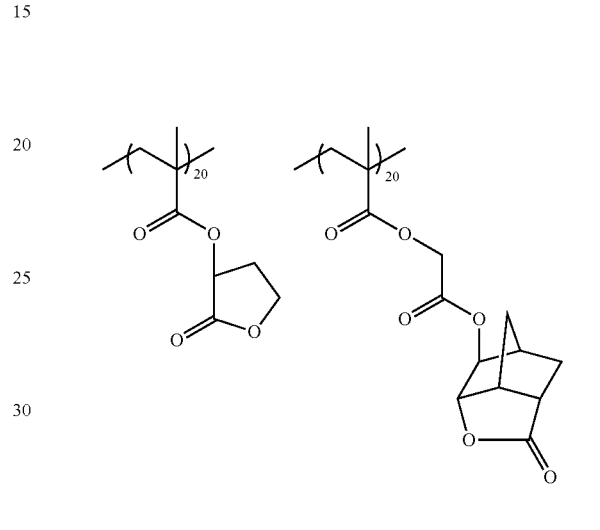
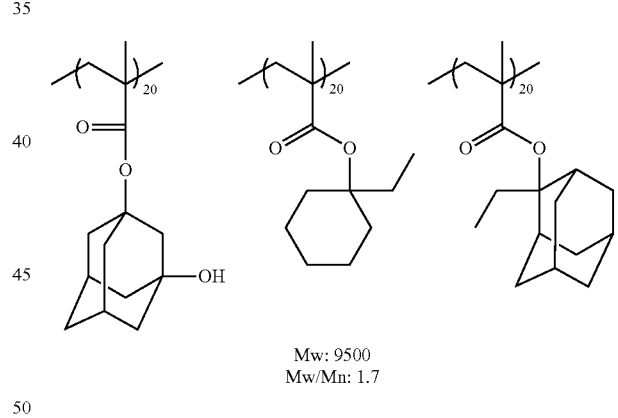
Mw: 9500
Mw/Mn: 1.7
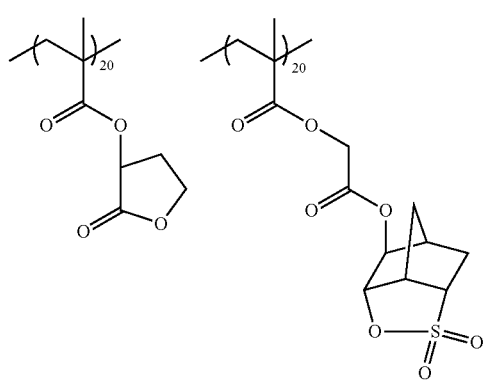
Resins exemplified below are examples of resins that can be appropriately used particularly at the time of the EUV exposure or the electron ray exposure.
(24)
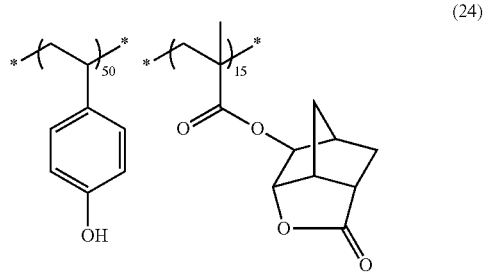

-continued
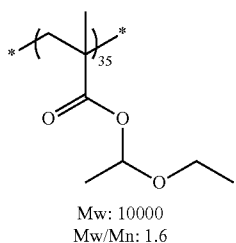
Mw: 10000
Mw/Mn: 1.6
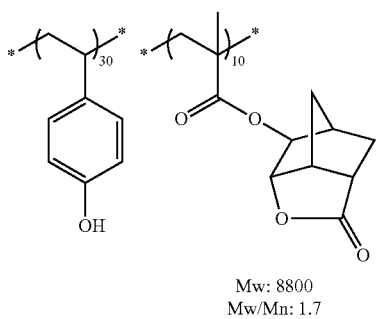
Mw: 8800
Mw/Mn: 1.7
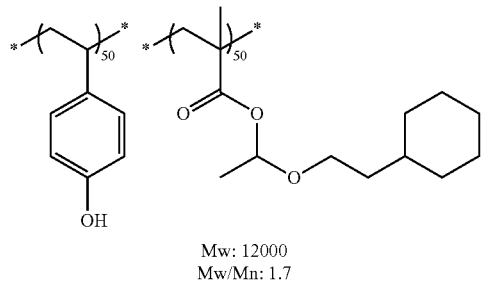
Mw: 12000
Mw/Mn: 1.7
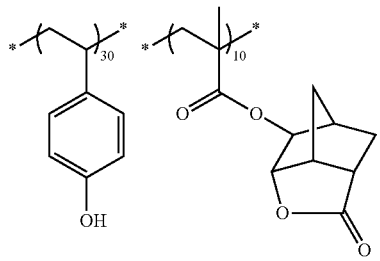
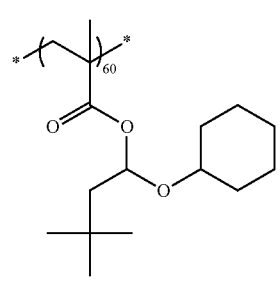
Mw: 20000
Mw/Mn: 1.7
-continued
(25)
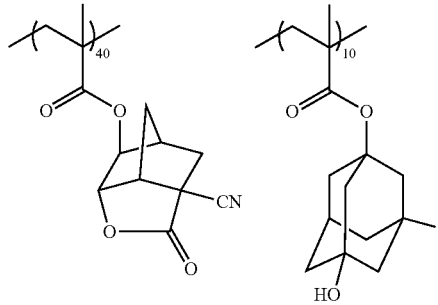
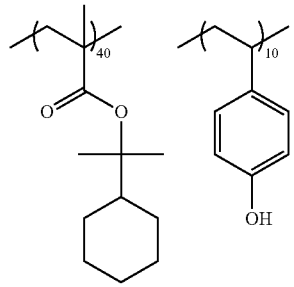
Mw: 10000
Mw/Mn: 1.60
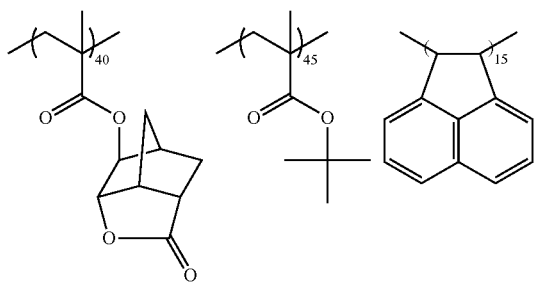
Mw: 7500
Mw/Mn: 1.50
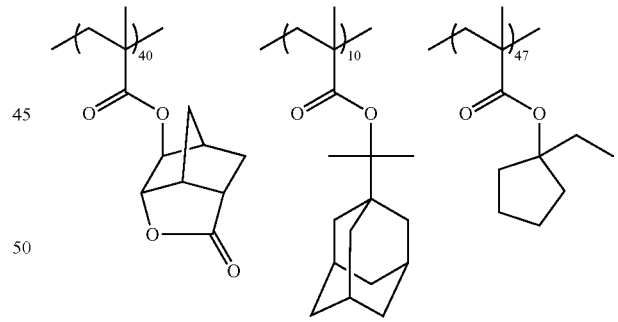
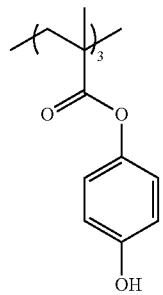
Mw: 11000
Mw/Mn: 1.85

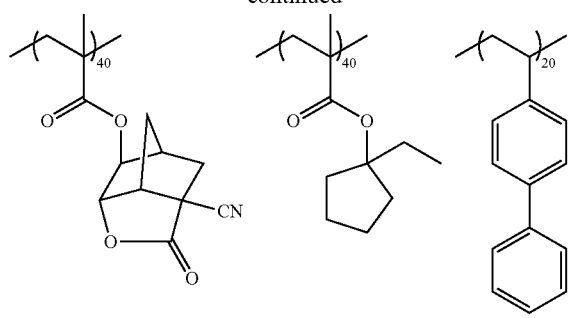
Mw: 7000
Mw/Mn: 1.65
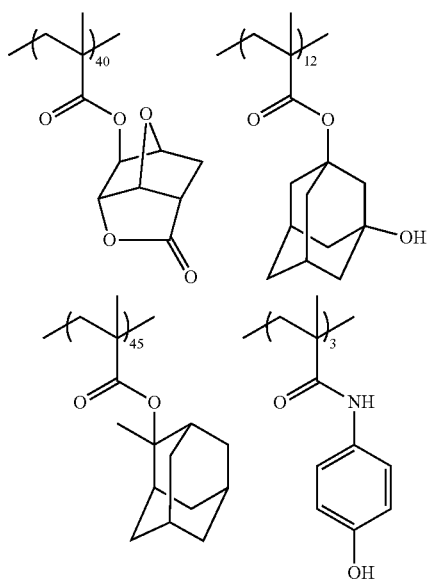
Mw: 8000
Mw/Mn: 1.65
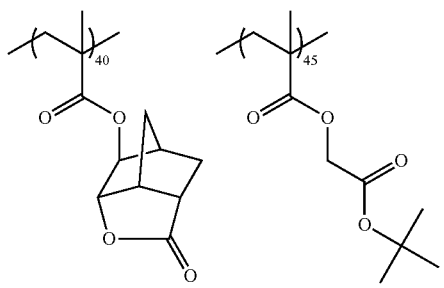
Mw: 19000
Mw/Mn: 1.70
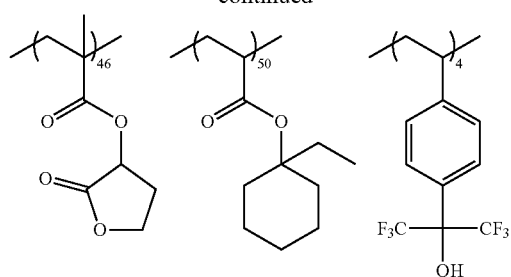
Mw: 26000
Mw/Mn: 1.85
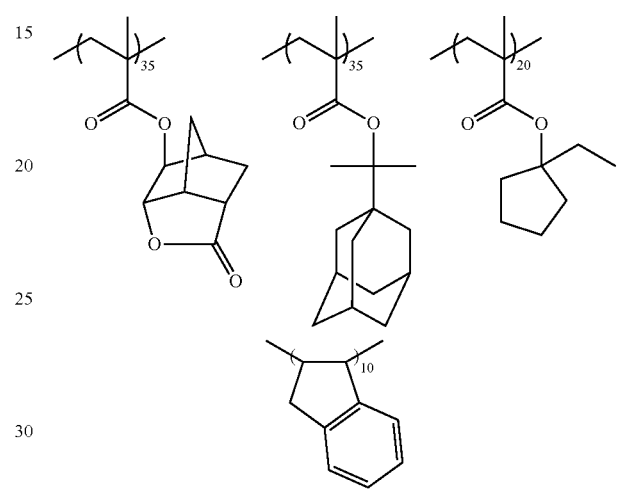
Mw: 21000
Mw/Mn: 1.60
(26)
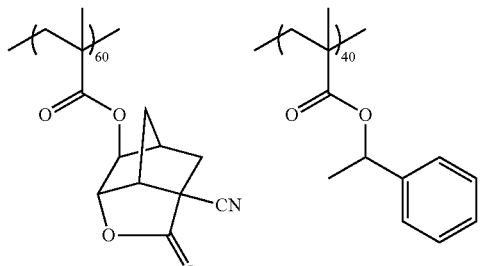
Mw: 6500
Mw/Mn: 1.50
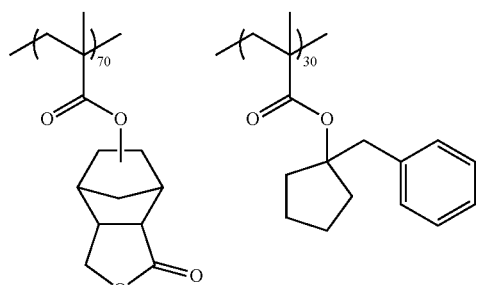
Mw: 8000
Mw/Mn: 1.85

77
-continued
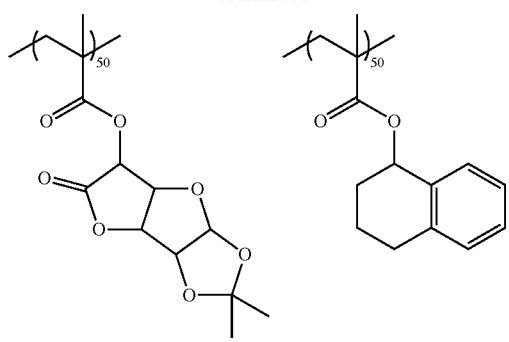
Mw: 28500
Mw/Mn: 1.55
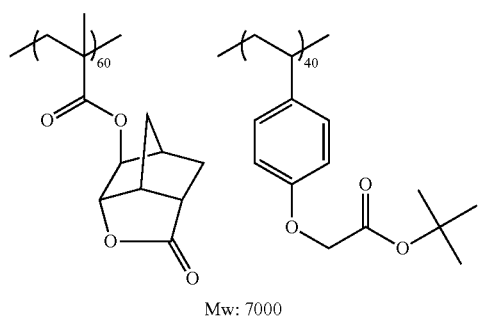
Mw: 7000
Mw/Mn: 1.65
(27)
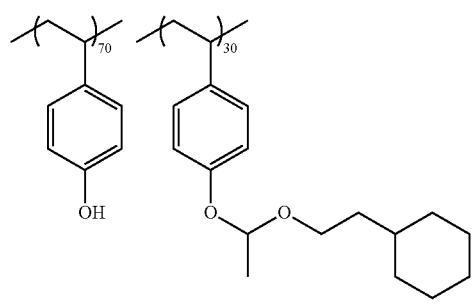
Mw: 15100
Mw/Mn: 1.40
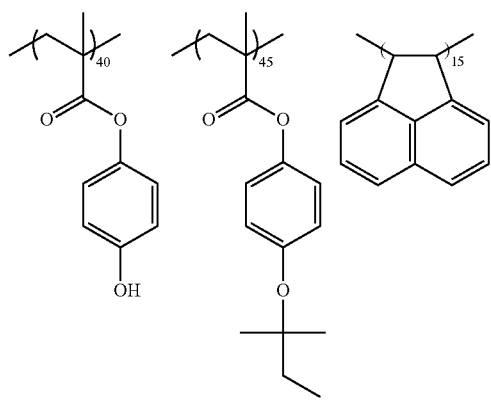
Mw: 8000
Mw/Mn: 1.35
78
-continued
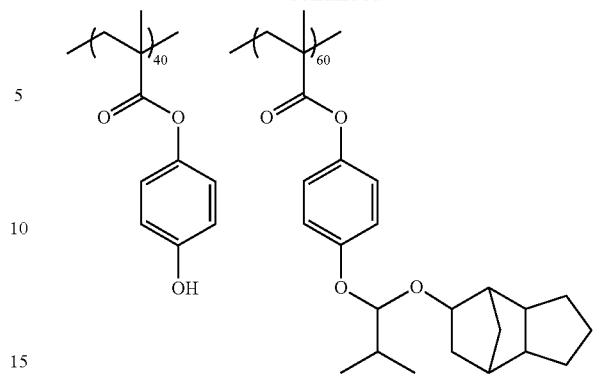
Mw: 9000
Mw/Mn: 1.25
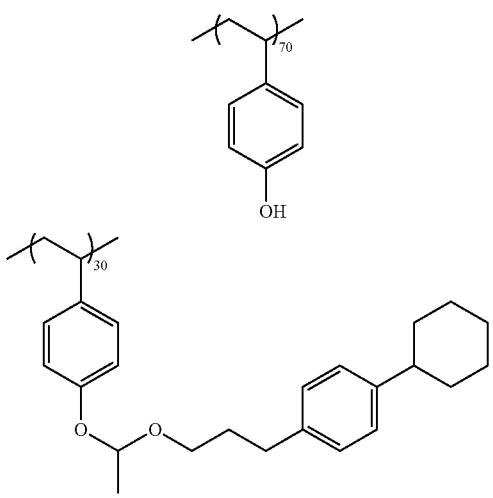
Mw: 4800
Mw/Mn: 1.15
(28)
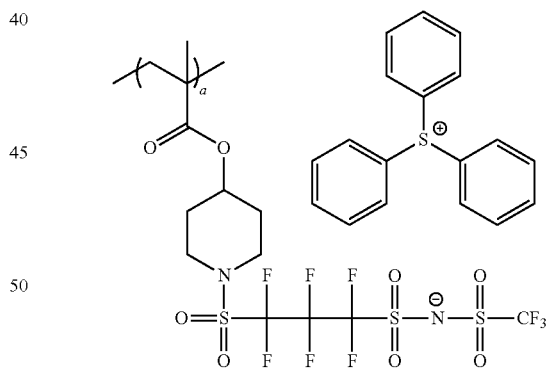
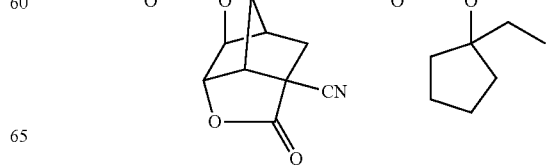

-continued
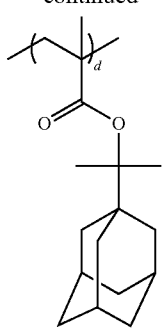
a/b/c/d = 5/43/37/15
Mw = 10500, Mw/Mn = 1.77
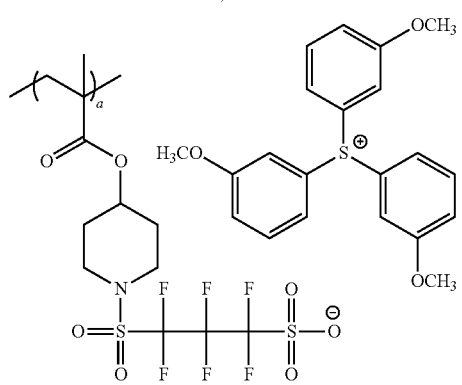
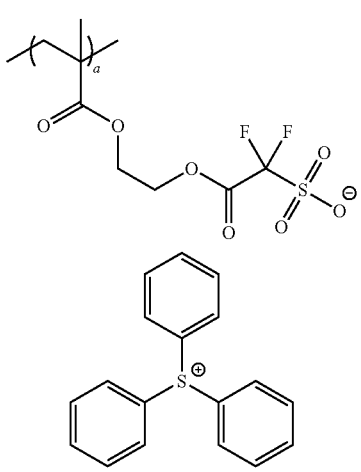
a/b/c = 10/30/60
Mw = 8500, Mw/Mn = 1.78
-continued
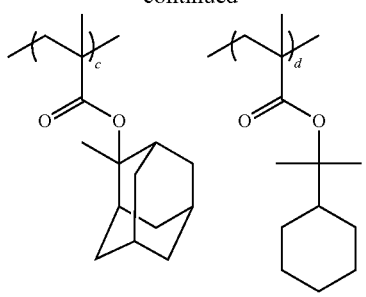
a/b/c/d = 10/40/10/40
Mw = 11500, Mw/Mn = 1.82
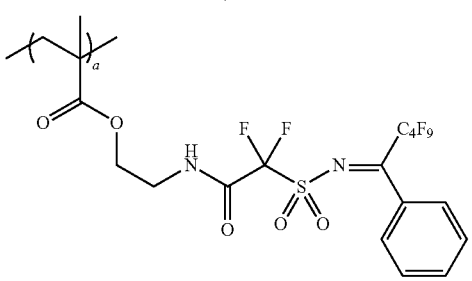
a/b/c = 20/35/45
Mw = 9000, Mw/Mn = 1.68
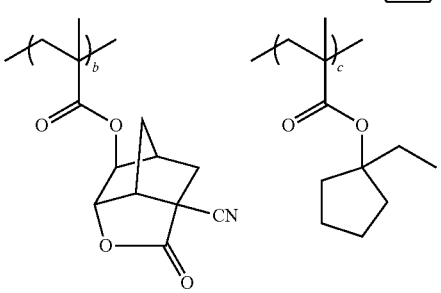
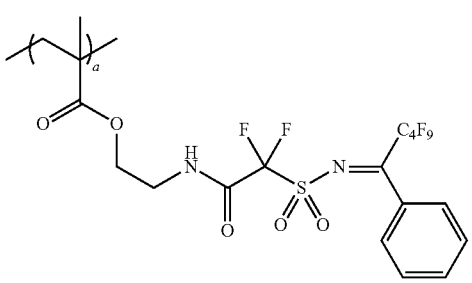
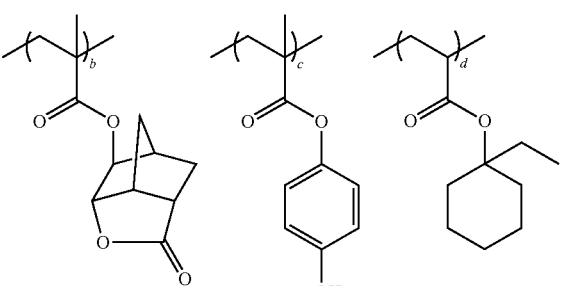
a/b/c/d = 20/15/15/50
Mw = 16000, Mw/Mn = 1.65

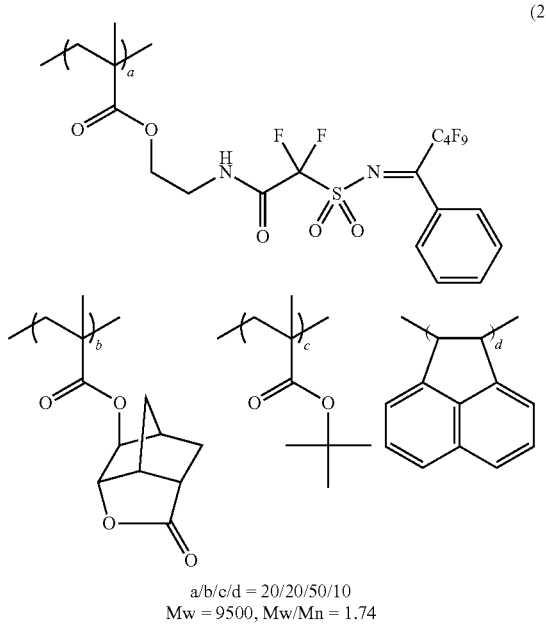
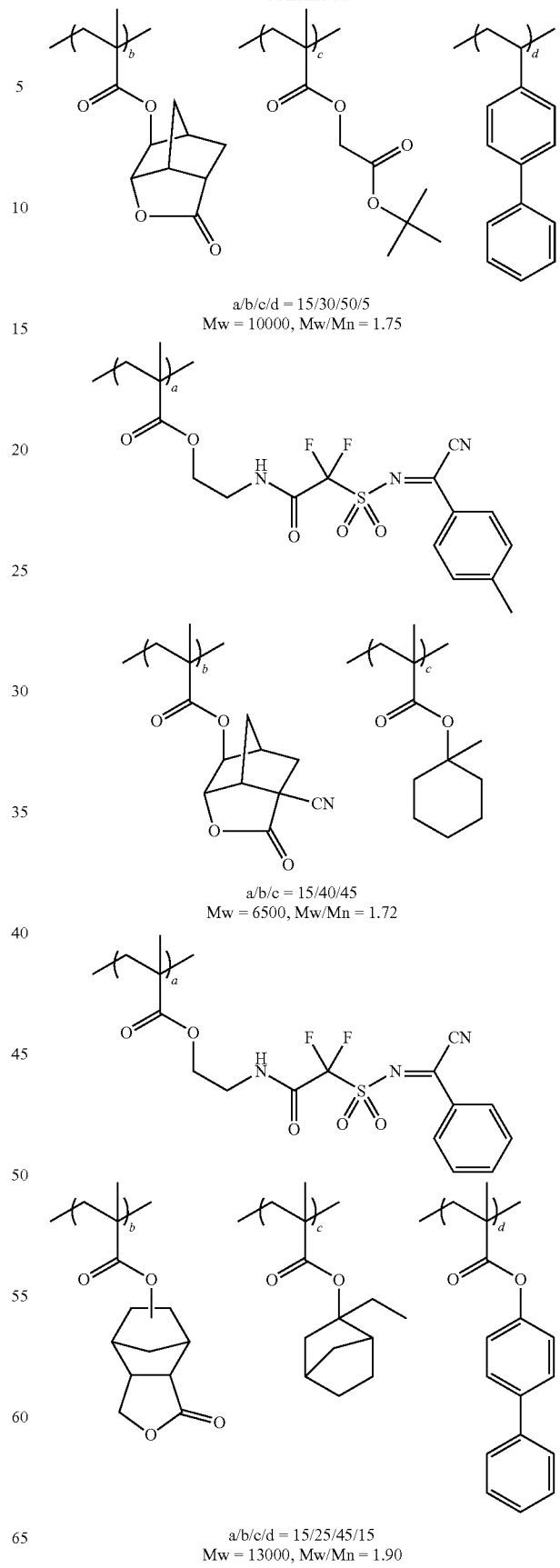

(30)
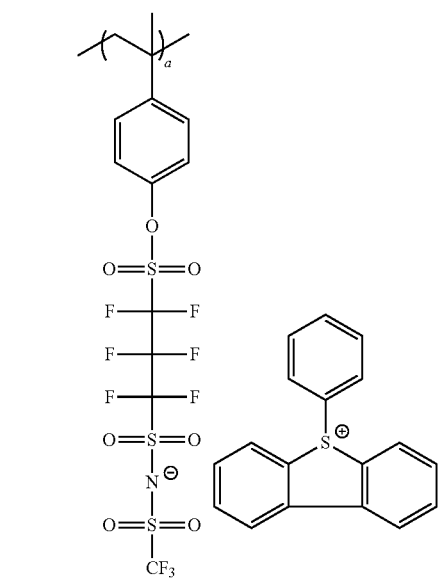
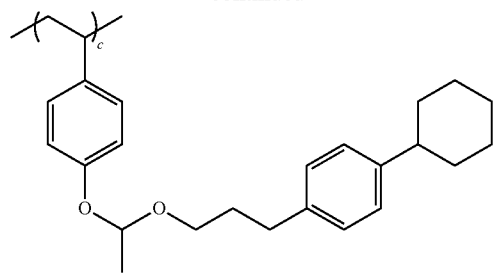
a/b/c = 15/20/65
Mw = 5500, Mw/Mn = 1.15
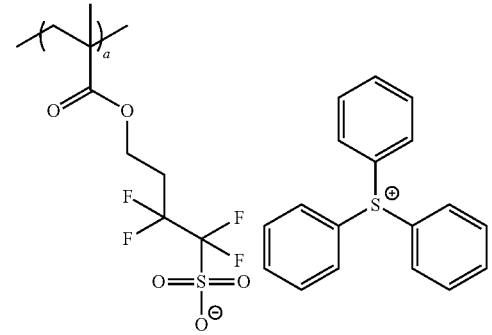
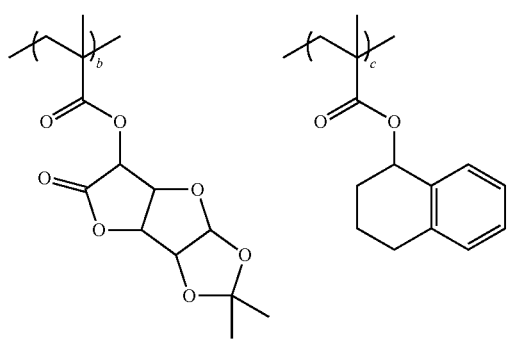
a/b/c = 10/35/55
Mw = 16000
Mw/Mn = 1.80
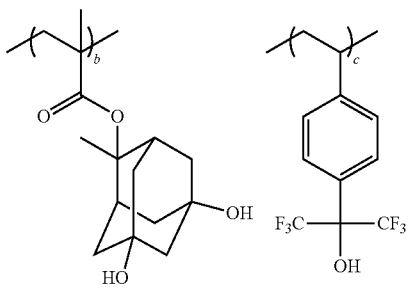
a/b/c/d = 10/30/10/50
Mw = 25000, Mw/Mn = 2.00
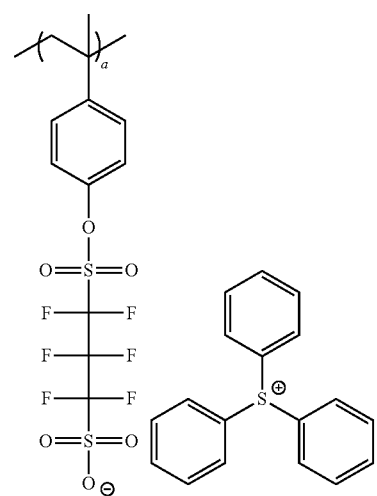
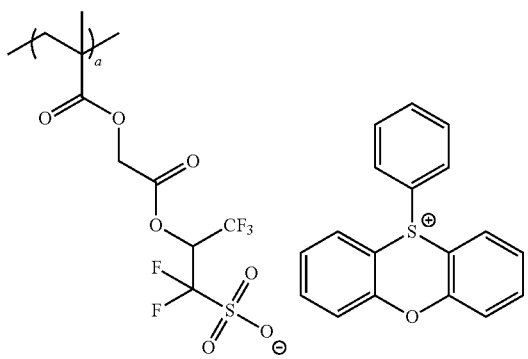

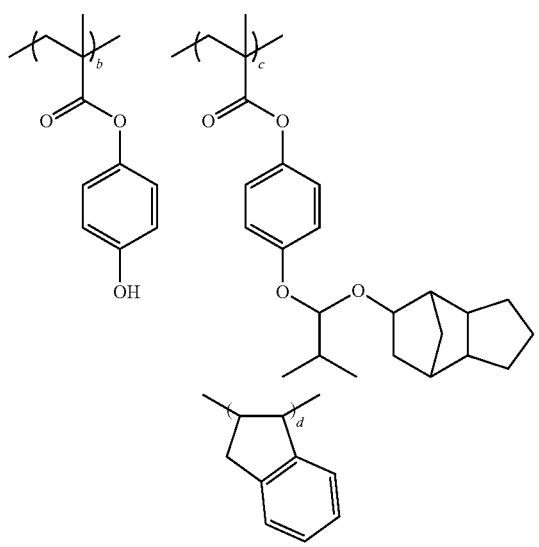
a/b/c/d = 10/25/50/15
Mw = 19000, Mw/Mn = 1.50
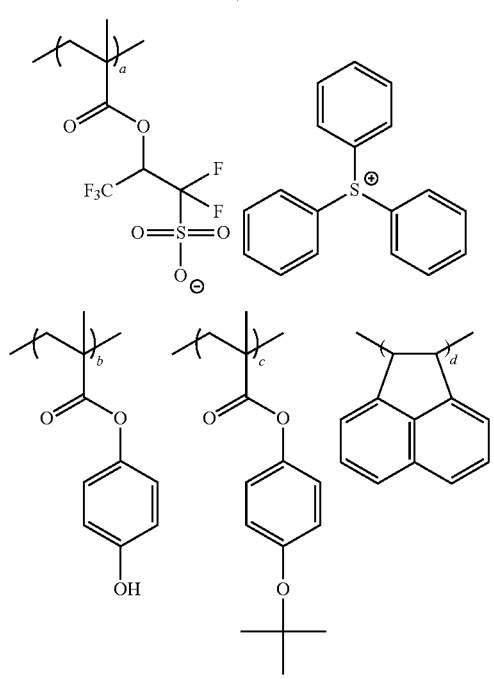
a/b/c/d = 15/15/55/15
Mw = 8500, Mw/Mn = 1.45
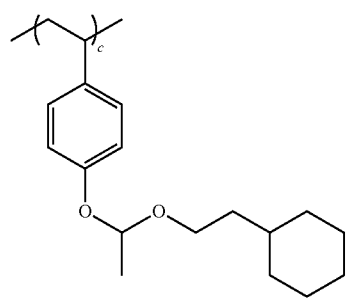
a/b/c = 15/30/55
Mw = 6500, Mw/Mn = 1.40
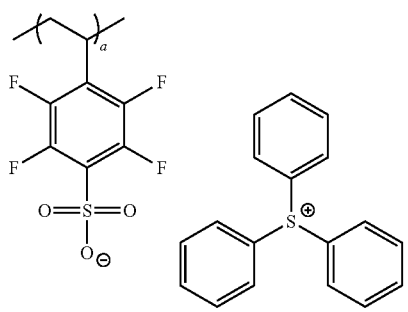
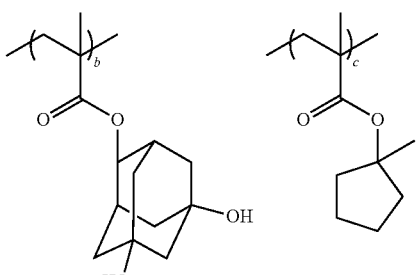
a/b/c = 15/40/45
Mw = 8000, Mw/Mn = 1.50
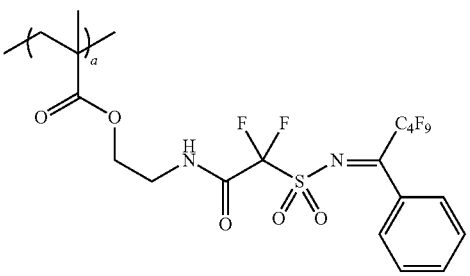
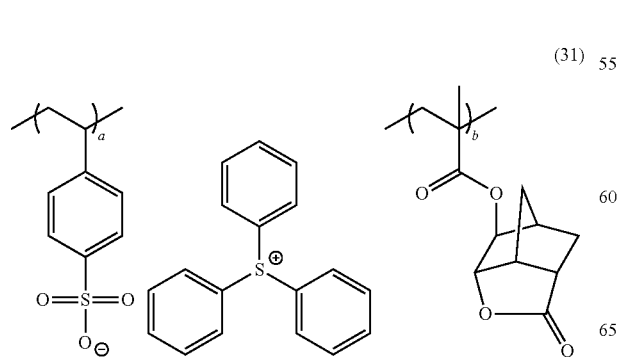
a/b/c = 20/30/50
Mw = 8000, Mw/Mn = 1.75
(31)

-continued

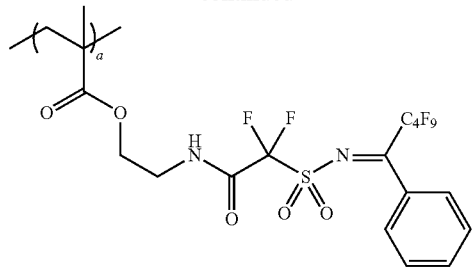
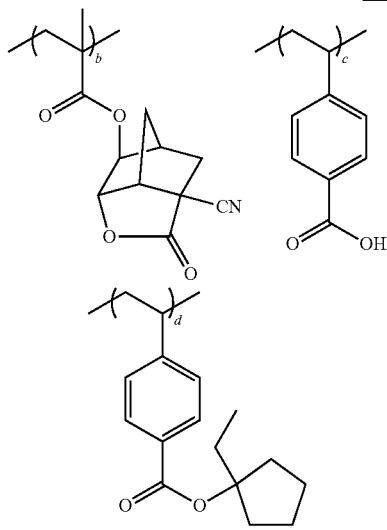
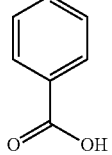

a/b/c/d = 15/25/10/50
Mw = 9000, Mw/Mn = 1.75

[2] (B) Compound that Generates Acid by the Irradiation with an Active Ray or a Radiant Ray The composition according to the invention generally further contains a compound (B) (hereinafter, referred to as "acid generating agent") that generates an acid by the irradiation with an active ray or a radiant ray. The compound (B) that generates acid by the irradiation with the active ray or the radiant ray is preferably a compound that generates an organic acid by the irradiation with the active ray or the radiant ray.

As the acid generating agent, well-known compounds that generate acid by the irradiation with the active ray or the radiant ray that are used in a photoinitiator of photocationic polymerization, a photoinitiator of photoradical polymerization, a light-decoloring agent of pigments, a photochromic agent, micro resist, or the like, and the mixture thereof can be appropriately selected to be used.

For example, diazonium salt, phosphonium salt, sulfonium salt, iodonium salt, imide sulfonate, oxime sulfonate, diazodisulfone, disulfone, and o-nitrobenzyl sulfonate can be included.

Among the acid generating agents, particularly preferable examples are provided below.

(32)

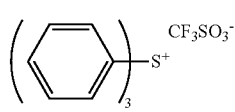
(z1)

-continued

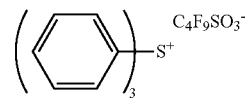
(z2)

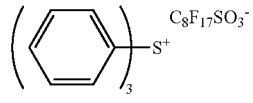
(z3)

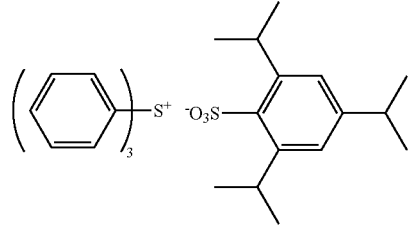
(z4)

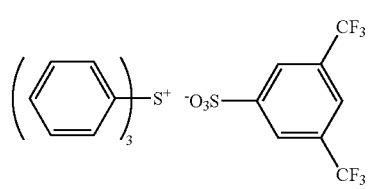
(z5)

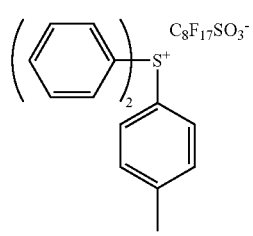
(z6)

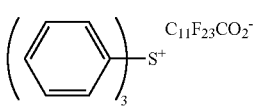
(z7)

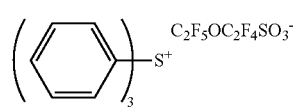
(z8)

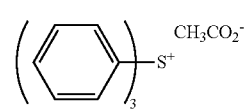
(z9)

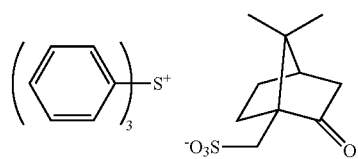
(z10)

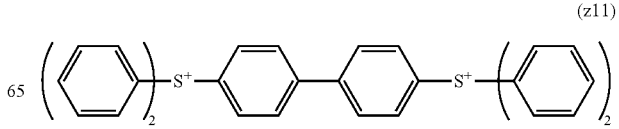
(z11)

-continued
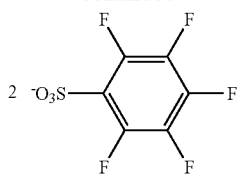
(z11)
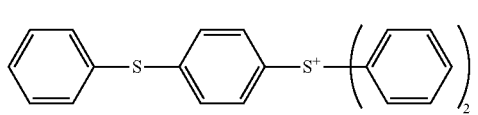
(z12)
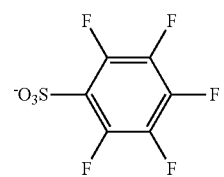
(z13)
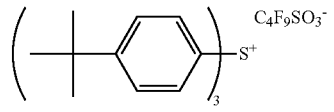
(z14)
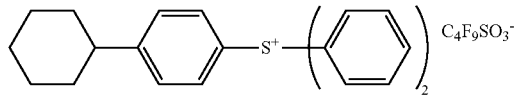
(z15)
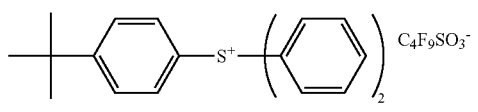
(z16)
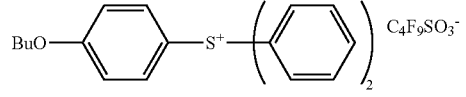
(z17)
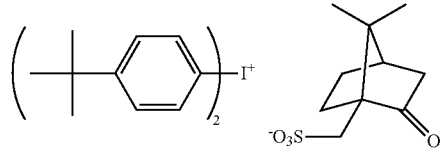
(z18)
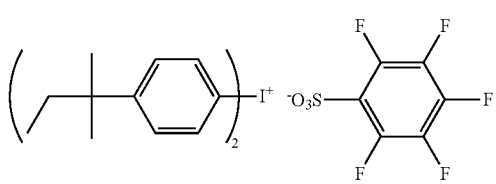
(z19)
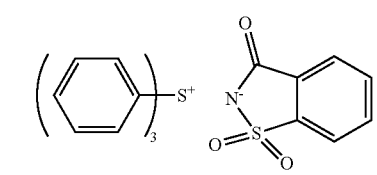
(z20)
-continued
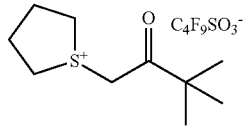
(z21)
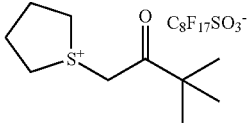
(z22)
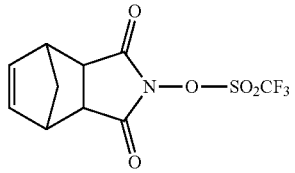
(z23)
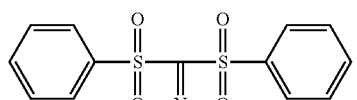
(z24)
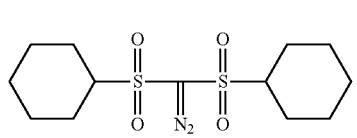
(z25)
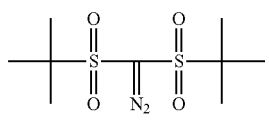
(z26)
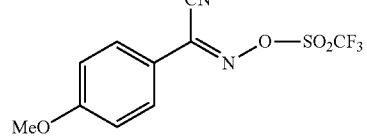
(z27)
(z28)
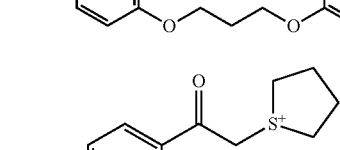
(z29)
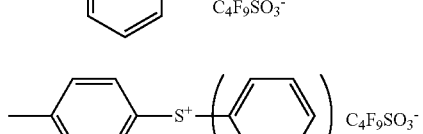
(z30)
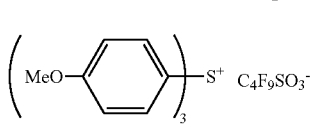
(z31)

-continued

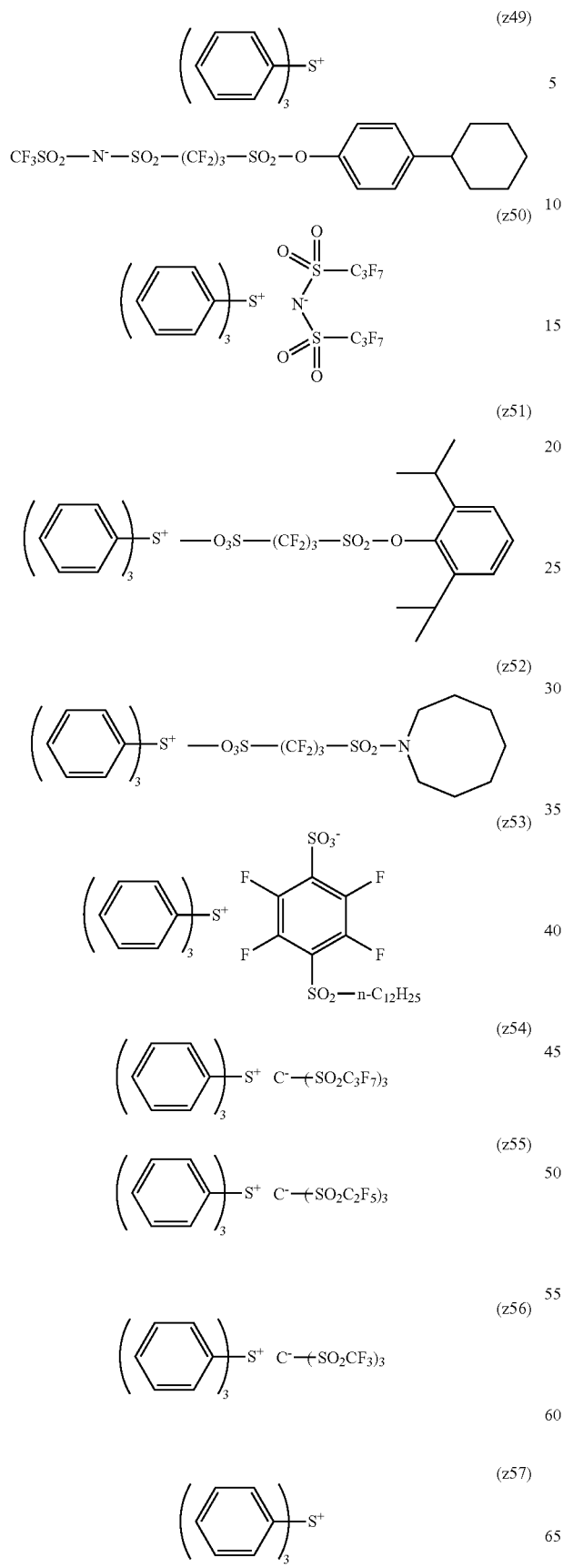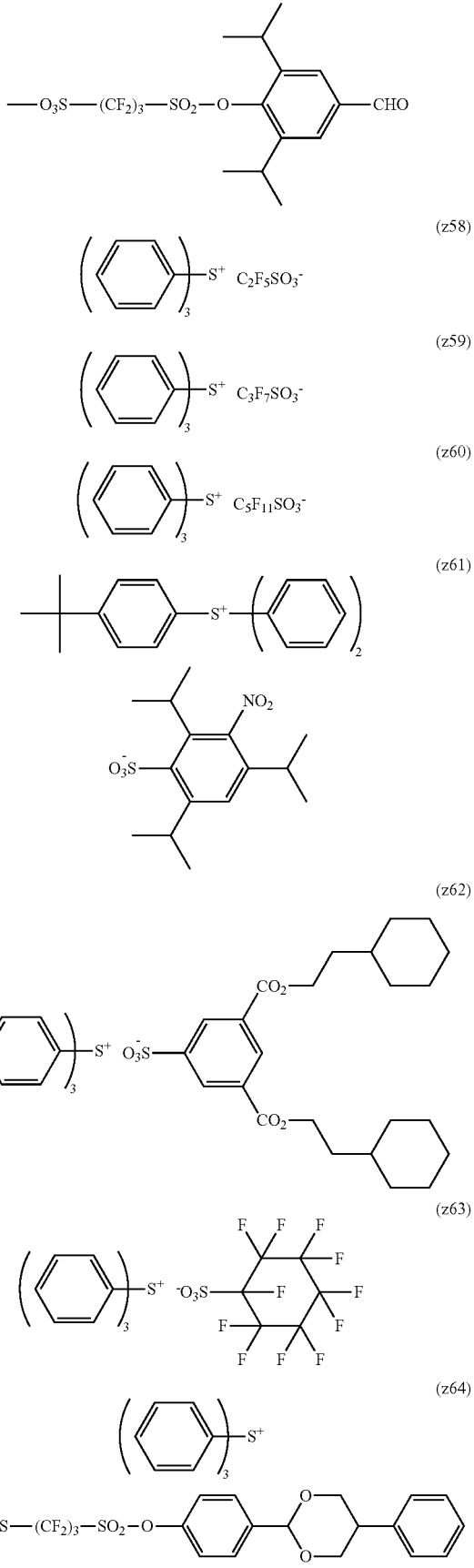

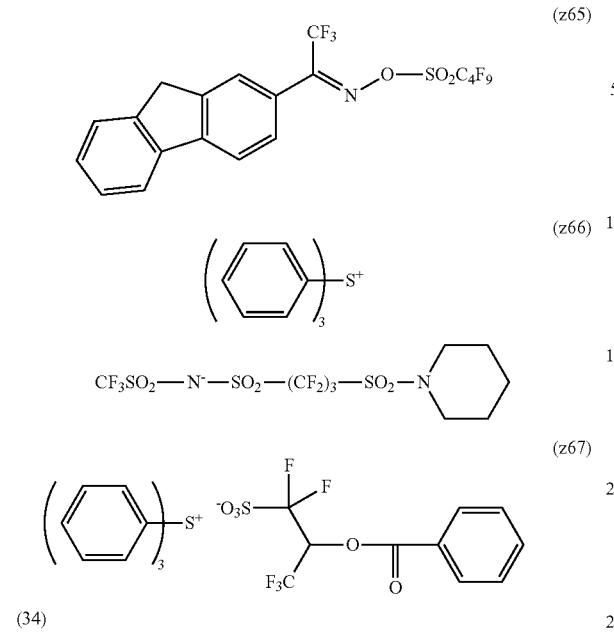
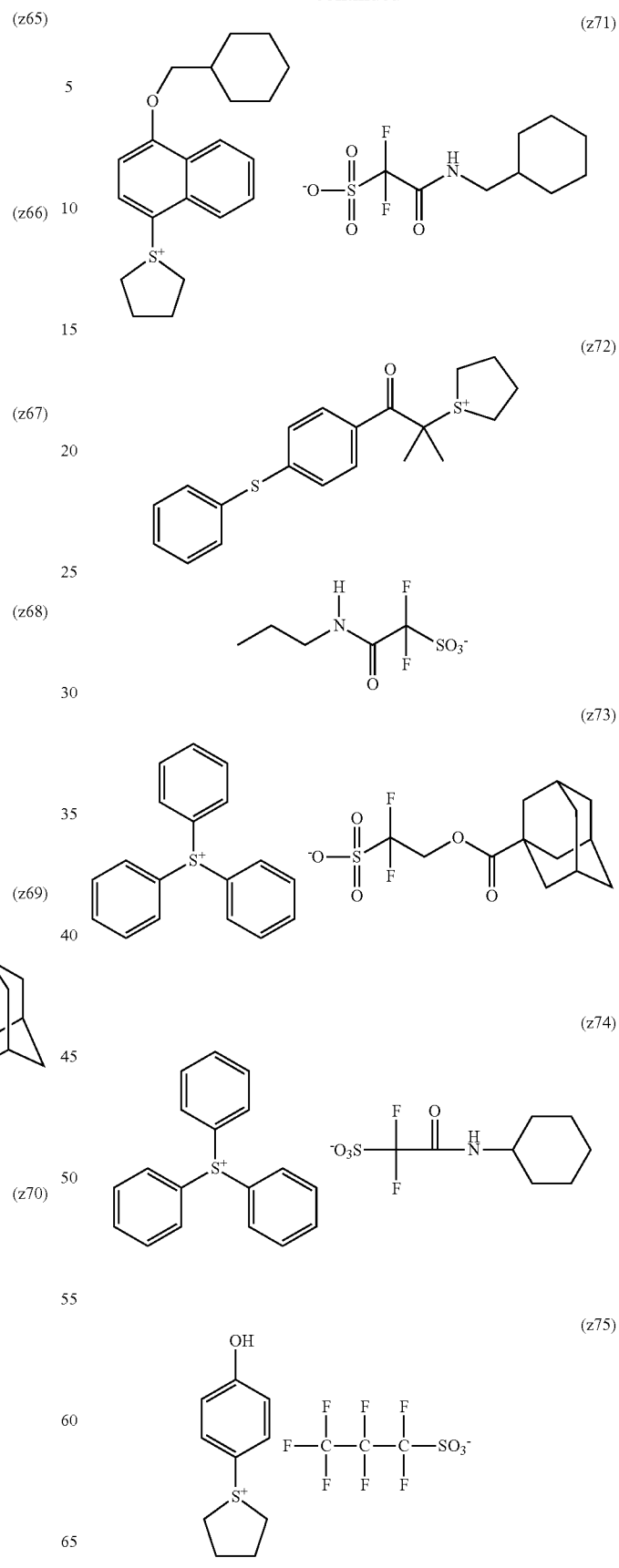

(z76) 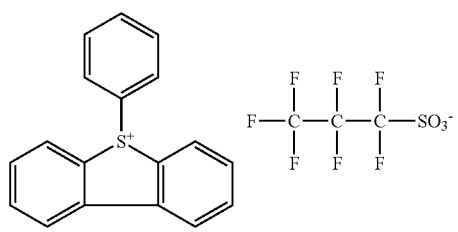
(z77) 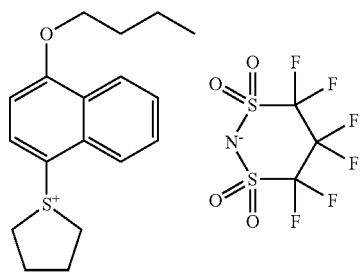
(z78) 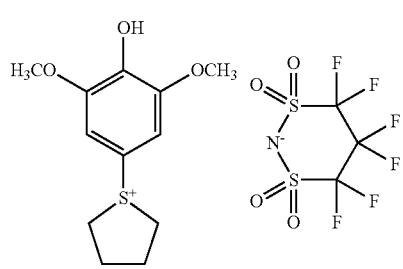
(z79) 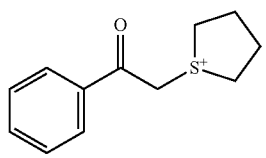
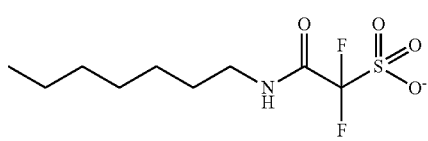
(z80) 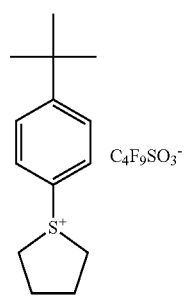
(z81) 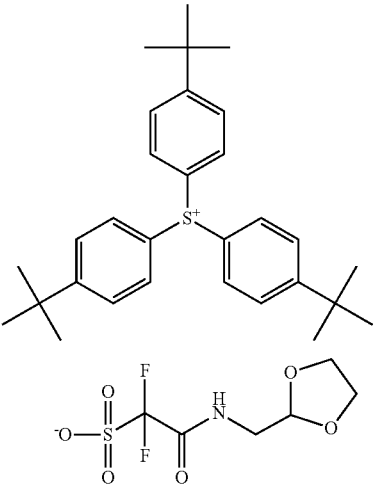
(z82) 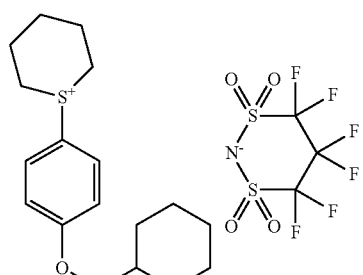
(z83) 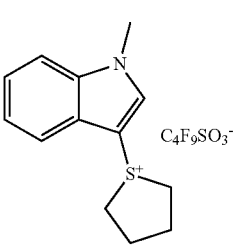
(z84) 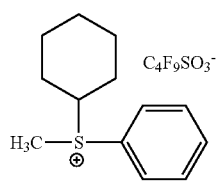
(z85) 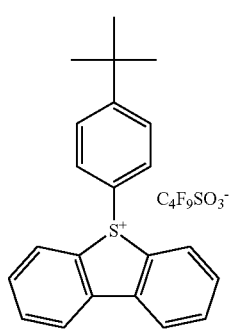

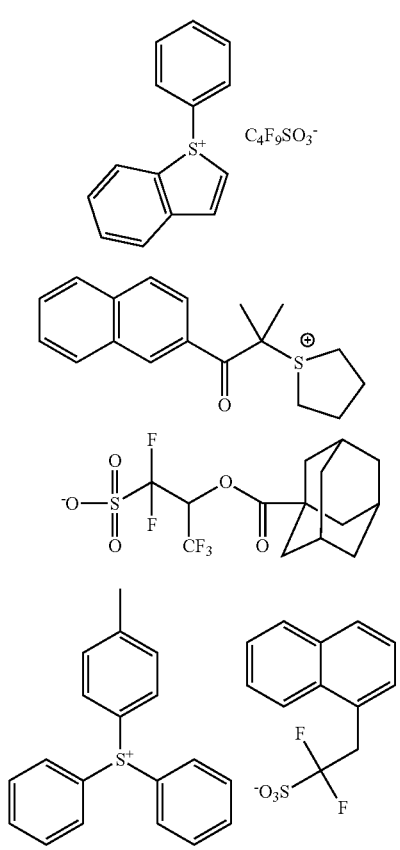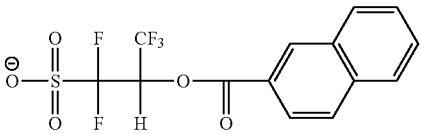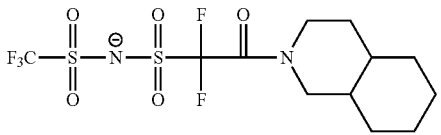

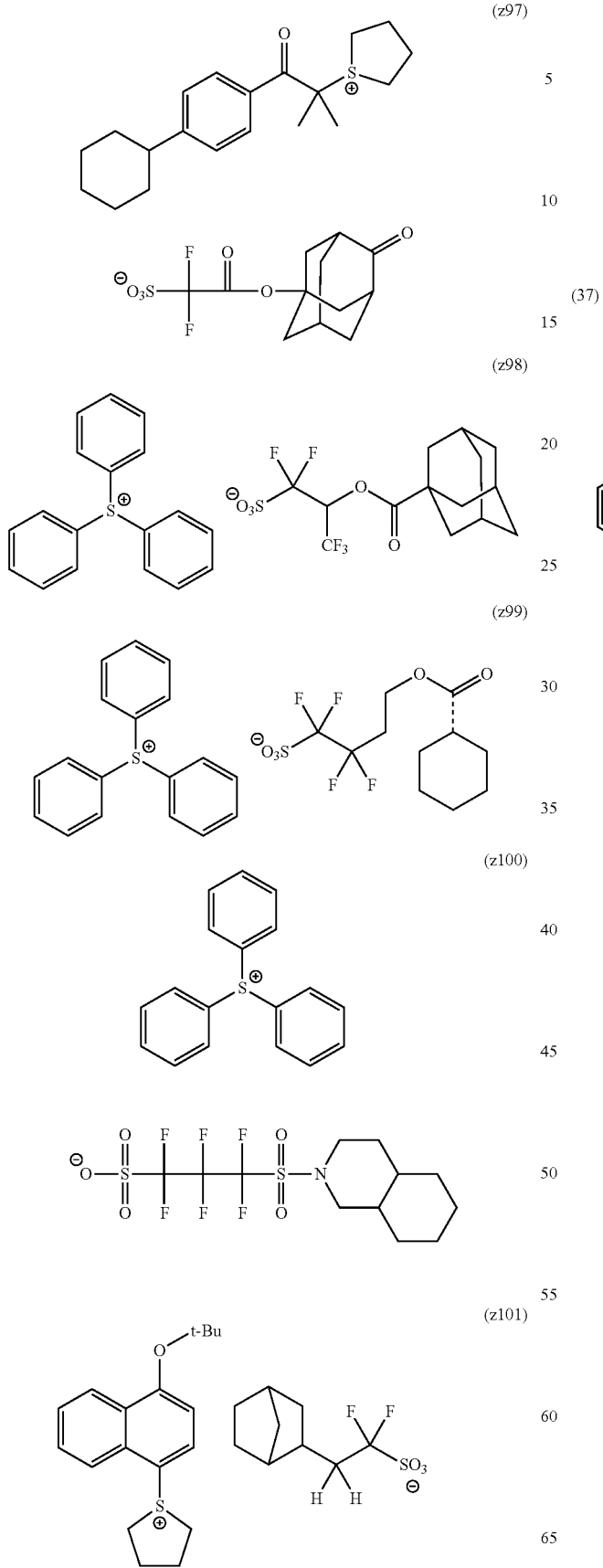

-continued
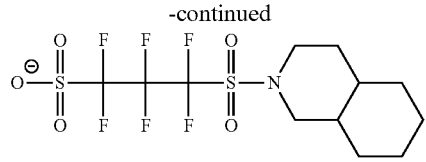
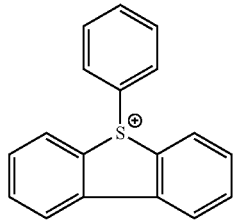
(z107)
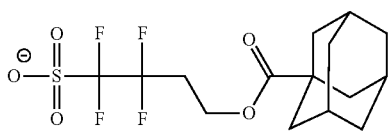
(z108)
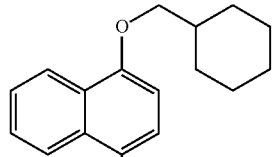
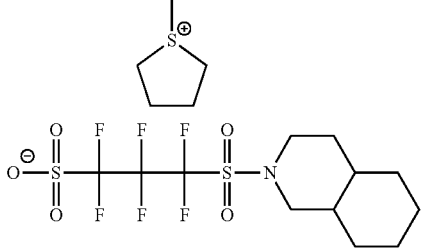
(38)
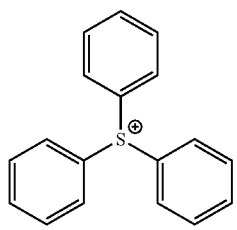 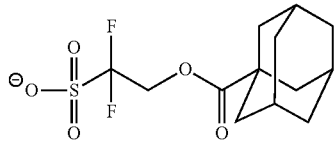
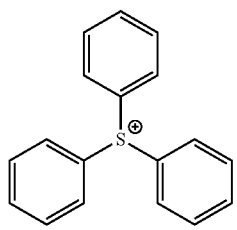 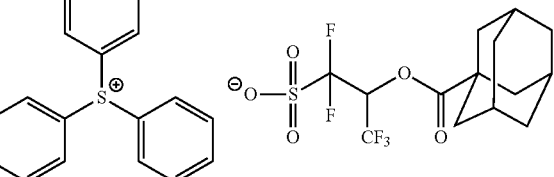
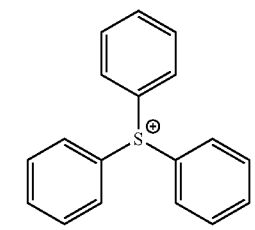
-continued
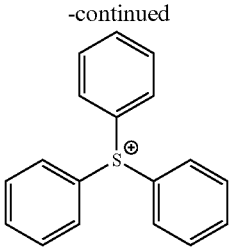
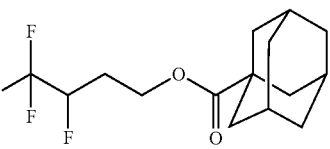
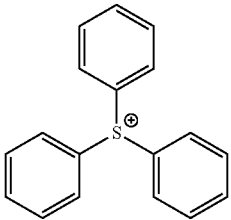
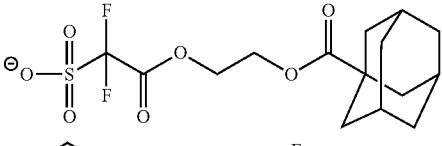
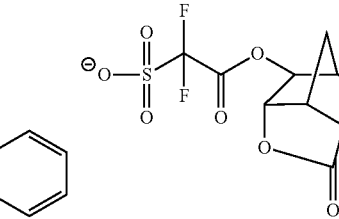
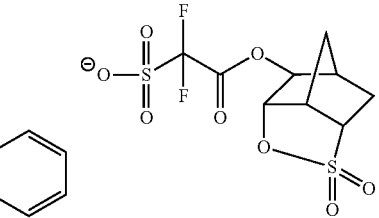
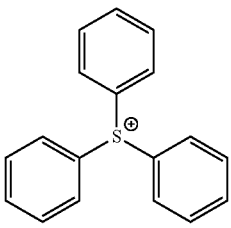
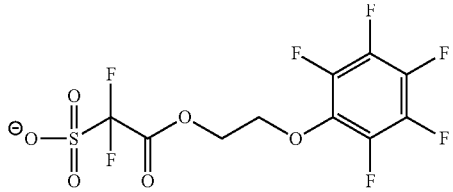

-continued

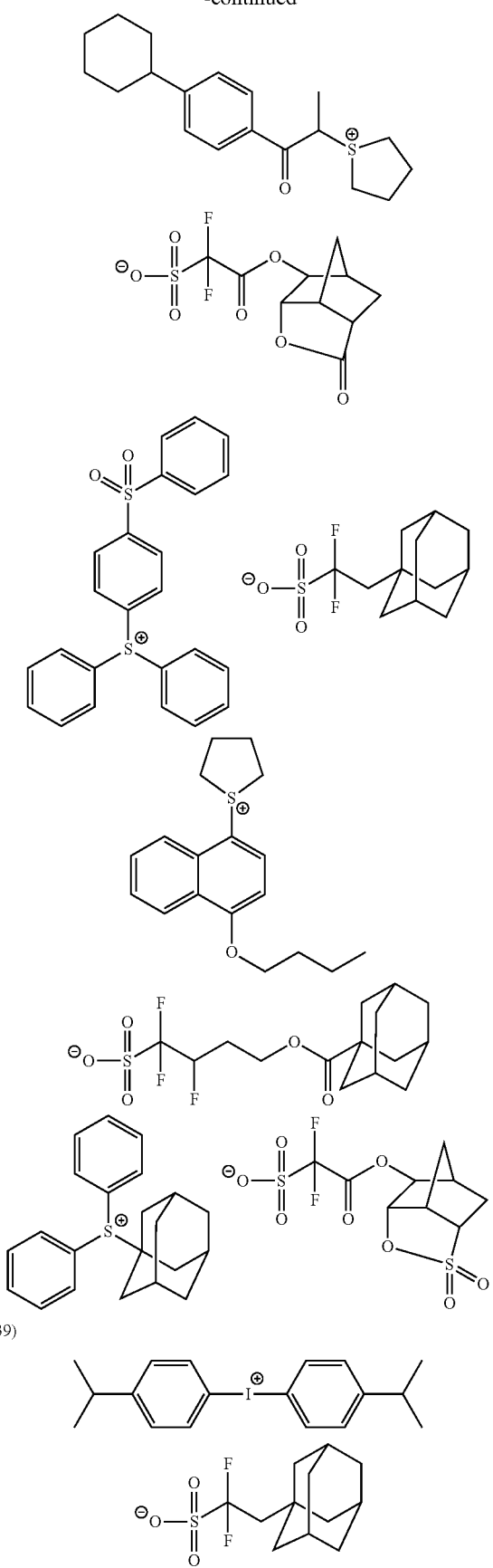

(39)

-continued

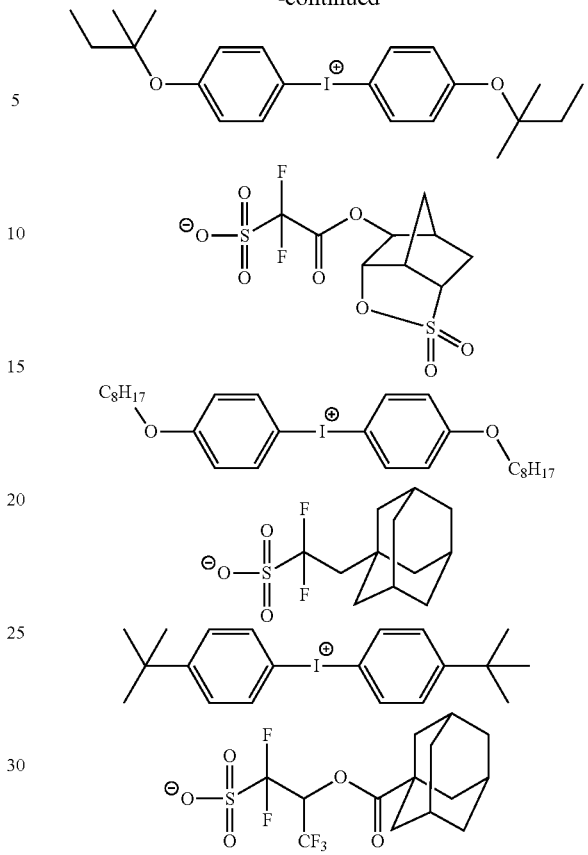

The acid generating agents can be synthesized by well-known methods, and can be synthesized, for example, by the methods disclosed in JP2007-161707A, [0200] to [0210] of JP2010-100595A, [0051] to [0058] of WO2011/093280A, [0382] to [0385] of WO2008/153110A, and JP2007-161707A.

The acid generating agent may be used singly, or two or more types thereof may be used in combination.

The content of the compound that generates an acid by the irradiation with the active ray or the radiant ray, in the composition is preferably in the range of 0.1% by mass to 30% by mass, more preferably in the range of 0.5% by mass to 25% by mass, still more preferably in the range of 3% by mass to 20% by mass, and particularly preferably in the range of 3% by mass to 15% by mass based on the total solid content of the chemical amplification type resist composition.

In addition, according to the resist composition, there is an embodiment (B') in which the structure corresponding to the acid generating agent is carried in the resin (A). As the embodiments, specifically, a structure (particularly, a structure disclosed in paragraphs 0164 to 0191 and a structure included in a resin disclosed in an example of paragraph 0555) disclosed in JP2011-248019A and the like are included. That is, the structure corresponding to the acid generating agent is an embodiment carried in the resin (A), and the resist composition may additionally include an acid generating agent that is not carried in the resin (A).

As the embodiment (B'), repeating units described below are included, but the invention is not limited thereto.

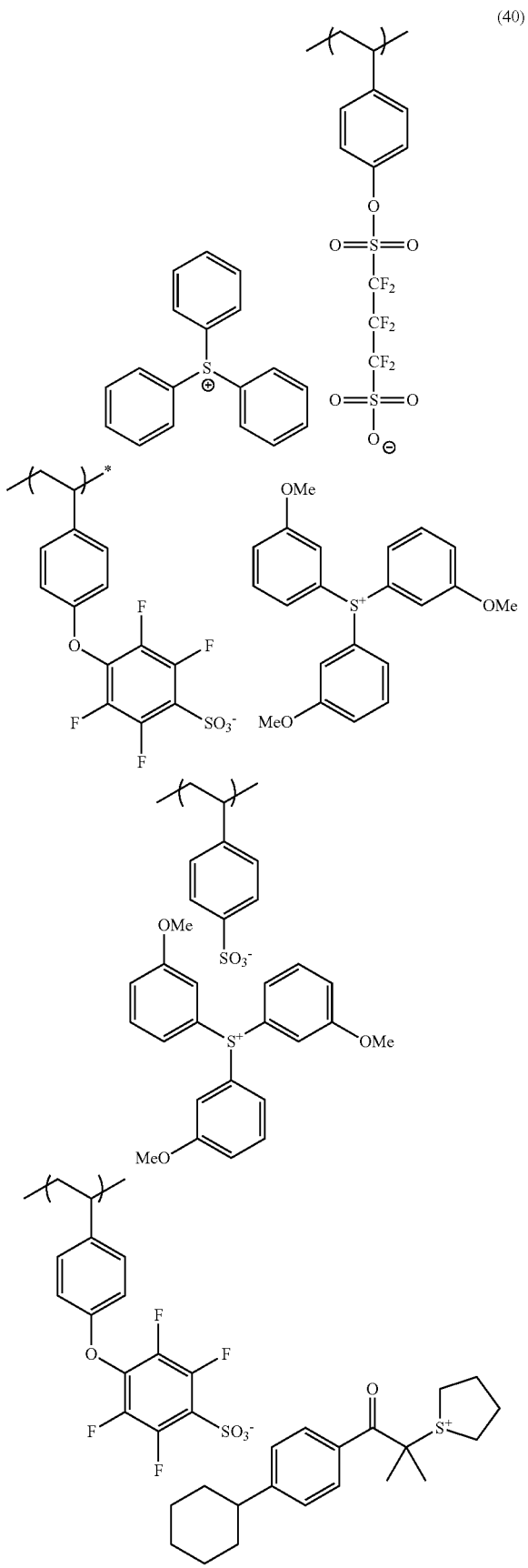

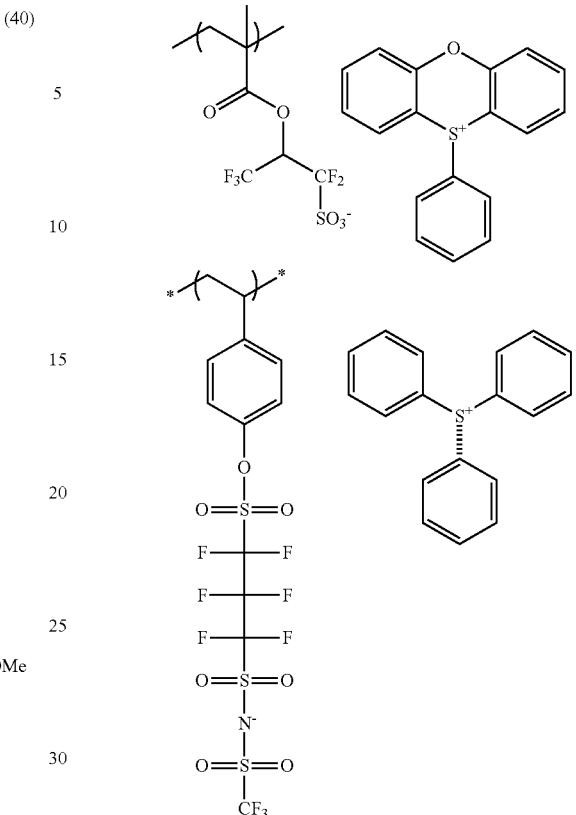

[3] (C) Solvent

The chemical amplification type resist composition generally contains a solvent (C).

As the solvent that can be used when the chemical amplification type resist composition is prepared, for example, organic solvents such as alkylene glycol monoalkyl ether carboxylate, alkylene glycol monoalkyl ether, alkyl lactate ester, alkoxy propionic acid alkyl, cyclic lactone (preferably, having 4 to 10 carbon atoms), a monoketone compound (preferably, having 4 to 10 carbon atoms) that may have a ring, alkylene carbonate, alkoxy alkyl acetate, and alkyl pyruvate can be included.

As a specific example of these solvents, products disclosed in [0441] to [0455] of US2008/0187860A can be included.

According to the invention, as the organic solvent, a mixed solvent obtained by mixing a solvent that contains a hydroxyl group in a structure and a solvent that does not contain a hydroxyl group may be used.

As the solvent that contains the hydroxyl group and the solvent that does not contain the hydroxyl group, exemplified compounds described above can be appropriately selected. However, as the solvent that contains the hydroxyl group, alkylene glycol monoalkyl ether, alkyl lactate, and the like are preferable, and propylene glycol monomethyl ether (PGME, also known as 1-methoxy-2-propanol) and ethyl lactate are more preferable. In addition, as the solvent that does not contain the hydroxyl group, alkylene glycol mono alkyl ether acetate, alkyl alkoxy propionate, a monoketone compound that may contain a ring, cyclic lactone, alkyl acetate, and the like are preferable. Among these, propylene glycol monomethyl ether acetate (PGMEA, also known as 1-methoxy-2-acetoxypropane), ethyl ethoxypropionate, 2-heptanone, γ-butyrolactone, cyclohexanone, and butyl acetate are particularly preferable, and propylene glycol monomethyl ether acetate, ethyl ethoxypropionate, and 2-heptanone are most preferable.

A mixture ratio (mass) of the solvent that contains the hydroxyl group and the solvent that does not contain the hydroxyl group is in the range of 1/99 to 99/1, preferably in the range of 10/90 to 90/10, and more preferably in the range of 20/80 to 60/40. A mixed solvent containing 50% by mass or more of the solvent that does not contain the hydroxyl group is particularly preferable in view of the application uniformity.

The solvent preferably includes propylene glycol monomethyl ether acetate, and a single dissolving agent of propylene glycol monomethyl ether acetate, or a mixture of two or more solvents that contains propylene glycol monomethyl ether acetate is preferable.

[4] Hydrophobic Resin (D)

The chemical amplification type resist composition according to the invention may contain a hydrophobic resin (hereinafter, referred to as the "hydrophobic resin (D)" or simply as the "resin (D)") particularly at the time of being applied to the liquid immersion exposure. In addition, the hydrophobic resin (D) is preferably different from the resin (A).

Accordingly, the hydrophobic resin (D) is unevenly distributed on the film surface, and if the immersion medium is water, a static/dynamic contact angle on the resist film surface to water is improved and thus conformability to an immersion fluid can be improved.

It is preferable that the hydrophobic resin (D) is designed to be unevenly distributed on the interface as described above, but, differently from the surfactant, a hydrophilic group does not need to be included in the molecule and does not have to contribute to the even mixture of the polar/non-polar materials.

In view of the uneven distribution on the film surface, the hydrophobic resin (D) preferably includes any one or more types of a "fluorine atom", a "silicon atom", and a "$CH_3$ substructure contained in a side chain portion of the resin" and more preferably includes two or more types thereof.

The weight average molecular weight of the hydrophobic resin (D) in terms of standard polystyrene is preferably in the range of 1,000 to 100,000, more preferably in the range of 1,000 to 50,000, and still more preferably in the range of 2,000 to 15,000.

In addition, the hydrophobic resin (D) may be used singly, or two or more types thereof may be used in combination.

The content of the hydrophobic resin (D) in the composition is preferably in the range of 0.01% by mass to 10% by mass, more preferably in the range of 0.05% by mass to 8% by mass, and still more preferably in the range of 0.1% by mass to 7% by mass with respect to the total solid content in the composition according to the invention.

The hydrophobic resin (D) obviously includes fewer impurities such as metal in the same manner as in the resin (A), and residual monomer or oligomer components are preferably in the range of 0.01% by mass to 5% by mass, more preferably in the range of 0.01% by mass to 3% by mass, and still more preferably in the range of 0.05% by mass to 1% by mass. Accordingly, the chemical amplification type resist composition that does not have foreign substances in the fluid or a change of the sensitivity with time can be obtained. In addition, in view of the resolution, the resist shape, the sidewalls of the resist pattern, and roughness, the molecular weight distribution (Mw/Mn, also referred to as a "dispersion degree") is preferably in the range of 1 to 5, more preferably in the range of 1 to 3, and still more preferably in the range of 1 to 2.

As the hydrophobic resin (D), various kinds of commercially available products may be used, or the hydrophobic resin (D) may be synthesized by a usual method (for example, radical polymerization). For example, as a general synthesization method, a collective polymerization method that performs polymerization in which a monomer species and an initiator are dissolved in a solvent and baked, and a dripping polymerization method in which a solution of a monomer species and an initiator is dripped to a baking solvent for 1 hour to 10 hours to be added are included. The dripping polymerization method is preferable.

A reaction dissolving agent, a polymerization initiator, a reaction condition (temperature, density, and the like), and a refining method after the reaction are the same as described for the resin (A), but in the synthesization of the hydrophobic resin (D), the density of the reaction is preferably in the range of 30% by mass to 50% by mass. More specifically, the description around paragraphs 0320 to 0329 of JP2008-292975A is referred to.

Hereinafter, the specific examples of the hydrophobic resin (D) are described. In addition, in tables below, molar ratios (corresponding to the respective repeating units in the sequence from the left), weight average molecular weights, and dispersion degrees of the repeating units in the respective resins are presented.

(41)

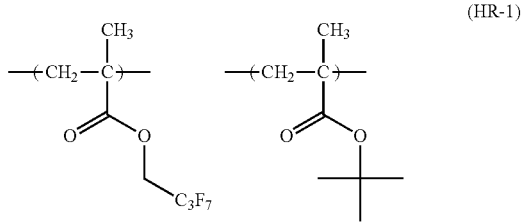

(HR-1)

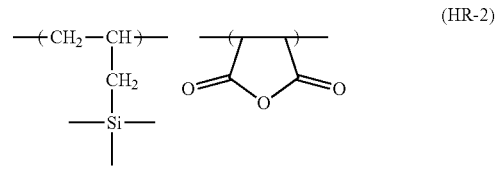

(HR-2)

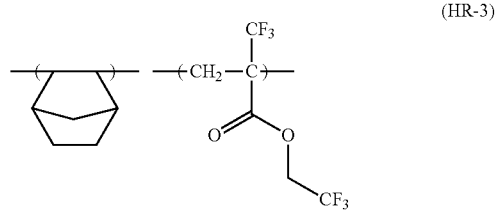

(HR-3)

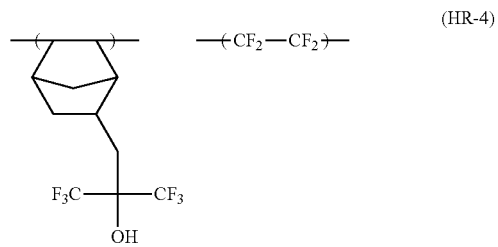

(HR-4)

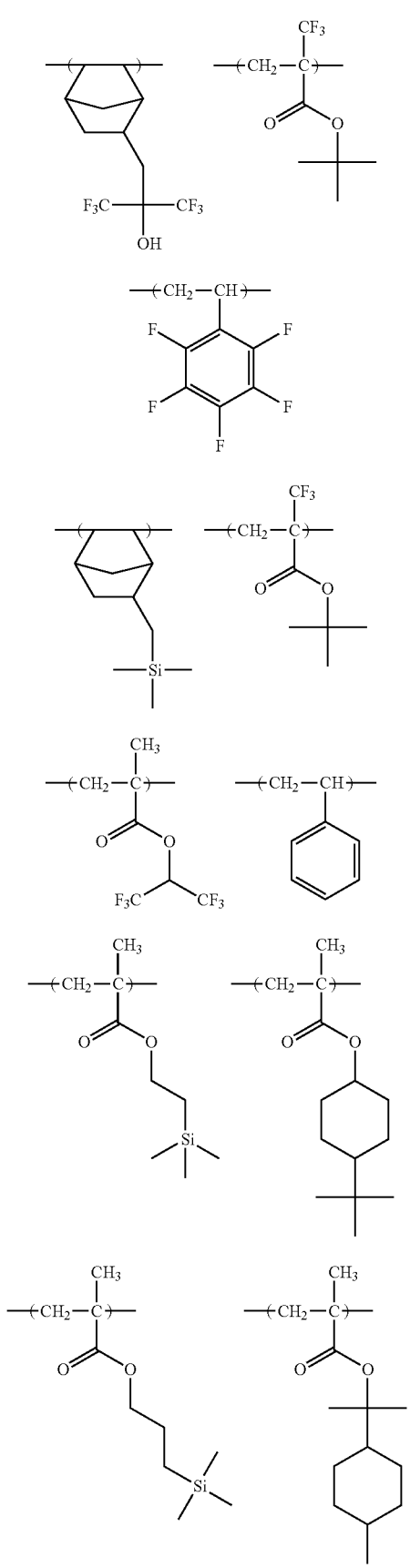
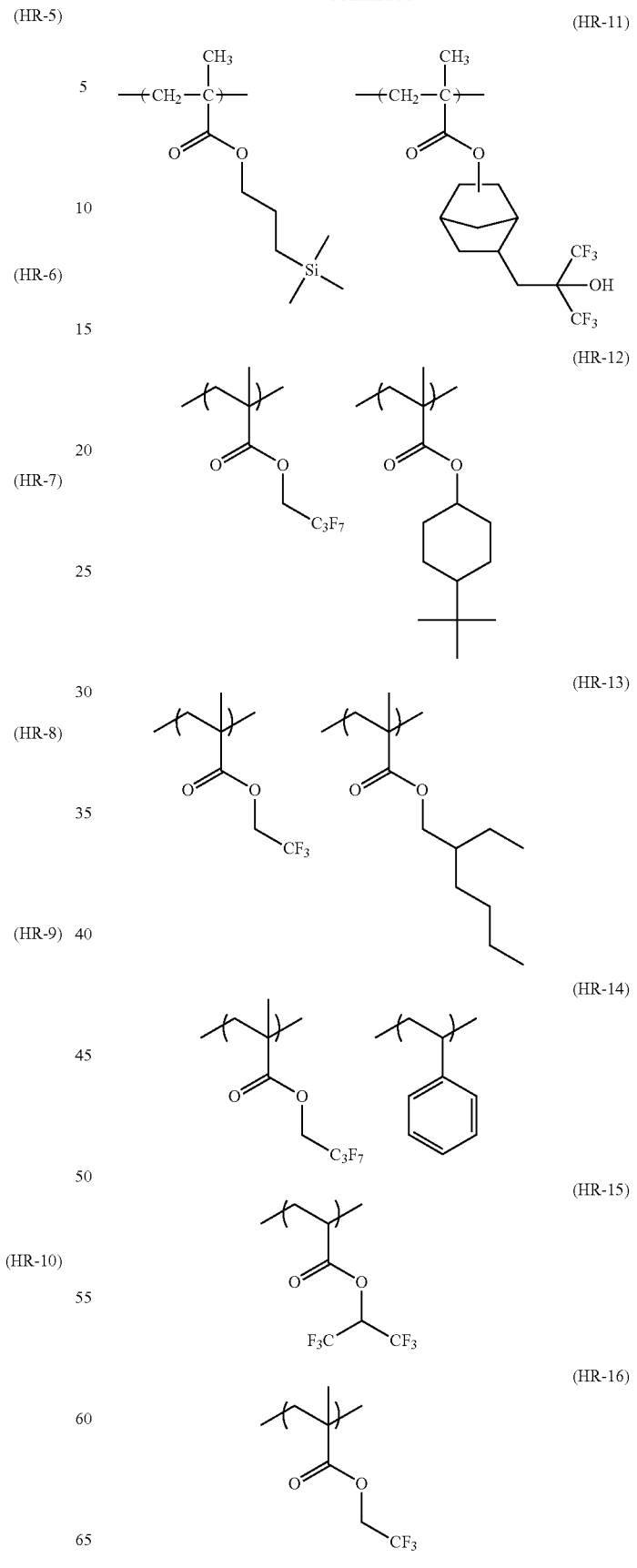

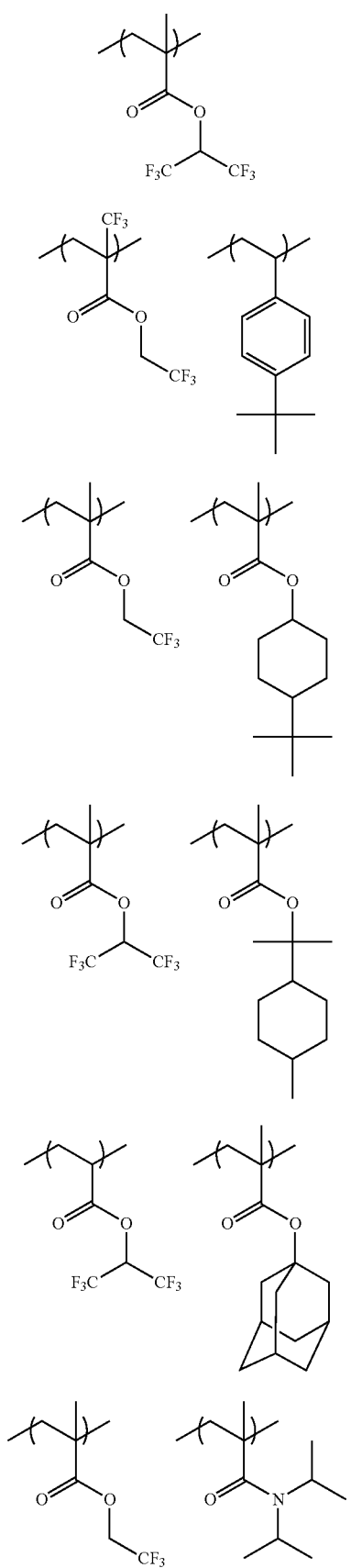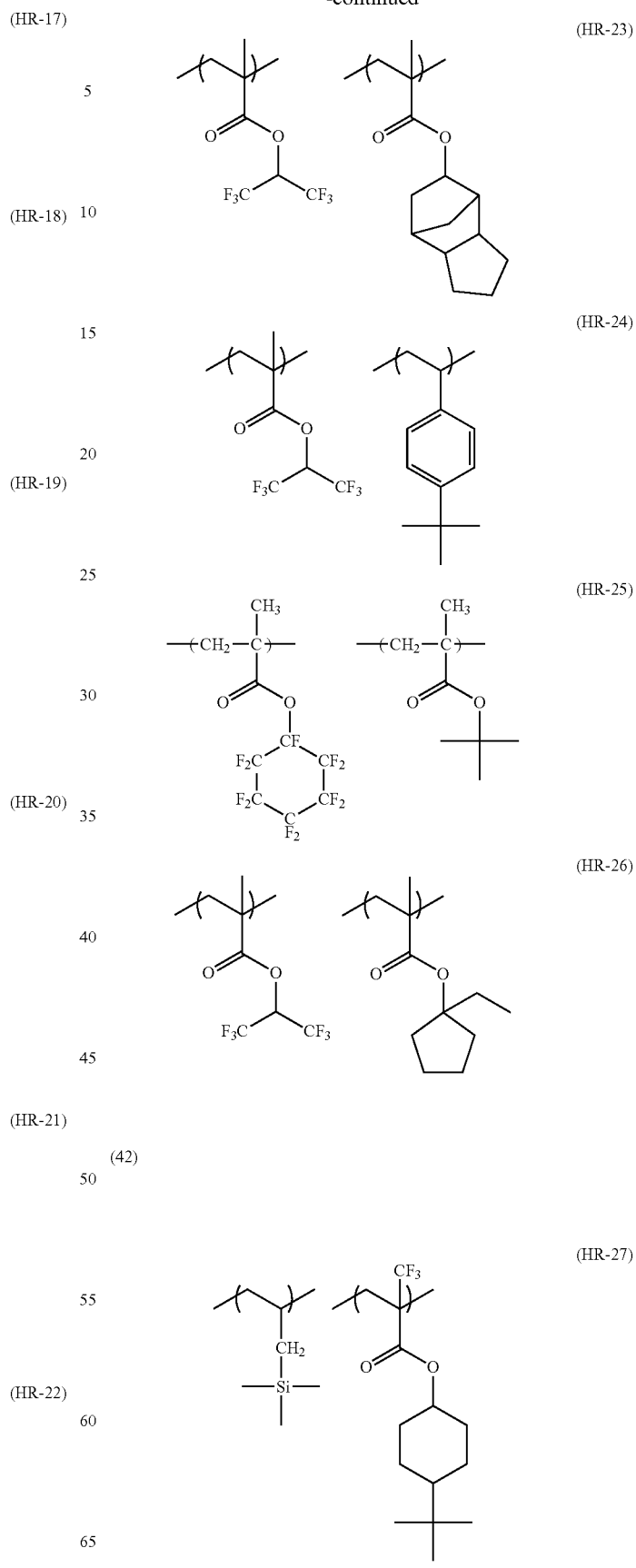

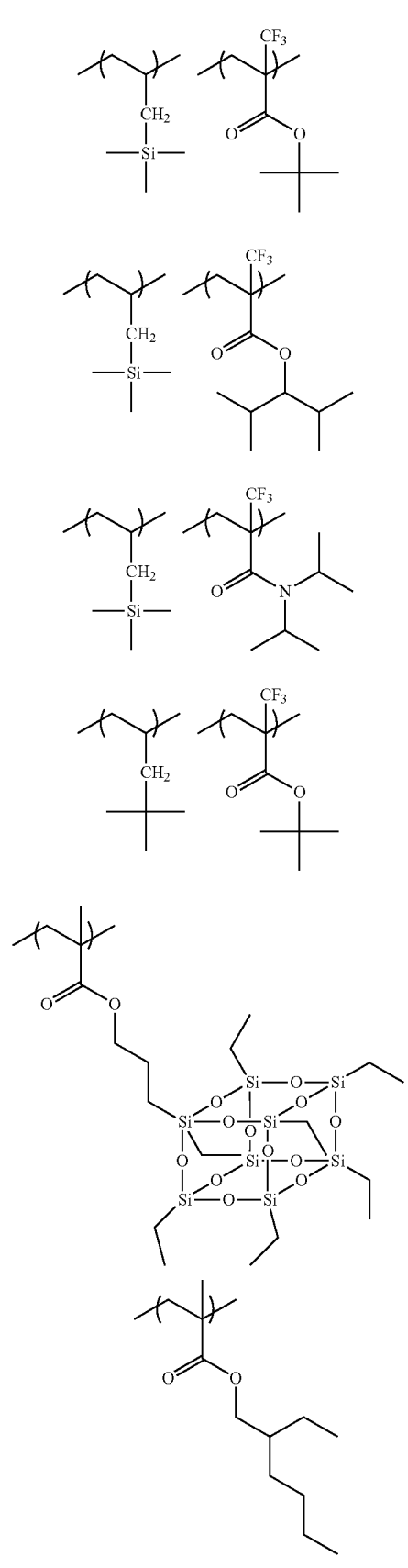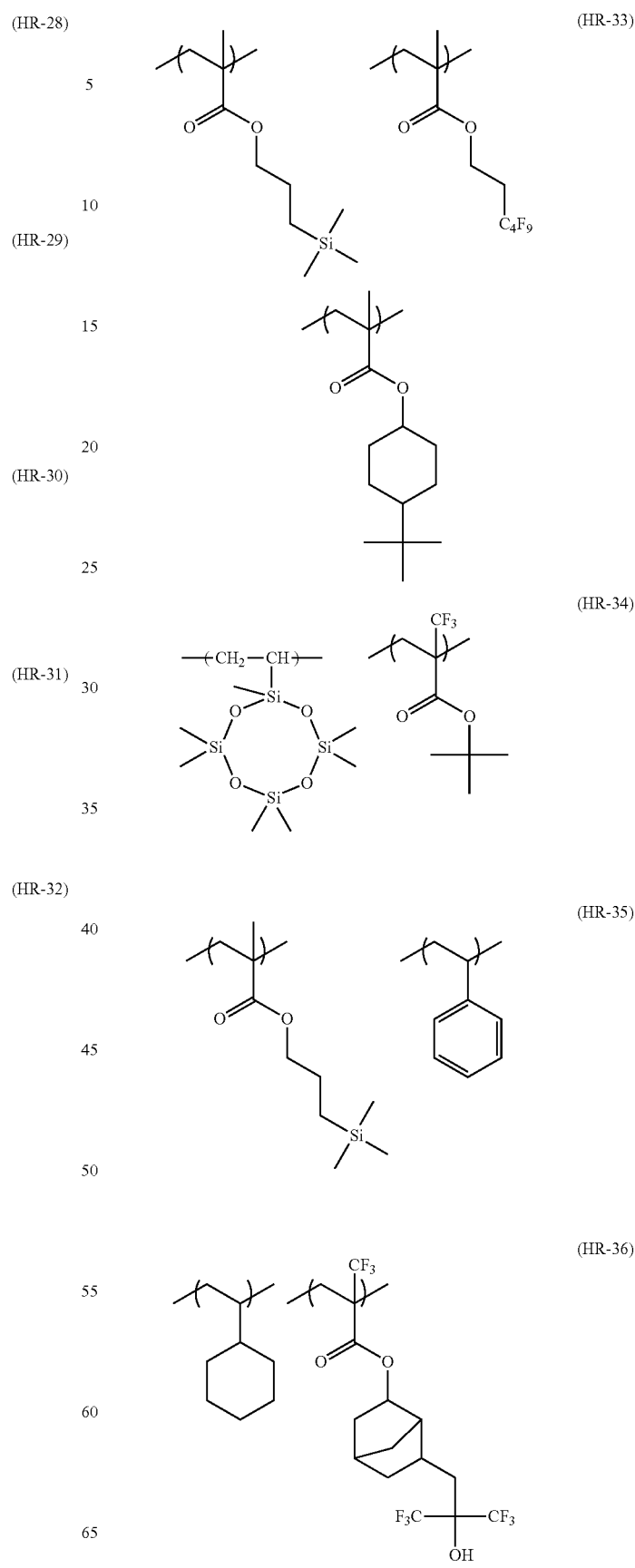

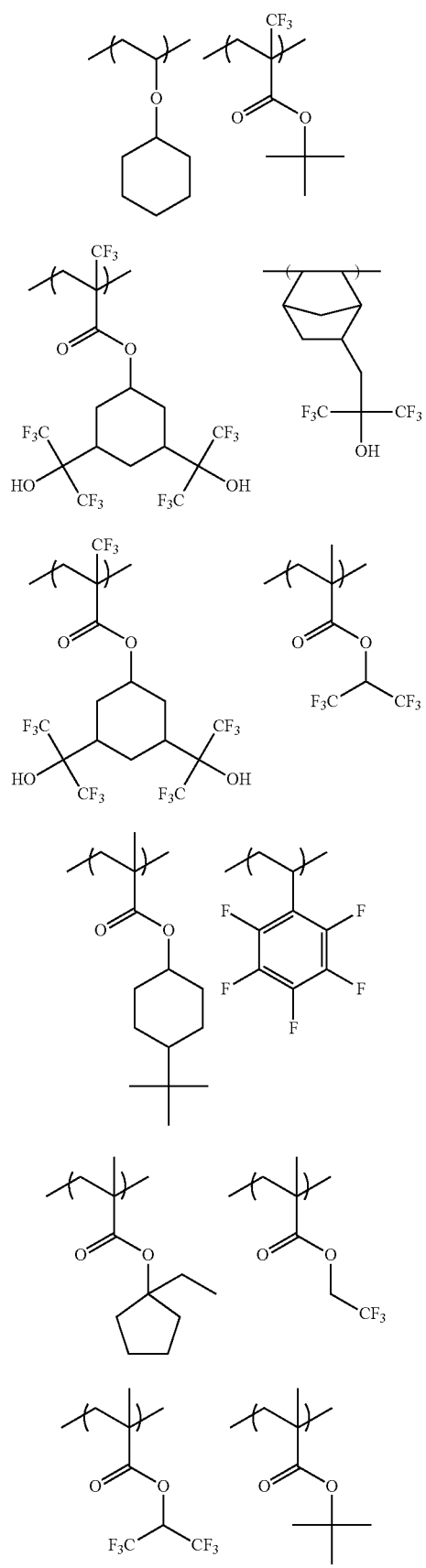
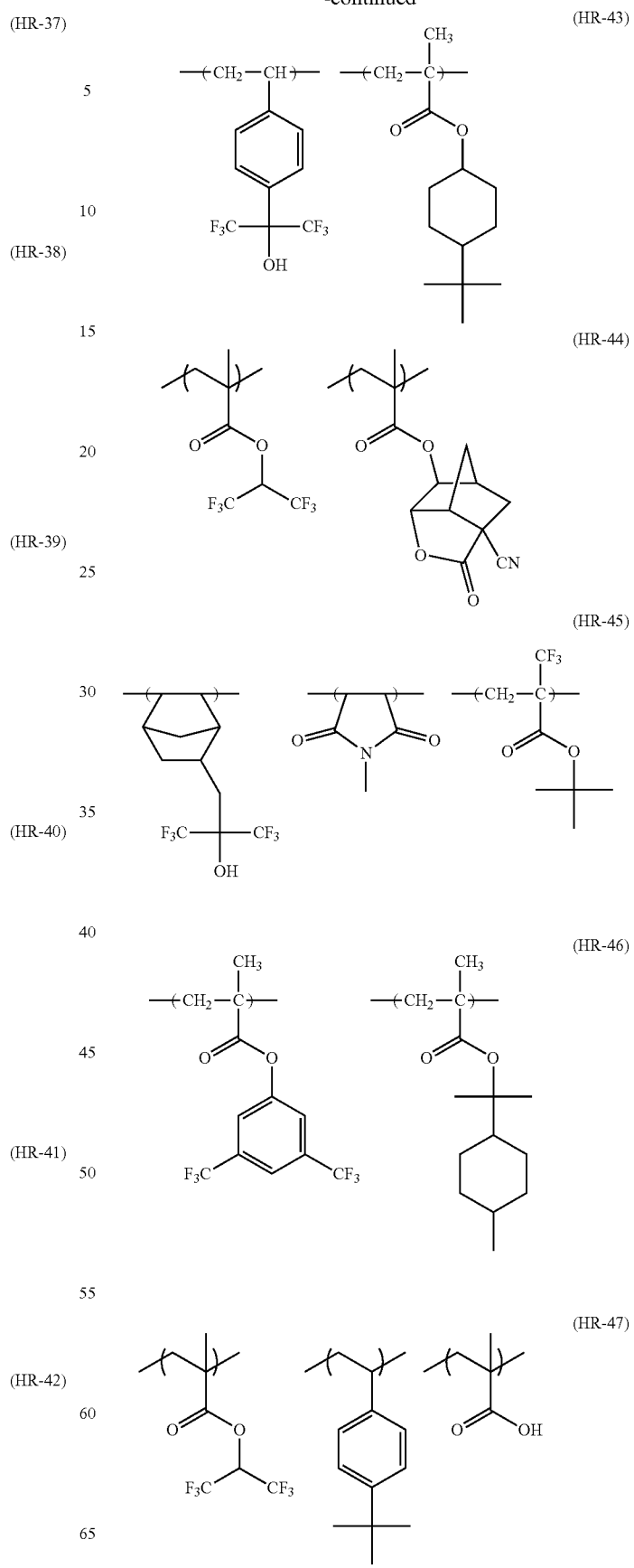

(HR-48)
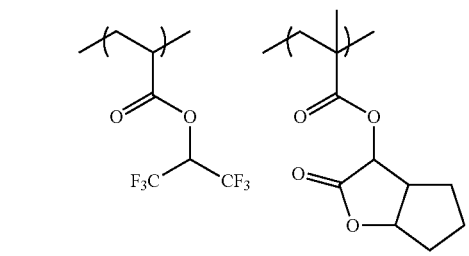
(HR-49)
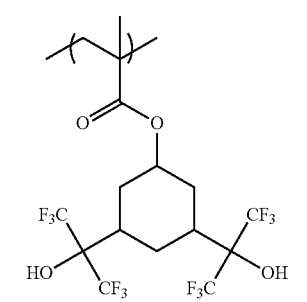
(HR-50)
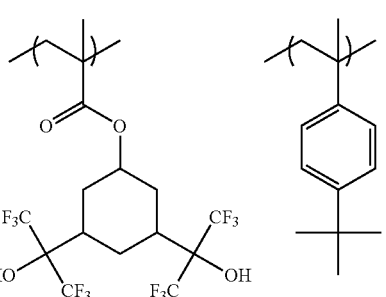
(HR-51)
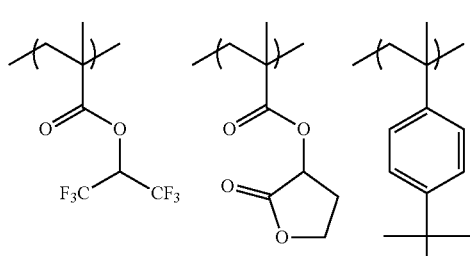
(HR-52)
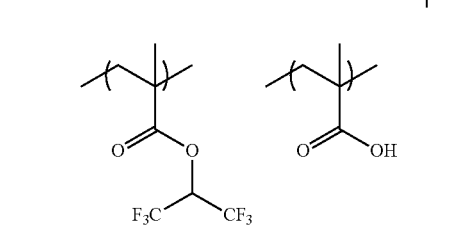
(HR-53)
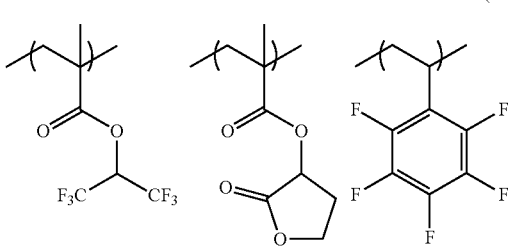
(HR-54)
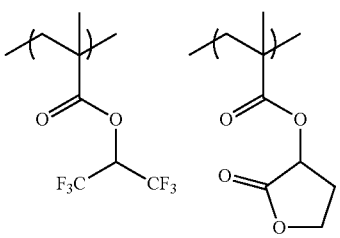
(HR-55)
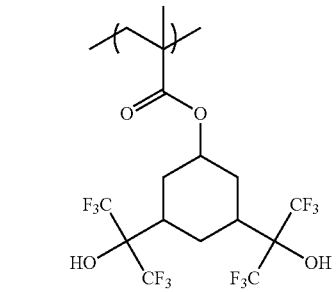
(HR-56)
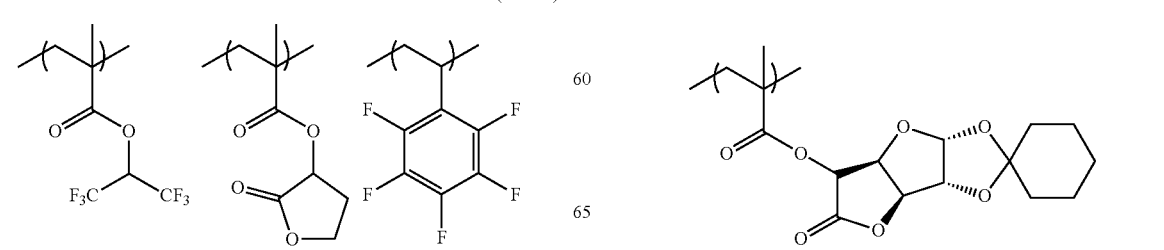

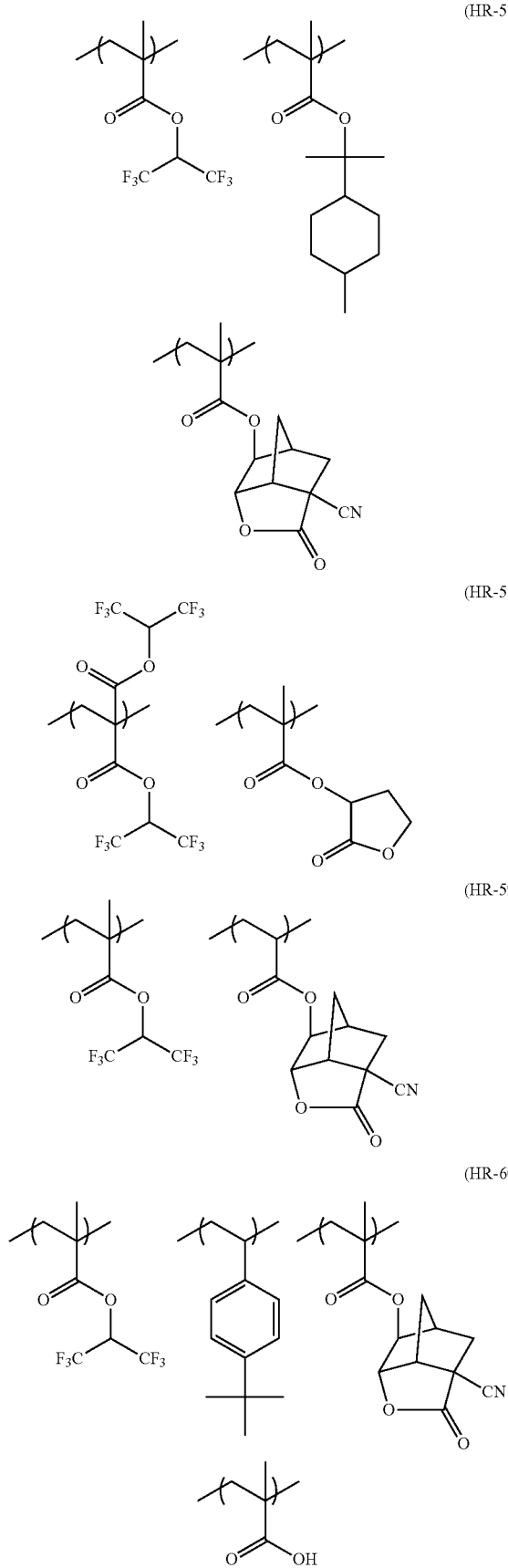
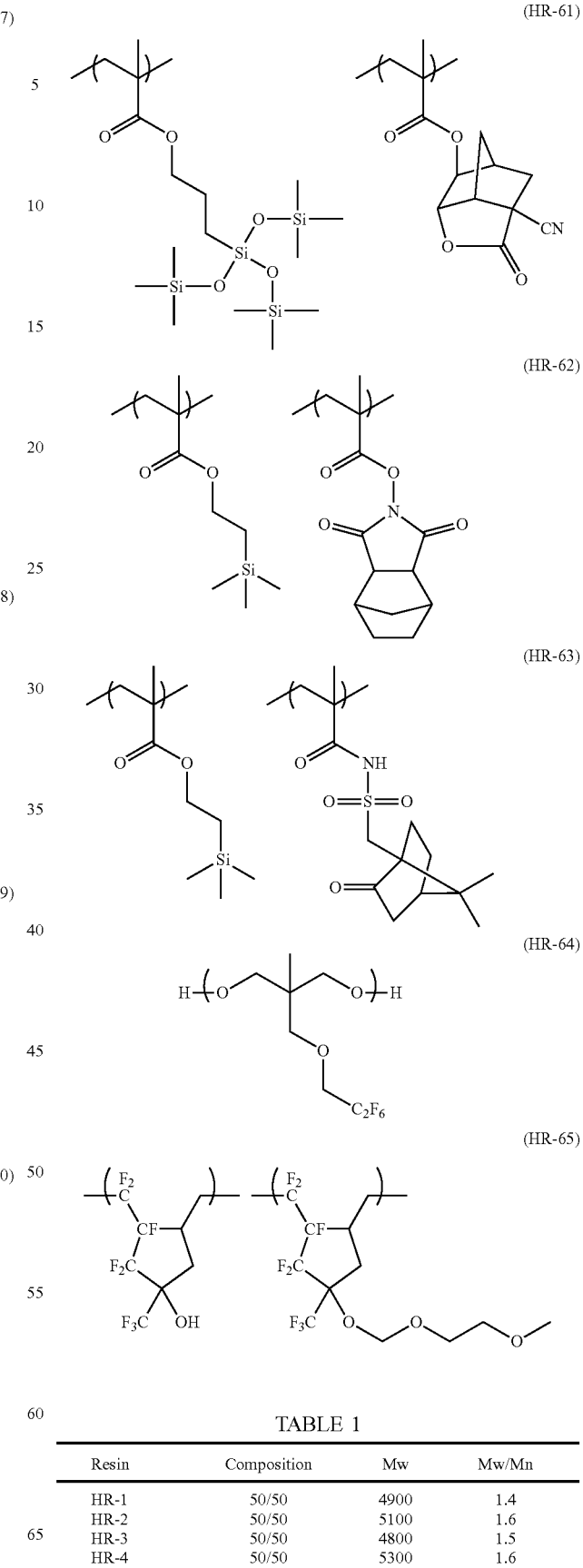
| Resin | Composition | Mw | Mw/Mn |
|---|---|---|---|
| HR-1 | 50/50 | 4900 | 1.4 |
| HR-2 | 50/50 | 5100 | 1.6 |
| HR-3 | 50/50 | 4800 | 1.5 |
| HR-4 | 50/50 | 5300 | 1.6 |

TABLE 1-continued
| Resin | Composition | Mw | Mw/Mn |
|---|---|---|---|
| HR-5 | 50/50 | 4500 | 1.4 |
| HR-6 | 100 | 5500 | 1.6 |
| HR-7 | 50/50 | 5800 | 1.9 |
| HR-8 | 50/50 | 4200 | 1.3 |
| HR-9 | 50/50 | 5500 | 1.8 |
| HR-10 | 40/60 | 7500 | 1.6 |
| HR-11 | 70/30 | 6600 | 1.8 |
| HR-12 | 40/60 | 3900 | 1.3 |
| HR-13 | 50/50 | 9500 | 1.8 |
| HR-14 | 50/50 | 5300 | 1.6 |
| HR-15 | 100 | 6200 | 1.2 |
| HR-16 | 100 | 5600 | 1.6 |
| HR-17 | 100 | 4400 | 1.3 |
| HR-18 | 50/50 | 4300 | 1.3 |
| HR-19 | 50/50 | 6500 | 1.6 |
| HR-20 | 30/70 | 6500 | 1.5 |
| HR-21 | 50/50 | 6000 | 1.6 |
| HR-22 | 50/50 | 3000 | 1.2 |
| HR-23 | 50/50 | 5000 | 1.5 |
| HR-24 | 50/50 | 4500 | 1.4 |
| HR-25 | 30/70 | 5000 | 1.4 |
| HR-26 | 50/50 | 5500 | 1.6 |
| HR-27 | 50/50 | 3500 | 1.3 |
| HR-28 | 50/50 | 6200 | 1.4 |
| HR-29 | 50/50 | 6500 | 1.6 |
| HR-30 | 50/50 | 6500 | 1.6 |
| HR-31 | 50/50 | 4500 | 1.4 |
| HR-32 | 30/70 | 5000 | 1.6 |
| HR-33 | 30/30/40 | 6500 | 1.8 |
| HR-34 | 50/50 | 4000 | 1.3 |
| HR-35 | 50/50 | 6500 | 1.7 |
| HR-36 | 50/50 | 6000 | 1.5 |
| HR-37 | 50/50 | 5000 | 1.6 |
| HR-38 | 50/50 | 4000 | 1.4 |
| HR-39 | 20/80 | 6000 | 1.4 |
| HR-40 | 50/50 | 7000 | 1.4 |
| HR-41 | 50/50 | 6500 | 1.6 |
| HR-42 | 50/50 | 5200 | 1.6 |
| HR-43 | 50/50 | 6000 | 1.4 |
| HR-44 | 70/30 | 5500 | 1.6 |
| HR-45 | 50/20/30 | 4200 | 1.4 |
| HR-46 | 30/70 | 7500 | 1.6 |
| HR-47 | 40/58/2 | 4300 | 1.4 |
| HR-48 | 50/50 | 6800 | 1.6 |
| HR-49 | 100 | 6500 | 1.5 |
| HR-50 | 50/50 | 6600 | 1.6 |
| HR-51 | 30/20/50 | 6800 | 1.7 |
| HR-52 | 95/5 | 5900 | 1.6 |
| HR-53 | 40/30/30 | 4500 | 1.3 |
| HR-54 | 50/30/20 | 6500 | 1.8 |
| HR-55 | 30/40/30 | 7000 | 1.5 |
| HR-56 | 60/40 | 5500 | 1.7 |
| HR-57 | 40/40/20 | 4000 | 1.3 |
| HR-58 | 60/40 | 3800 | 1.4 |
| HR-59 | 80/20 | 7400 | 1.6 |
| HR-60 | 40/40/15/5 | 4800 | 1.5 |
| HR-61 | 60/40 | 5600 | 1.5 |
| HR-62 | 50/50 | 5900 | 2.1 |
| HR-63 | 80/20 | 7000 | 1.7 |
| HR-64 | 100 | 5500 | 1.8 |
| HR-65 | 50/50 | 9500 | 1.9 |
(44)
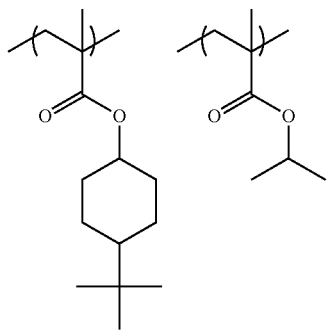
(C-1)
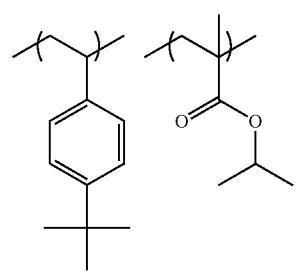
(C-2)
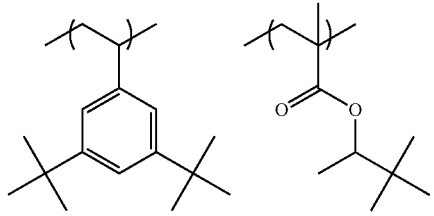
(C-3)
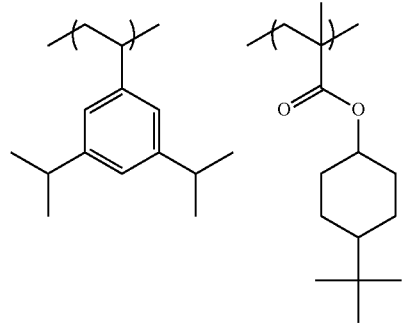
(C-4)
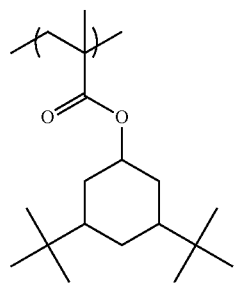
(C-5)

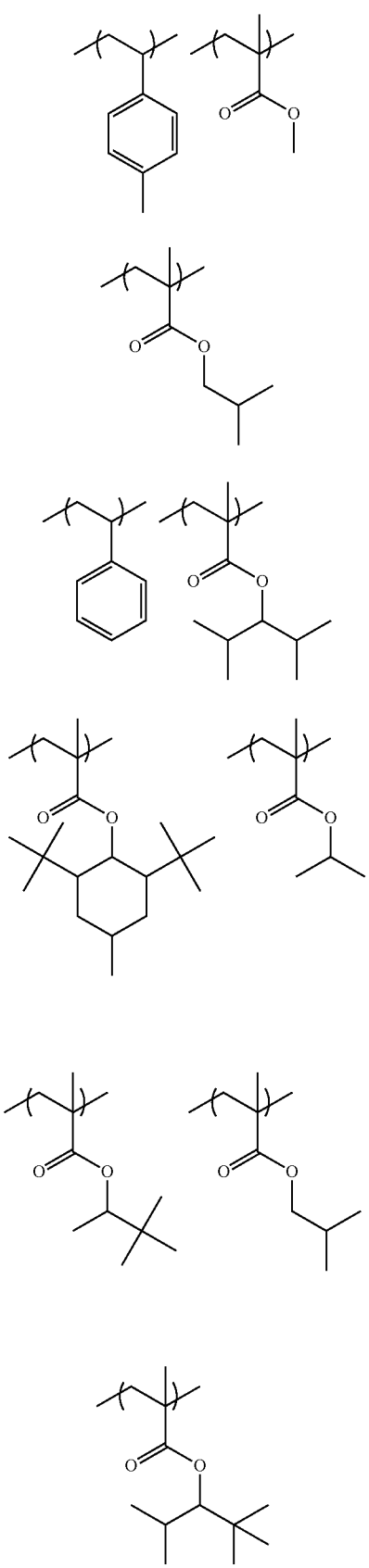

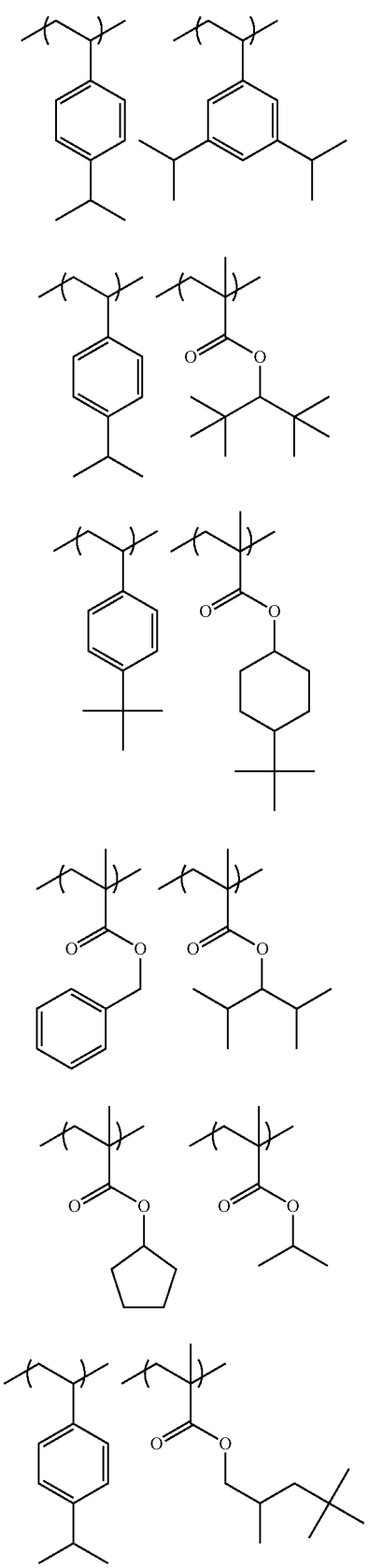
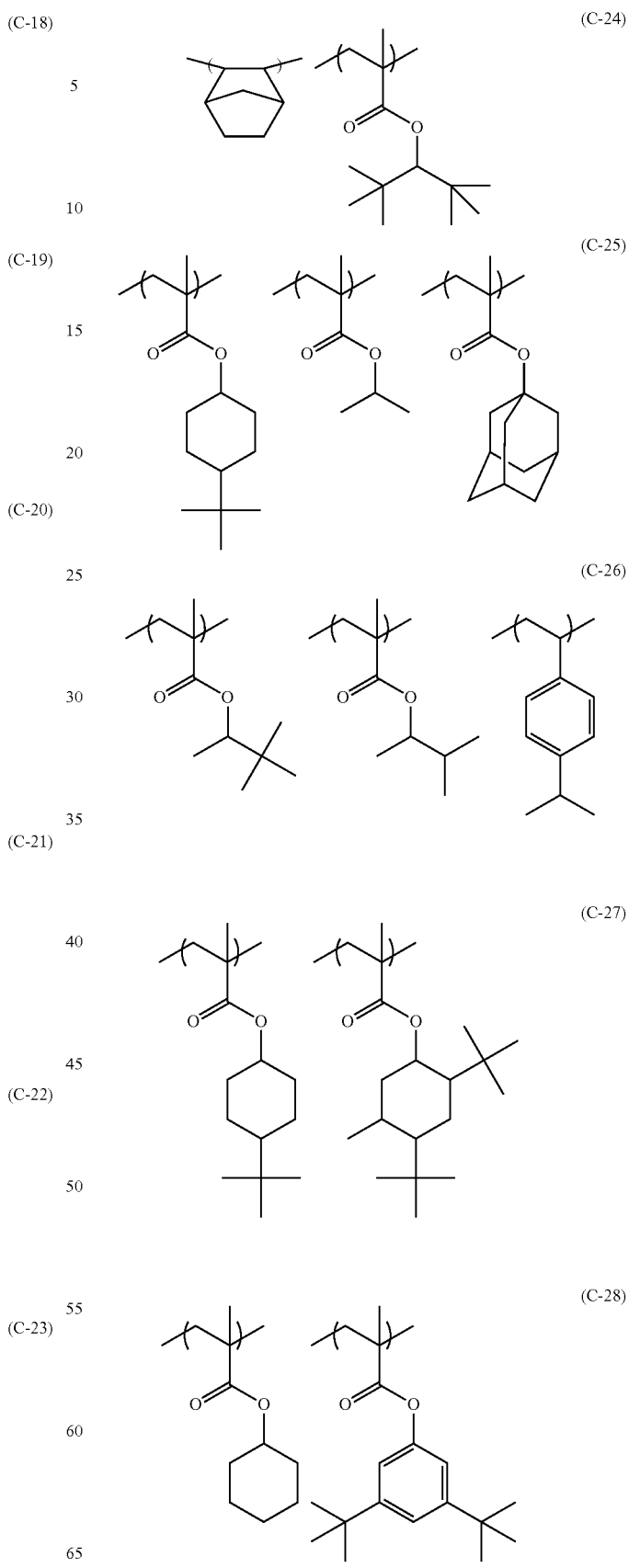

(46)
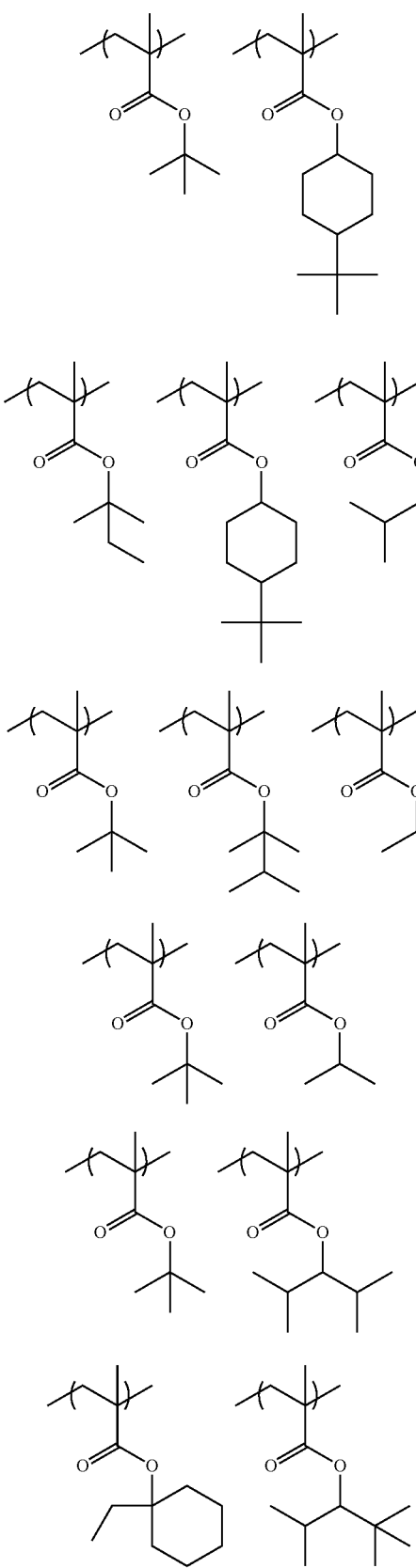
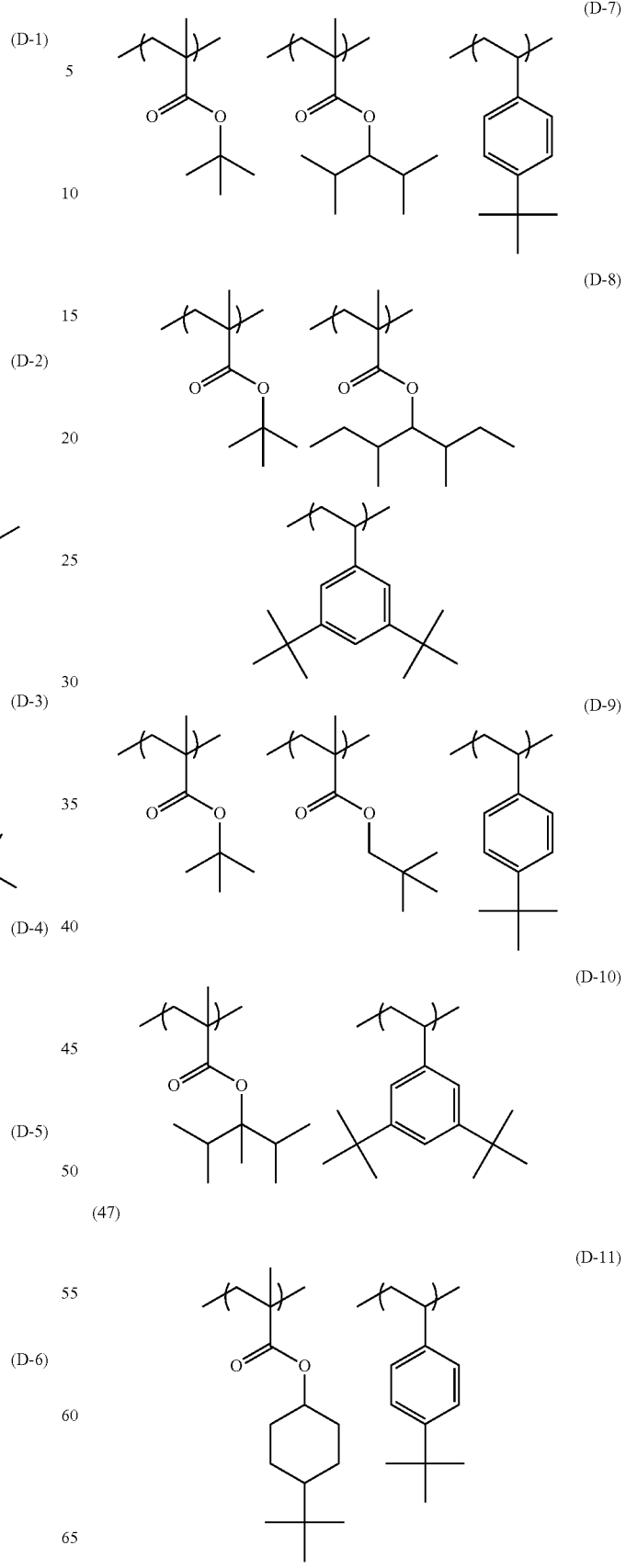

-continued (D-12)

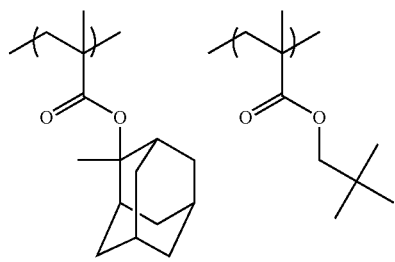

(D-13)

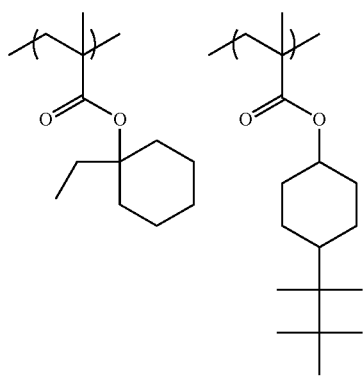

(D-14)

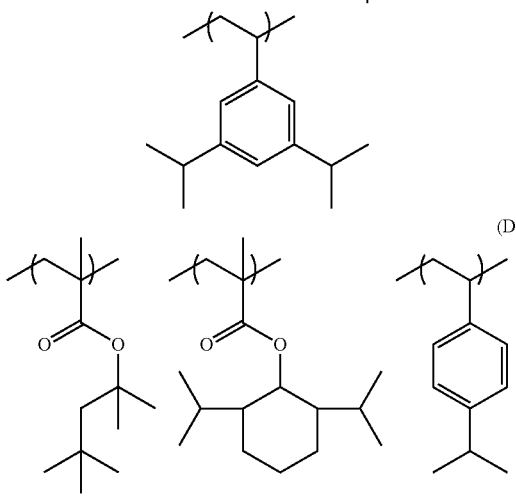

(D-15)

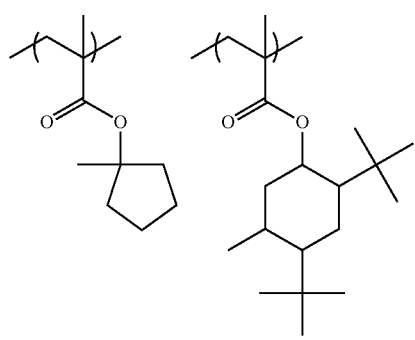

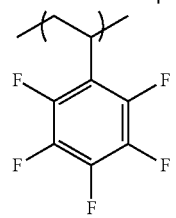

-continued (D-16)

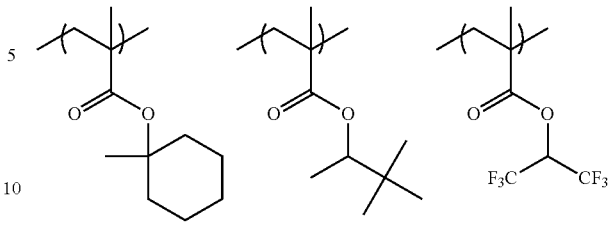

TABLE 2

| Resin | Composition | Mw | Mw/Mn |
|---|---|---|---|
| C-1 | 50/50 | 9600 | 1.74 |
| C-2 | 60/40 | 34500 | 1.43 |
| C-3 | 30/70 | 19300 | 1.69 |
| C-4 | 90/10 | 26400 | 1.41 |
| C-5 | 100 | 27600 | 1.87 |
| C-6 | 80/20 | 4400 | 1.96 |
| C-7 | 100 | 16300 | 1.83 |
| C-8 | 5/95 | 24500 | 1.79 |
| C-9 | 20/80 | 15400 | 1.68 |
| C-10 | 50/50 | 23800 | 1.46 |
| C-11 | 100 | 22400 | 1.57 |
| C-12 | 10/90 | 21600 | 1.52 |
| C-13 | 100 | 28400 | 1.58 |
| C-14 | 50/50 | 16700 | 1.82 |
| C-15 | 100 | 23400 | 1.73 |
| C-16 | 60/40 | 18600 | 1.44 |
| C-17 | 80/20 | 12300 | 1.78 |
| C-18 | 40/60 | 18400 | 1.58 |
| C-19 | 70/30 | 12400 | 1.49 |
| C-20 | 50/50 | 23500 | 1.94 |
| C-21 | 10/90 | 7600 | 1.75 |
| C-22 | 5/95 | 14100 | 1.39 |
| C-23 | 50/50 | 17900 | 1.61 |
| C-24 | 10/90 | 24600 | 1.72 |
| C-25 | 50/40/10 | 23500 | 1.65 |
| C-26 | 60/30/10 | 13100 | 1.51 |
| C-27 | 50/50 | 21200 | 1.84 |
| C-28 | 10/90 | 19500 | 1.66 |

TABLE 3

| Resin | Composition | Mw | Mw/Mn |
|---|---|---|---|
| D-1 | 50/50 | 16500 | 1.72 |
| D-2 | 10/50/40 | 18000 | 1.77 |
| D-3 | 5/50/45 | 27100 | 1.69 |
| D-4 | 20/80 | 26500 | 1.79 |
| D-5 | 10/90 | 24700 | 1.83 |
| D-6 | 10/90 | 15700 | 1.99 |
| D-7 | 5/90/5 | 21500 | 1.92 |
| D-8 | 5/60/35 | 17700 | 2.10 |
| D-9 | 35/35/30 | 25100 | 2.02 |
| D-10 | 70/30 | 19700 | 1.85 |
| D-11 | 75/25 | 23700 | 1.80 |
| D-12 | 10/90 | 20100 | 2.02 |
| D-13 | 5/35/60 | 30100 | 2.17 |
| D-14 | 5/45/50 | 22900 | 2.02 |
| D-15 | 15/75/10 | 28600 | 1.81 |
| D-16 | 25/55/20 | 27400 | 1.87 |

[5] Basic Compound

The chemical amplification type resist composition according to the invention preferably contains a basic compound.

The chemical amplification type resist composition preferably contains a basic compound or an ammonium salt compound (hereinafter, referred to as a "compound (N)") of which basicity decreases by the irradiation with the active ray or the radiant ray, as the basic compound.

The compound (N) is preferably a compound (N-1) having a basic functional group or an ammonium group and a group that generates an acidic functional group by the irradiation with the active ray or the radiant ray. That is, the compound (N) is preferably a basic compound having a basic functional group and a group that generates an acidic functional group by the irradiation with an active ray or a radiant ray, or an ammonium salt compound having an ammonium group and a group that generates an acidic functional group by the irradiation with the active ray or the radiant ray. Particularly preferable compound examples are exemplified below. In addition, compounds exemplified as (A-1) to (A-23) on page 5 and subsequent pages in US2012/0156617A, and compounds exemplified as (A-1) to (A-44) on page 9 and subsequent pages in US2006/0264528A are preferably included.

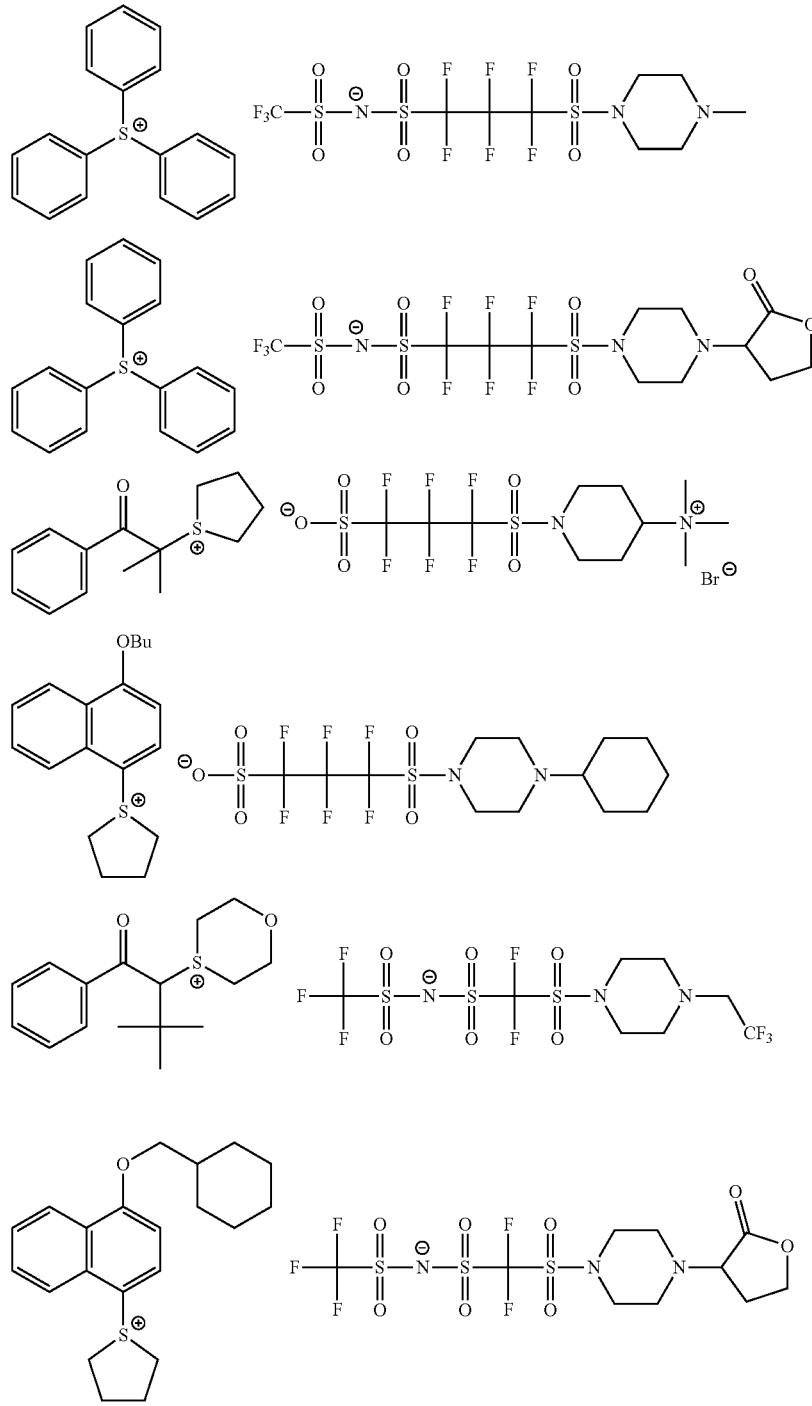

(48)

These compounds can be synthesized by synthesization examples of JP2006-330098A.

The molecular weight of the compound (N) is preferably in the range of 500 to 1,000.

The chemical amplification type resist composition according to the invention may not contain the compound (N), but if the chemical amplification type resist composition according to the invention contains the compound (N), the content of the compound (N) is preferably in the range of 0.1% by mass to 20% by mass, and more preferably in the range of 0.1% by mass to 10% by mass based on the solid content of the chemical amplification type resist composition.

In order to reduce a change in performance with time from the exposure to the baking, the chemical amplification type resist composition according to the invention may contain the basic compound (N') different from the compound (N), as the basic compound.

As the basic compound (N'), preferably, compounds having structures indicated in Formulae (A') to (E') below can be included.

(49)

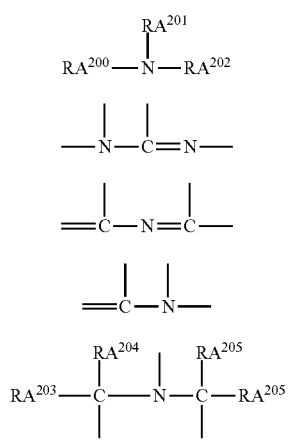

In General Formulae (A') and (E'), $RA^{200}$, $RA^{201}$, and $RA^{202}$ may be identical to or different from each other, and represent hydrogen atoms, alkyl groups (preferably having 1 to 20 carbon atoms), cycloalkyl groups (preferably, having 3 to 20 carbon atoms), or aryl groups (having 6 to 20 carbon atoms). Here, $RA^{201}$ and $RA^{202}$ may be combined with each other, so as to form a ring. $RA^{203}$, $RA^{204}$, $RA^{205}$, and $RA^{206}$ may be identical to or different from each other, and represent alkyl groups (preferably having 1 to 20 carbon atoms).

The alkyl group may have a substituent, and as the alkyl group having the substituent, an aminoalkyl group having 1 to 20 carbon atoms, a hydroxyalkyl group having 1 to 20 carbon atoms, or a cyanoalkyl group having 1 to 20 carbon atoms is preferable.

The alkyl groups in General Formulae (A') and (E') are preferably unsubstituted.

As the preferable specific examples of the basic compound (N'), guanidine, aminopyrrolidine, pyrazole, pyrazoline, piperazine, aminomorpholine, aminoalkylmorpholine, piperidine, and the like can be included. As more preferable specific examples, compounds having an imidazole structure, a diazabicyclo structure, an onium hydroxide structure, an onium carboxylate structure, a trialkylamine structure, an aniline structure, or a pyridine structure, an alkylamine derivative having a hydroxyl group and/or an ether bond, and an aniline derivative having a hydroxyl group and/or an ether bond can be included.

As the compound having the imidazole structure, imidazole, 2,4,5-triphenyl imidazole, benzimidazole, and the like are included. As the compound having the diazabicyclo structure, 1,4-diazabicyclo[2,2,2]octane, 1,5-diazabicyclo[4,3,0]nona-5-ene, 1,8-diazabicyclo[5,4,0]undec-7-ene, and the like are included. As the compound having the onium hydroxide structure, triarylsulfonium hydroxide, phenacyl sulfonium hydroxide, and sulfonium hydroxide having a 2-oxoalkyl group are included. Specifically, triphenylsulfonium hydroxide, tris(t-butylphenyl)sulfonium hydroxide, bis(t-butylphenyl)iodonium hydroxide, phenacyl thiophenium hydroxide, 2-oxopropyl thiophenium hydroxide, and the like are included. As the compound having an onium carboxylate structure, a compound in which an anion portion of the compound having an onium hydroxide structure becomes carboxylate, and, for example, acetate, adamantane-1-carboxylate, and perfluoroalkyl carboxylate are included. As the compound having a trialkylamine structure, tri(n-butyl)amine, tri(n-octyl)amine, and the like can be included. As the compound having an aniline structure, 2,6-diisopropyl aniline, N,N-dimethylaniline, N,N-dibutylaniline, N,N-dihexylaniline, and the like are included. As the alkylamine derivative having a hydroxyl group and/or an ether bond, ethanolamine, diethanolamine, triethanolamine, tris(methoxyethoxy ethyl)amine, and the like can be included. As the aniline derivative having a hydroxyl group and/or an ether bond, N,N-bis(hydroxyethyl)aniline and the like can be included.

As a preferable basic compound, an amine compound having a phenoxy group, an ammonium salt compound having a phenoxy group, an amine compound having a sulfonic acid ester group, and an ammonium salt compound having a sulfonic acid ester group can be further included. As specific examples thereof, the compounds (C1-1) to (C3-3) exemplified in [0066] of US2007/0224539A are included, but the invention is not limited thereto.

In addition, as a type of the basic compound, a nitrogen-containing organic compound having a group released by an action of an acid may be used. As an example of the compound, for example, specific examples of the compound are described below.

(50)

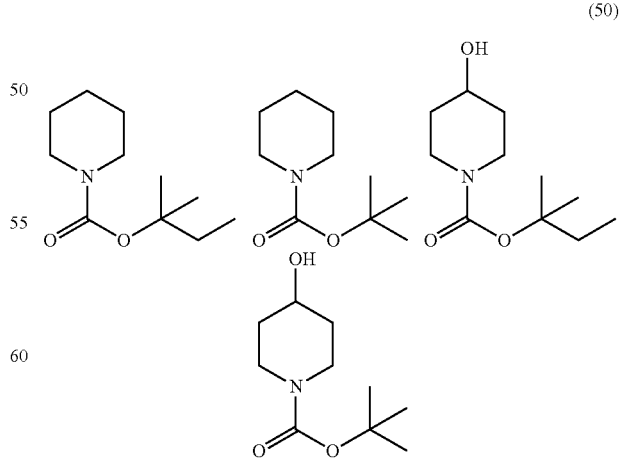

The compound described above can be synthesized by a method described in JP2009-199021A.

In addition, as the basic compound (N'), a compound having an amine oxide structure can be used. As specific examples thereof triethylamine pyridine N-oxide, tributyl amine N-oxide, triethanol amine N-oxide, tris(methoxyethyl)amine N-oxide, tris(2-(methoxymethoxy)ethyl)amine=oxide, 2,2',2"-nitrilotriethyl propionate N-oxide, N-2-(2-methoxyethoxy)methoxyethylmorpholine N-oxide, and an amine oxide compound disclosed in JP2008-102383A can be used.

The molecular weight of the basic compound (N') is preferably in the range of 250 to 2,000, and more preferably in the range of 400 to 1,000. In view of further reduction of LWR and uniformity of a local pattern dimension, the molecular weight of the basic compound is preferably 400 or greater, more preferably 500 or greater, and still more preferably 600 or greater.

The basic compound (N') may be used in combination with the compound (N) or may be used singly, or two or more types thereof may be used in combination.

The chemical amplification type resist composition according to the invention may not contain the basic compound (N'), but if chemical amplification type resist composition according to the invention contains the basic compound (N'), the used amount of the basic compound (N') is generally 0.001% by mass to 10% by mass, and preferably in the range of 0.01% by mass to 5% by mass based on the solid content of the chemical amplification type resist composition.

In addition, as the chemical amplification type resist composition according to the invention, compounds (hereinafter, referred to as a "betaine compound") having both of an onium salt structure and an acid anion structure in one molecule, such as a compound included in Formula (I) of JP2012-189977A, a compound expressed in Formula (I) of JP2013-6827A, a compound expressed in Formula (I) of JP2013-8020A, and a compound expressed in Formula (I) of JP2012-252124A are preferably used. As the onium salt structure, sulfonium, iodonium, and ammonium structures are included, and sulfonium or iodonium salt structures are preferable. As the acid anion structure, sulfonic acid anion or carboxylic acid anion is preferable. For example, examples of the compounds are as described below.

(51)

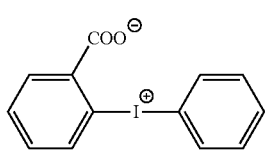

C1-1

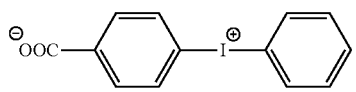

C1-2

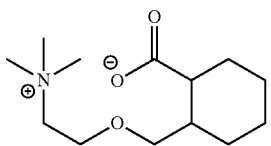

C1-3

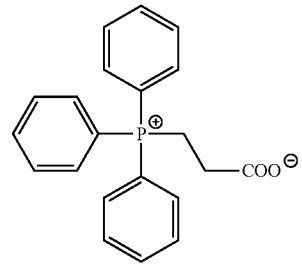

C1-4

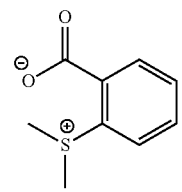

C1-5

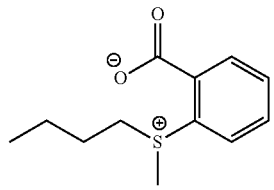

C1-6

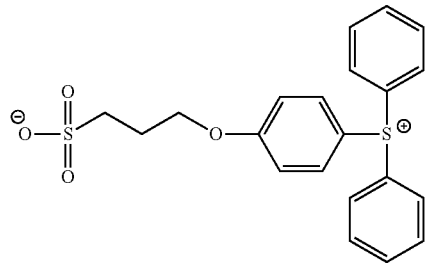

C1-7

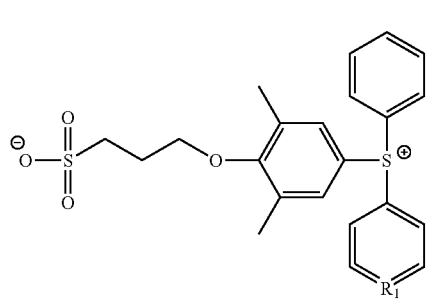

C1-8

[6] (F) Surfactant

The chemical amplification type resist composition according to the invention may not further contain a surfactant, but if the chemical amplification type resist composition according to the invention contains a surfactant, any one of fluorine and/or a silicon-based surfactant (fluorine-based surfactant, silicon-based surfactant, and surfactant having both of fluorine atom and silicon atom) or two or more types thereof are preferably contained.

If the chemical amplification type resist composition according to the invention contains a surfactant, when a exposure light source having 250 nm or lower, particularly 220 nm or lower is used, a resist pattern having adhesive properties and fewer developing defects can be applied at favorable sensitivity and resolutions.

As the fluorine-based and/or silicon-based surfactant, a surfactant disclosed in [0276] of US2008/0248425A is included, and for example, EFTOP EF301 and EF303, (manufactured by Shin Akita Chemicals Corp.), Florad FC430, 431, and 4430 (manufactured by Sumitomo 3M Ltd.), Megaface F171, F173, F176, F189, F113, F110, F177, F120, and R08 (manufactured by DIC Corporation), Surflon S-382, SC101, 102, 103, 104, 105, 106, and KH-20 (manufactured by Asahi Glass Co., Ltd.), Troysol S-366 (manufactured by Troy Corporation), GF-300 and GF-150 (manufactured by Toagosei Co., Ltd.), Surflon S-393 (manufactured by AGC Seimi Chemical Co., Ltd.), EFTOP EF121, EF122A, EF122B, RF122C, EF125M, EF135M, EF351, EF352, EF801, EF802, and EF601 (manufactured by JEMCO Inc.), PF636, PF656, PF6320, and PF6520 (OMNOVA Solutions Inc.), and FTX-204G, 208G, 218G, 230G, 204D, 208D, 212D, 218D, and 222D (manufactured by NEOS COMPANY LIMITED) are included. In addition, polysiloxane polymer KP-341 (manufactured by Shin-Etsu Chemical Co., Ltd.) is also used as a silicon-based surfactant.

In addition, as the surfactant, in addition to well-known products as described above, a surfactant using a polymer having a fluoro aliphatic group derived from a fluoro aliphatic compound manufactured by a telomerization method (also referred to as a "telomer method") or an oligomerization method (also referred to as a "oligomer method") can be used. The fluoro aliphatic compound can be synthesized by a method disclosed in JP2002-90991A.

As the surfactant corresponding to the above, Megaface F178, F-470, F-473, F-475, F-476, and F-472 (manufactured by DIC Corporation), a copolymer of acrylate (or methacrylate) having a $C_6F_{13}$ group and (poly(oxyalkylene)) acrylate (or methacrylate), and a copolymer of acrylate (or methacrylate) having a $C_3F_7$ group, (poly(oxyethylene)) acrylate (or methacrylate), and (poly(oxypropylene)) acrylate (or methacrylate) are included.

In addition, a surfactant other than fluorine-based and/or silicon-based surfactants disclosed in [0280] of US2008/0248425A can be used.

These surfactants may be used singly, or two or more types thereof may be used in combination.

If the chemical amplification type resist composition contains a surfactant, the used amount of the surfactant is preferably in the range of 0.0001% by mass to 2% by mass and more preferably in the range of 0.0005% by mass to 1% by mass with respect to the total amount (except for the solvent) of the chemical amplification type resist composition.

Meanwhile, if the addition amount of the surfactant is 10 ppm or lower with respect to the total amount (except for the solvent) of the chemical amplification type resist composition, the uneven distribution properties of the surface of the hydrophobic resin increase, and accordingly, the resist film surface can become more hydrophobic. Therefore, the conformability to water at the time of liquid immersion exposure can be improved.

[7] (G) Other Additives

The chemical amplification type resist composition according to the invention may contain carboxylic acid onium salt. As the carboxylic acid onium salt, a product disclosed in [0605] to [0606] of US2008/0187860A can be included.

If the chemical amplification type resist composition contains carboxylic acid onium salt, the content thereof is generally in the range of 0.1% by mass to 20% by mass, preferably in the range of 0.5% by mass to 10% by mass, and more preferably in the range of 1% by mass to 7% by mass with respect to the total solid content of the composition.

In addition, the chemical amplification type resist composition according to the invention may include a so-called acid-proliferation agent, if necessary. The acid-proliferation agent is preferably used particularly when the pattern forming method according to the invention is performed by EUV exposure or the irradiation with an electron ray. The specific examples of the acid-proliferation agent are not particularly limited, but, for example, the following are included.

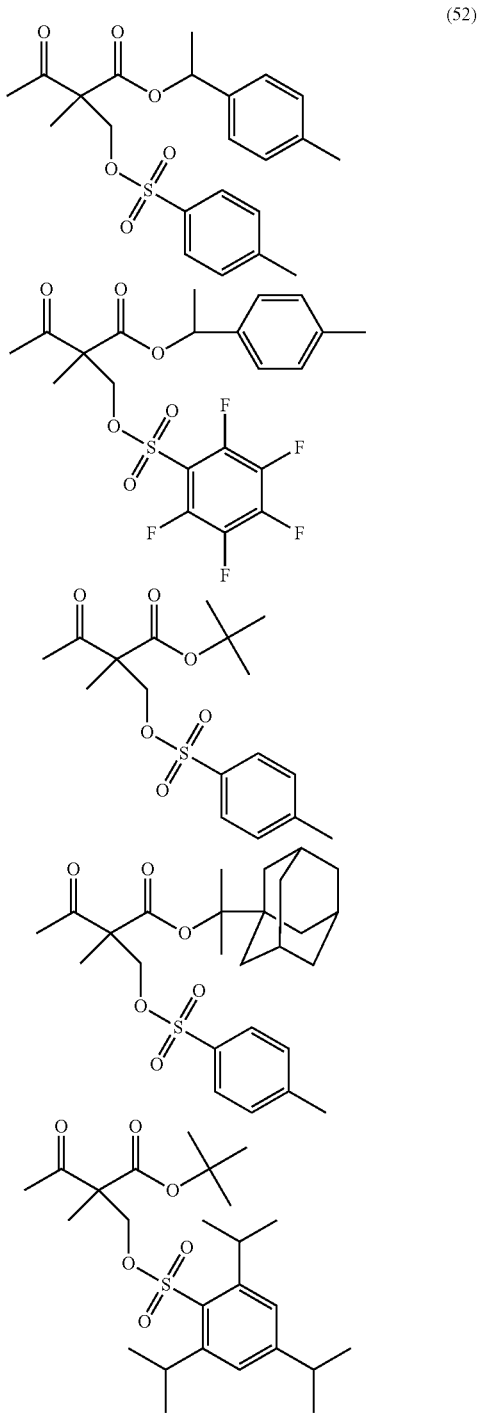

(52)

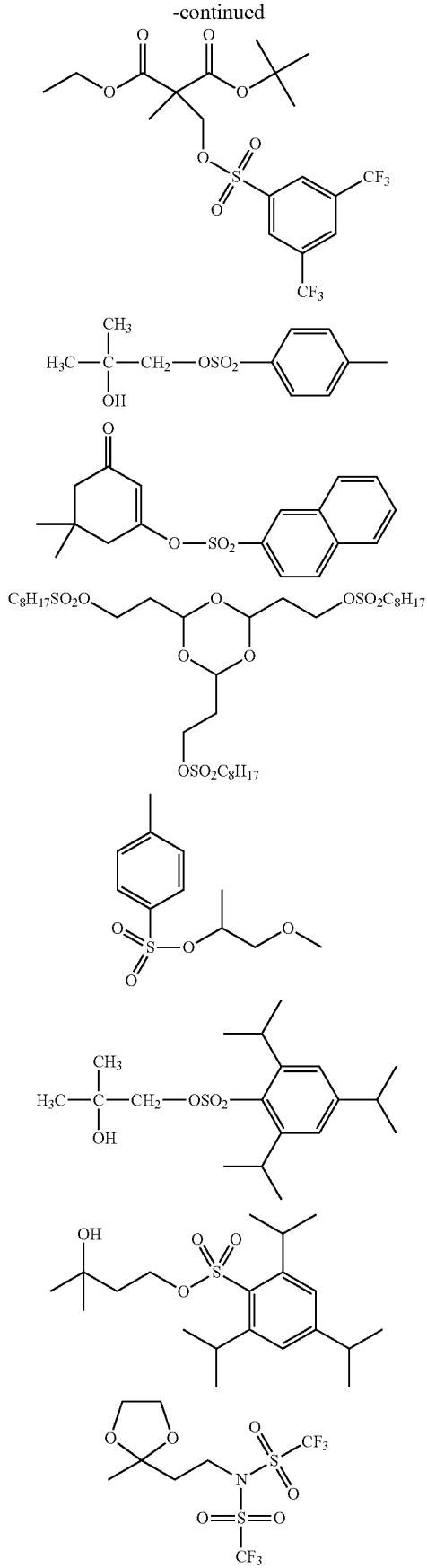
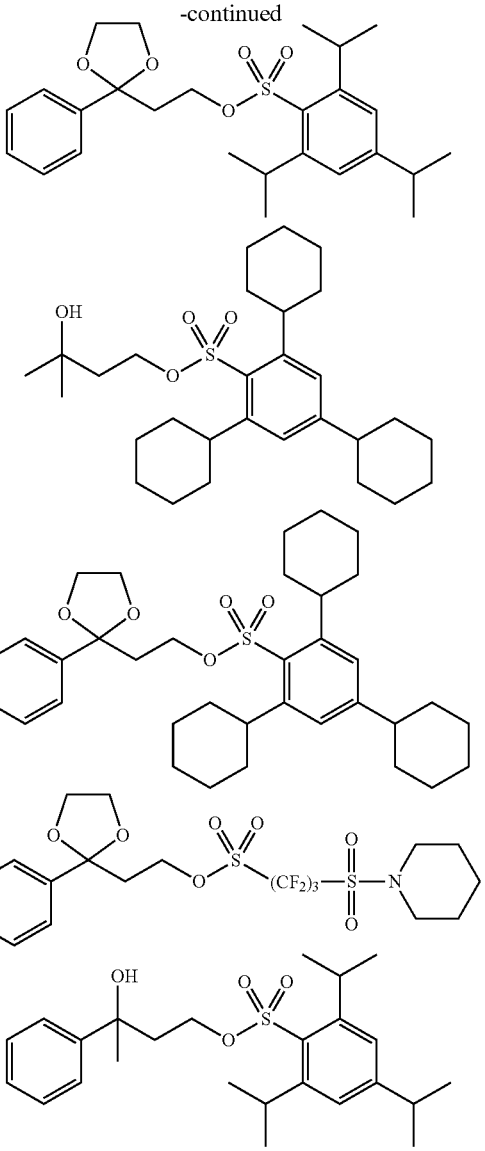

In the chemical amplification type resist composition according to the invention, if necessary, a dye, a plasticizer, a photosensitizer, a light absorber, an alkali-soluble resin, a dissolution inhibitor, a compound (for example, a phenol compound having a molecular weight of 1,000 or lower, alicyclic or aliphatic compound having a carboxyl group) that promotes solubility in the developer, and the like can be further contained.

In view of improvement of resolving power, the chemical amplification type resist composition according to the invention is used preferably in a film thickness in the range of 30 nm to 250 nm and more preferably in a film thickness in the range of 30 nm to 200 nm.

The solid content density of the chemical amplification type resist composition according to the invention is generally in the range of 1.0% by mass to 10% by mass, more preferably in the range of 2.0% by mass to 5.7% by mass, and still more preferably in the range of 2.0% by mass to 5.3% by mass. If the solid content density is in the range described above, the resist solution can be evenly applied on the substrate.

The solid content density represents a weight percentage of weights of the resist components other than the solvent, with respect to the total weight of the chemical amplification type resist composition.

The chemical amplification type resist composition according to the invention is used by dissolving the component in a predetermined organic solvent, preferably in the mixed solvent described above, performing filter filtration, and performing application on a predetermined support body (substrate). The pore size of the filter used in the filter filtration is 0.1 μm or lower, more preferably 0.05 μm or lower, and still more preferably 0.03 μm or lower, and preferably made of polytetrafluoroethylene, polyethylene, or nylon. In the filter filtration, for example, as disclosed in JP2002-62667A, cyclical filtration may be performed, or filtration may be performed by connecting plural kinds of filters in series or in parallel. In addition, the composition may be filtrated plural times. Further, before or after the filter filtration, a deaeration treatment or the like may be performed on the composition.

In general, the pattern obtained in the pattern forming method according to the invention is preferably used as an etching mask of a semiconductor device and the like, but may be used for other uses. As the other uses, for example, a guide pattern formation (for example, see ACS Nano Vol. 4 No. 8 Pages 4815 to 4823) in Directed Self-Assembly (DSA), a use as a core of a so-called spacer process (for example, see JP-H3-270227A and JP2013-164509A), and the like are included.

The invention also relates to the method for manufacturing the electronic device including the aforementioned pattern forming method according to the invention and an electronic device manufactured by the manufacturing method for the same.

The electronic device according to the invention is appropriately mounted on electric or electronic apparatuses (household electric devices, OA or media-related apparatuses, optical apparatuses, telecommunication apparatuses, and the like).

EXAMPLES

The organic processing fluid is manufactured by using the organic processing fluid manufacturing system 100 described above.

An inner wall that comes into contact with the fluid of the fluid tank 11 and the flow paths (pipes, seal portions, joint members, and the like) outside the filtration device 21 described above all are made of fluorine resins (PTFE, PFA, and the like) or metal, in which it is confirmed that metal elution is not performed or lining is performed with these raw materials.

Example 1

Circulation Line Washing

One UltiKleen 50-nm PTFE filter (Product Name: ABF1UCFD3EH1; pore size of 50 nm; filtration surface area per one filter of 1.2 m²) manufactured by Pall Corporation was set as the first stage filter F1 in a first filter housing H1 wound with a water jacket at 23° C., and one 20-nm PTFE filter (Product Name: ABF1UCF3EH1; pore size of 20 nm; filtration surface area per one filter of 1.2 m²) manufactured by Pall Corporation was set as the second stage filter F2 in a second filter housing H2 wound with a water jacket.

Butyl acetate in an amount in which the circulation line of the organic processing fluid manufacturing system 100 was able to be sufficiently filled was put into the fluid tank 11, a flow rate adjusting valve 12 was opened, the flow switching valve 15 was set to the circulation side, the pump 16 was driven, butyl acetate in an amount corresponding to five times of a circulation line volume was circulated in the circulation line, the circulation line was washed, the flow switching valve 15 was set to the extraction side, and butyl acetate in the circulation line was discharged.

In addition, butyl acetate in the circulation line was discharged also from the drains D1, D2, and D3, as much as possible.

The washing process of the circulation line above was performed two times.

<Preparation of Fluid to be Filtrated>

New butyl acetate was put into the fluid tank 11, and the temperature of the fluid to be filtrated was set to 23° C. by a temperature regulator accompanied by the fluid tank 11.

At the same time, the temperature of the water jacket in the first filter housing H1 and the second filter housing H2 was set to 23° C.

The flow rate adjusting valve 12 was opened, the flow switching valve 15 was set to the circulation side, the pump 16 was driven, and butyl acetate was circulated in the circulation line of the organic processing fluid manufacturing system 100 while temperature regulator accompanied by the fluid tank 11 was adjusted until the temperature indicated by the pressure/flow rate/fluid temperature meter 13 became the temperature (23° C.) set before the filtration.

After the temperature indicated by the pressure/flow rate/fluid temperature meter 13 was checked to be 23° C., the pump 16 is stopped, while the flow rate adjusting valve 12 and the temperature regulator accompanied by the fluid tank 11 were adjusted, the fluid extracted from the fluid extraction opening 17 was set to the organic processing fluid for evaluation, such that the flow switching valve 15 was substituted to the extraction side, and the filtration pressure, the flow rate, and the temperature indicated by the pressure/flow rate/fluid temperature meter 13 became 0.05 MPa, 2.5 L/min, and 23° C., respectively.

<Wet Particle Evaluation>

The number of particles (N1) on a silicon wafer of 8 inches was examined by a wafer defect evaluation apparatus ComPLUS3T (examination mode 30 T) manufactured by Applied Materials, Inc. which is installed in a clean room of a class 1000.

When 5 mL of butyl acetate as the organic processing fluid for the evaluation was discharged on the silicon wafer, and the silicon wafer was rotated at 1,000 revolutions/min for 1.6 seconds, butyl acetate was dispersed on the silicon wafer, settling was performed for 20 seconds, and spin drying was performed at 2,000 revolutions/min for 20 seconds.

After 24 hours, the number of particles (N2) on the silicon wafer was examined by a wafer defect evaluation apparatus ComPLUS3T (examination mode 30 T) manufactured by Applied Materials, Inc., and N2−N1 was set to be the number of wet particles (N).

The evaluation results were presented in Table 5.

Examples 2 to 8 and Comparative Examples 1 to 7

Except for setting conditions as presented in Table 4, the organic processing fluid was manufactured in the same manner as in Example 1, and the wet particles were evaluated. In Example 8, two first stage filters F1 were connected to each other in parallel inside of the first filter housing H1, and two second stage filters F2 were connected to each other in parallel inside of the second filter housing H2. The evaluation results were presented in Table 5.

TABLE 4

| | | First stage filter F1 | | | | | Second stage filter F2 | | | | |
|---|---|---|---|---|---|---|---|---|---|---|---|
| Example | Type of fluid | Name of type (all manufactured by Pall Corporation) | Number of items (Parallel arrangement if plural) | Raw material of filtration filter film | Pore size (nm) | Filtration surface area per one filter (m²) | Name of type (all manufactured by Pall Corporation) | Number of items (Parallel arrangement if plural) | Raw material of filtration filter film | Pore size (nm) | Filtration surface area per one filter (m²) |
| Example 1 | n-butyl acetate | ABF1UCFD3EH1 | One | PTFE | 50 | 1.2 | ABF1UCF3EH1 | One | PTFE | 20 | 1.2 |
| Example 2 | 4-methyl-2-pentanol | ABF1UCFD3EH1 | One | PTFE | 50 | 1.2 | ABF1UCF3EH1 | One | PTFE | 20 | 1.2 |
| Example 3 | 4-methyl-2-pentanol | ABF1UCFD3EH1 | One | PTFE | 50 | 1.2 | ABD1UG0013EH1 | One | PE | 10 | 1.3 |
| Example 4 | methyl amyl ketone | ABF1UCFD3EH1 | One | PTFE | 50 | 1.2 | ABD1UG53EH1 | One | PE | 5 | 1.3 |
| Example 5 | 4-methyl-2-pentanol | ABF1UCFD3EH1 | One | PTFE | 50 | 1.2 | ABD1UG0013EH1 | One | PE | 10 | 1.3 |
| Example 6 | n-butyl acetate | ABF1UCFD3EH1 | One | PTFE | 50 | 1.2 | ABD1AN013EH1 | One | Nylon | 10 | 1.3 |
| Example 7 | 4-methyl-2-pentanol | ABF1UCFD3EH1 | One | PTFE | 50 | 1.2 | ABD1UG0013EH1 | One | PE | 10 | 1.3 |
| Example 8 | n-butyl acetate | ABF1UCFD3EH1 | Two | PTFE | 50 | 1.2 | ABF1UCF3EH1 | Two | PTFE | 20 | 1.2 |
| Comparative Example 1 | n-butyl acetate | ABD1UG0053EH1 | One | PE | 50 | 1.4 | ABD1UG0013EH1 | One | PE | 10 | 1.3 |
| Comparative Example 2 | n-butyl acetate | ABD1UG0053EH1 | One | PE | 50 | 1.4 | ABD1UG0013EH1 | One | PE | 10 | 1.3 |
| Comparative Example 3 | n-butyl acetate | ABD1UG0053EH1 | One | PE | 50 | 1.4 | ABD1UG0013EH1 | One | PE | 10 | 1.3 |
| Comparative Example 4 | 4-methyl-2-pentanol | ABF1UCFD3EH1 | One | PTFE | 50 | 1.4 | ABD1UG0013EH1 | One | PE | 10 | 1.3 |
| Comparative Example 5 | 4-methyl-2-pentanol | ABF1UCFD3EH1 | One | PTFE | 50 | 1.4 | ABD1UG0013EH1 | One | PE | 10 | 1.3 |
| Comparative Example 6 | n-butyl acetate | ABD1UG0053EH1 | One | PE | 50 | 1.4 | ABD1UG0013EH1 | One | PE | 10 | 1.3 |
| Comparative Example 7 | n-butyl acetate | None | | | | | ABD1UG1003EH1 | One | PE | 1000 | 1.1 |

| Example | Filtration pressure of filtration device indicated by the pressure/flow rate/fluid temperature meter 13 (MPa) | Temperature setting value of fluid to be filtrated in the tank 11 (° C.) | $T_I$ (° C.) | Set temperature of filter housings H1 and H2 (° C.) | $\|T_I - T_o\|$ (Absolute value of difference between temperature indicated by pressure/flow rate/fluid temperature meter 13 and temperature indicated by fluid temperature meter 14) (° C.) | Flow rate of fluid indicated by pressure/flow rate/fluid temperature meter 13 (L/min) | Filtration speed of filtration device (L/min/m²) |
|---|---|---|---|---|---|---|---|
| Example 1 | 0.05 | 23 | 23 | 23 | 0 | 2.5 | 1.0 |
| Example 2 | 0.06 | 23 | 23 | 23 | 0 | 1.5 | 0.6 |
| Example 3 | 0.08 | 23 | 23 | 23 | 0 | 1.4 | 0.6 |
| Example 4 | 0.03 | 28 | 28 | 28 | 0 | 2.0 | 0.8 |
| Example 5 | 0.06 | 30 | 30 | 30 | 0 | 1.5 | 0.6 |
| Example 6 | 0.06 | 15 | 15 | 15 | 1 | 2.5 | 1.0 |
| Example 7 | 0.08 | 25 | 25 | 20 | 3 | 1.5 | 0.6 |
| Example 8 | 0.06 | 23 | 23 | 23 | 0 | 5.0 | 1.0 |
| Comparative Example 1 | 0.15 | 45 | 45 | 45 | 0 | 3.5 | 1.3 |
| Comparative Example 2 | 0.05 | 45 | 45 | 35 | 6 | 2.7 | 1.0 |
| Comparative Example 3 | 0.05 | 23 | 23 | 45 | 13 | 2.7 | 1.0 |
| Comparative Example 4 | 0.05 | 15 | 15 | 15 | 1 | 0.3 | 0.1 |
| Comparative Example 5 | 0.30 | 15 | 15 | 15 | 1 | 1.4 | 0.5 |
| Comparative Example 6 | 0.01 | 23 | 23 | 23 | 0 | 0.8 | 0.3 |
| Comparative Example 7 | 0.11 | 23 | 23 | 23 | 0 | 10.0 | 9.1 |

TABLE 5

| | Number of particles (N) |
|---|---|
| Example 1 | 20 |
| Example 2 | 10 |
| Example 3 | 60 |
| Example 4 | 80 |
| Example 5 | 100 |
| Example 6 | 70 |
| Example 7 | 120 |
| Example 8 | 20 |
| Comparative Example 1 | 35854 |
| Comparative Example 2 | 29287 |
| Comparative Example 3 | 55864 |
| Comparative Example 4 | 7476 |
| Comparative Example 5 | 476 |
| Comparative Example 6 | 23599 |
| Comparative Example 7 | 17581 |

As described above, in manufacturing methods of Examples 1 to 8 which satisfied three conditions of (i) the absolute value ($|T_f-T_o|$) of the difference between the temperature ($T_f$) of the fluid in the fluid input portion 21a and the temperature ($T_o$) of the fluid in the fluid output portion 21b was 3° C. or lower, (ii) a filtration speed of the fluid in the filtration device 21 was 0.5 L/min/m² or higher, and (iii) a filtration pressure by the fluid in the filtration device 21 was 0.1 MPa or lower, the number of particles was greatly reduced, compared with manufacturing methods of Comparative Examples 1 to 7 which did not satisfy at least one of the conditions.

Examples 9 to 15

Synthesization Example (Synthesization of Resin A-1)

102.3 parts by mass of cyclohexanone was baked to 80° C. under a nitrogen gas stream. While the fluid was stirred, a mixed solution of 22.2 parts by mass of a monomer expressed by Structural Formula M-1 below, 22.8 parts by mass of a monomer expressed by Structural Formula M-2 below, 6.6 parts by mass of a monomer expressed by Structural Formula M-3 below, 189.9 parts by mass of cyclohexanone, and 2.40 parts by mass of 2,2'-azobis dimethyl isoacetate [V-601, manufactured by Wako Pure Chemical Industries, Ltd.] were dropped for 5 hours. After the dripping was completed, stirring was further performed for 2 hours at 80° C. After the reaction fluid was cooled, reprecipitation was performed with a large amount of hexane/ethyl acetate (mass ratio 9:1), filtration was performed, and the obtained solid matter was vacuum-dried, and thus 41.1 parts by mass of a resin (A-1) according to the invention was obtained.

(53)

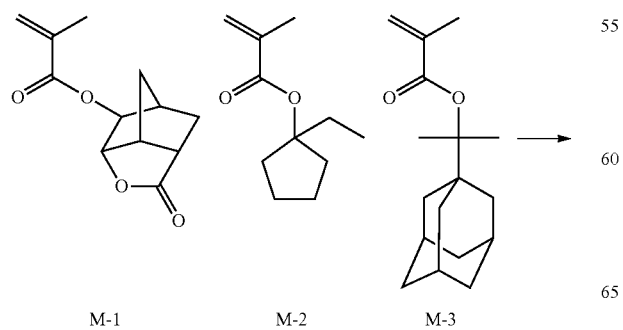

M-1    M-2    M-3

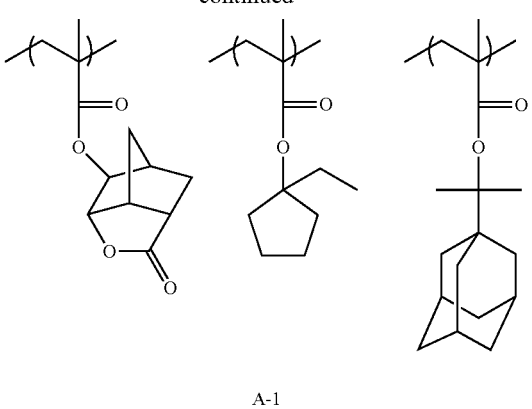

A-1

The weight average molecular weight (Mw: in terms of polystyrene) obtained by GPC (Carrier: tetrahydrofuran (THF)) of the obtained resin was Mw=9,500, and the dispersion degree was Mw/Mn=1.60. The composition ratio (molar ratio) measured by ¹³C-NMR was 40/50/10.

<Resin (A)>

Hereinafter, in the same manner, resins A-2 and A-3 were synthesized. Hereinafter, composition ratios (molar ratios), weight average molecular weights (Mw), and dispersion degrees (Mw/Mn) of repeating units in the resins A-2 and A-3 together with the resin A-1 are presented below.

(54)

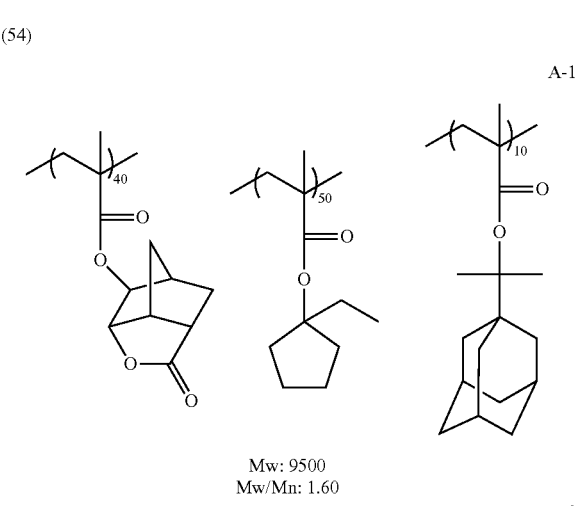

A-1

Mw: 9500
Mw/Mn: 1.60

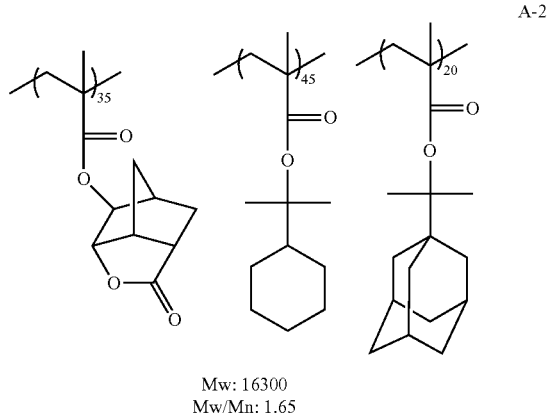

A-2

Mw: 16300
Mw/Mn: 1.65

-continued
A-3
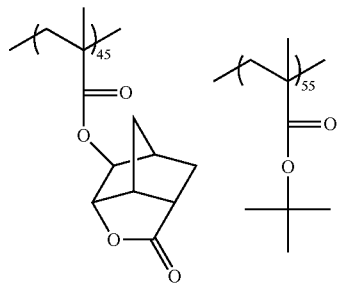
Mw: 18000
Mw/Mn: 1.70
<Acid Generating Agent>
As the acid generating agent, following compounds were used.
(55)
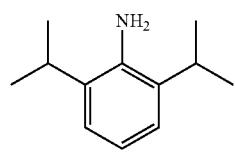
PAG-1
(56)
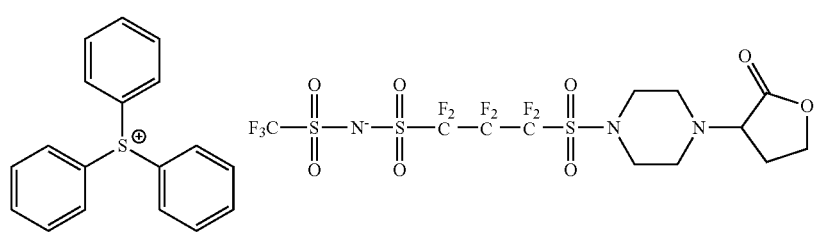
-continued
PAG-2
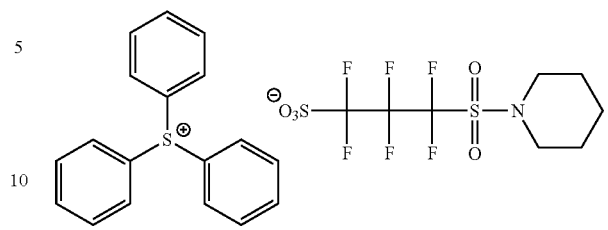
PAG-3
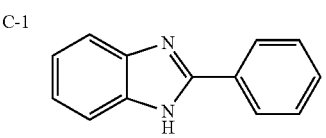
<Basic Compound>
As the basic compound, following compounds were used.
C-1
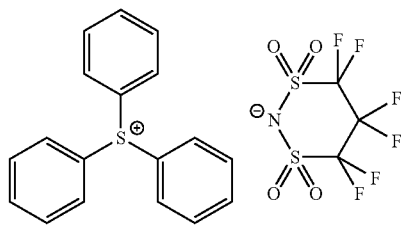
C-2
C-3

151

<Hydrophobic Resin>

In the same manner as in the resin (A), resins D-1 to D-3 were synthesized. Composition ratios (molar ratios), weight average molecular weights (Mw), and dispersion degrees (Mw/Mn) of the repeating units in the resins D-1 to D-3 are presented below.

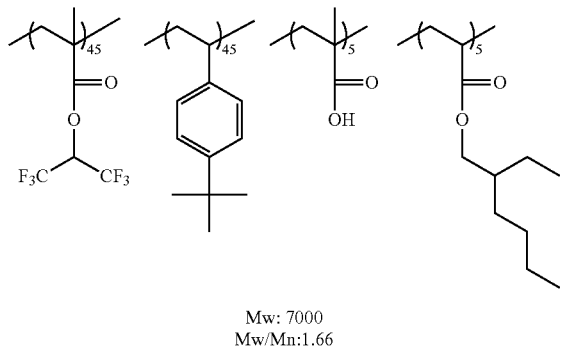

Mw: 7000
Mw/Mn: 1.66

-continued

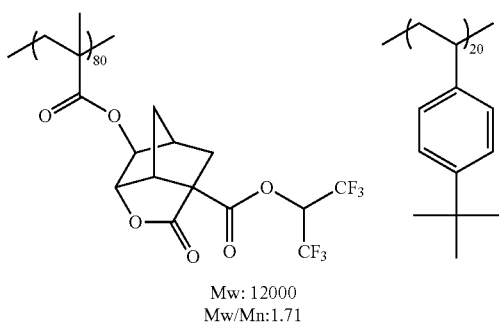

Mw: 12000
Mw/Mn: 1.71

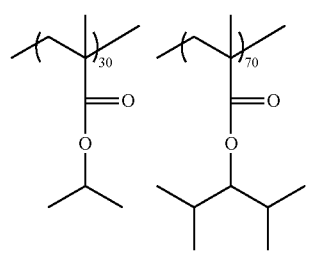

Mw: 22000
Mw/Mn: 1.67

152

<Surfactant>

As the surfactant, the following were used.
W-1: Megaface F176 (manufactured by DIC Corporation; fluorine-based surfactant)
W-2: Megaface R08 (manufactured by DIC Corporation; fluorine and silicon-based surfactant)

<Solvent>

As the solvent, the following were used.
SL-1: Propylene glycol monomethyl ether acetate (PGMEA)
SL-2: Propylene glycol monomethyl ether (PGME)

<Lithography Evaluation 1>

3.8% by mass of components presented in Table 6 below were dissolved in a solvent in Table 6 as a solid content, the respective components were filtrated with a polyethylene filter having a pore size of 0.03 μm, and thus chemical amplification type resist compositions were prepared.

An organic reflection preventive film ARC29SR (manufactured by Nissan Chemical Industries, Ltd.) was applied on the silicon wafer, baking was performed for 60 seconds at 205° C., and a reflection preventive film having a film thickness of 95 nm was formed. Further, the chemical amplification type resist composition prepared as described above was applied, baking was performed for 60 seconds at 100° C., and a chemical amplification type resist film (resist film 1) having a film thickness of 90 nm was formed.

TABLE 6

| Chemical amplification type resist composition | Resin (A) | (g) | Acid generating agent (B) | (g) | Basic compound | (g) | Resin (D) | (g) | Solvent | Mass ratio | Surfactant | (g) |
|---|---|---|---|---|---|---|---|---|---|---|---|---|
| I-1 | A-1 | 10 | PAG-1 | 0.80 | C-1 | 0.14 | D-1 | 0.6 | SL-1/SL-2 | 80/20 | W-1 | 0.003 |
| I-2 | A-2 | 10 | PAG-2 | 0.90 | C-2 | 0.14 | D-2 | 2.0 | SL-1 | 100 | W-2 | 0.003 |
| I-3 | A-3 | 10 | PAG-3 | 0.45 | C-3 | 0.45 | D-3 | 4.0 | SL-1/SL-2 | 80/20 | None | — |

Example 9

Development/Rinse Process

The resist film 1 formed of a chemical amplification type resist composition I-1 of Table 6 was pattern-exposed through a halftone mask by using an ArF excimer laser immersion scanner [manufactured by ASML; XT1700i, NA1.20, Dipole (outer σ: 0.981/inner σ: 0.895), Y deflection]. Ultrapure water was used as the immersion fluid. Thereafter, baking was performed for 60 seconds at 105° C. Subsequently, development was performed for 30 seconds using butyl acetate manufactured by the manufacturing method of Example 1 as the developer, and rinsing was performed for 20 seconds using 4-methyl-2-pentanol manufactured by the manufacturing method of Example 2 as the rinse fluid, and thus a pattern (resist pattern substrate 1) was obtained.

Example 10

Development/Rinseless Process

The resist film 1 formed by a chemical amplification type resist composition I-2 of Table 6 was pattern-exposed through a halftone mask by using the ArF excimer laser immersion scanner [manufactured by ASML; XT1700i, NA1.20, Dipole (outer σ: 0.981/inner σ: 0.895), Y deflection]. Ultrapure water was used as the immersion fluid.

Thereafter, baking was performed for 60 seconds at 105° C. Subsequently, development was performed for 30 seconds using butyl acetate manufactured by the manufacturing method of Example 6 as the developer, spin drying was performed at 2,000 revolutions/min for 20 seconds, and thus a pattern (resist pattern substrate 2) was obtained.

Example 11

Development/Rinse Process

The resist film 1 formed by a chemical amplification type resist composition I-3 of Table 6 was pattern-exposed through a halftone mask by using the ArF excimer laser immersion scanner [manufactured by ASML; XT1700i, NA1.20, Dipole (outer σ: 0.981/inner σ: 0.895), Y deflection]. Ultrapure water was used as the immersion fluid. Thereafter, baking was performed for 60 seconds at 105° C. Subsequently, development was performed for 30 seconds using butyl acetate manufactured by the manufacturing method of Example 8 as the developer, and rinsing was performed for 2 seconds using butyl acetate manufactured by the manufacturing method of Example 1 as the rinse fluid, and thus a pattern (resist pattern substrate 3) was obtained.

The resist pattern substrates 1 to 3 were observed using a length measurement scanning electron microscope (CG4100 manufactured by Hitachi, Ltd.), and it was confirmed that 45 nm patterns of all substrates which have line sizes and space sizes of 1:1 were satisfactorily formed without being ruined.

was formed. Further, the resist compositions were applied thereon, baking was performed for 60 seconds at 100° C., and a chemical amplification type resist film (resist film 2) having a film thickness of 90 nm was formed.

Example 12

Development/Rinse Process

The resist film 2 was pattern-exposed through a halftone mask by using the ArF excimer laser immersion scanner [manufactured by ASML; XT1700i, NA1.20, Dipole (outer σ: 0.981/inner σ: 0.895), Y deflection]. Ultrapure water was used as the immersion fluid. Thereafter, baking was performed for 60 seconds at 105° C. Subsequently, development was performed for 30 seconds using the developer (that is, butyl acetate manufactured by the manufacturing method of Example 1) by the application developing device, rinsing was performed for 20 seconds using the rinse fluid (that is, 4-methyl-2-pentanol manufactured by the manufacturing method of Example 3), and thus a pattern (resist pattern substrate 4) was obtained.

Example 13

Development/Rinseless Process

The resist film 2 was pattern-exposed through a halftone mask by using the ArF excimer laser immersion scanner [manufactured by ASML; XT1700i, NA1.20, Dipole (outer

TABLE 7

| Example | Composition (I) | Developer | Rinse fluid |
|---|---|---|---|
| Example 9 | I-1 | Butyl acetate obtained by the manufacturing method of Example 1 | 4-methyl-2-pentanol obtained by the manufacturing method of Example 2 |
| Example 10 | I-2 | Butyl acetate obtained by the manufacturing method of Example 6 | — |
| Example 11 | I-3 | Butyl acetate obtained by the manufacturing method of Example 8 | Butyl acetate obtained by the manufacturing method of Example 1 |

<Lithography Evaluation 2>

A container that stores the resist composition having the same composition as the resist composition I-1 of Table 6 was connected to a resist line of an application developing device (RF³ˢ manufactured by SOKUDO).

In addition, an 18-L canister can that stores butyl acetate manufactured by the manufacturing method of Example 1 and used as the developer was connected to the application developing device.

In addition, an 18-L canister can that stores 4-methyl-2-pentanol manufactured by the manufacturing method of Example 3 and used as the rinse fluid was connected to the application developing device.

As POU filters for the developer and the rinse fluid respectively, Optimizer ST-L (Product Number: AWATM-LKM1) manufactured by Entegris, Inc. was mounted on the application developing device, and then air bleeding of the filters was performed by a general method in an application developing device, and continuously 30-L processing fluids (respectively for developer and rinse fluid) were caused to pass through the POU filters.

An organic reflection preventive film ARC29SR (manufactured by Nissan Chemical Industries, Ltd.) was applied on the silicon wafer by using the application developing device, baking was performed for 60 seconds at 205° C., and a reflection preventive film having a film thickness of 95 nm σ: 0.981/inner σ: 0.895), Y deflection]. Ultrapure water was used as the immersion fluid. Thereafter, baking was performed for 60 seconds at 105° C. Subsequently, development was performed for 30 seconds using the developer (that is, butyl acetate manufactured by the manufacturing method of Example 1) by the application developing device, spin drying was performed at 2,000 revolutions/min for 20 seconds, and thus a pattern (resist pattern substrate 5) was obtained.

The resist pattern substrates 4 and 5 were observed using the length measurement scanning electron microscope (CG4100 manufactured by Hitachi, Ltd.), and it was confirmed that 45 nm patterns of all substrates which have line sizes and space sizes of 1:1 were satisfactorily formed without being ruined.

Example 14

Preparation was performed with the same compositions as those in Example 8, except that the basic compound C-3 used in the chemical amplification type resist composition I-3 was substituted to betaine compounds C1-1 to C1-8, and evaluation was performed in the same step as Example 11, so as to form patterns.

Example 15

In Example 9, evaluation was performed in the same manner except that tri n-octylamine was added to butyl acetate such that the amount becomes 2% by mass with respect to the total amount of the developer was added to butyl acetate, right before butyl acetate was connected to the application developing device, so as to form patterns.

Examples 16 and 17

Resist Preparation

Components presented in Table 8 were dissolved in solvents presented in Table 8, such that the solid content became 1.6% by mass, and each of the components was filtrated with a polyethylene filter having a pore size of 0.05 µm, so as to prepare active ray-sensitive or radiant ray-sensitive resin compositions (chemical amplification type resist compositions) (I-4) and (I-5).

TABLE 8

| Chemical amplification type resist composition | Resin (A) | (g) | Acid generating agent (B) | (g) | Basic compound | (g) | Solvent | Mass ratio | Surfactant | (g) |
|---|---|---|---|---|---|---|---|---|---|---|
| I-4 | A-4 | 10 | PAG-4 | 3.00 | C-3 | 0.90 | SL-1/SL-2 | 60/40 | W-1 | 0.003 |
| I-5 | A-5 | 10 | PAG-5 | 3.00 | C-3 | 0.90 | SL-1/SL-2 | 60/40 | W-1 | 0.003 |

In relation to symbols in Table 8, symbols which are not described above are as follows.

(58)

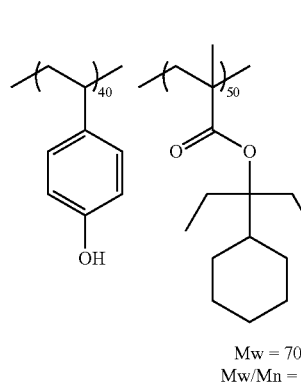
A-4
Mw = 7000
Mw/Mn = 1.52

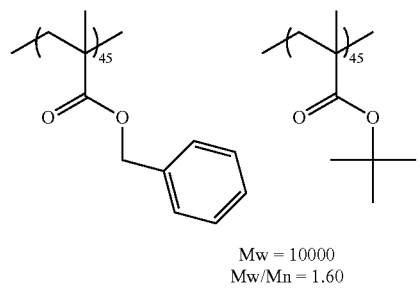
A-5
Mw = 10000
Mw/Mn = 1.60

(59)

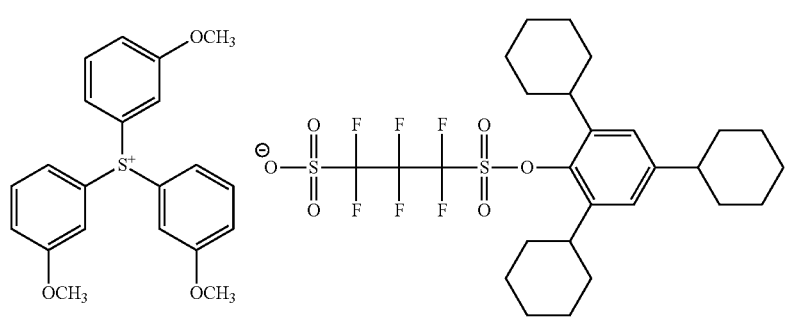
PAG-4

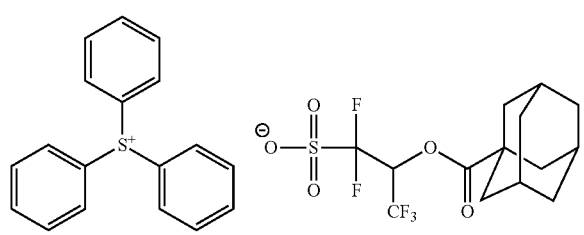
PAG-5

Example 16

Formation of Resist Film

The chemical amplification type resist composition I-4 of Table 8 was applied on a Si wafer subjected to a hexamethyldisilazane (HMDS) treatment in advance, drying was performed on a hot plate at 100° C., for 60 seconds, and thus a resist film having a film thickness of 50 nm was obtained.
(Formation of Resist Pattern)
EUV exposure was performed on the wafer on which the resist film is applied. After the irradiation, baking was performed at 110° C. for 60 seconds on a hot plate, paddling was performed by using butyl acetate manufactured by the manufacturing method of Example 1, and development was performed for 30 seconds, so as to form a pattern.

Example 17

In the same manner as in Example 16, a resist pattern was formed with the chemical amplification type resist composition I-5 in Table 8.

According to the invention, a method for manufacturing an organic processing fluid for patterning of a chemical amplification type resist film, an organic processing fluid for patterning of the chemical amplification type resist film using the same, a pattern forming method, a method for manufacturing an electronic device, and an electronic device, which can reduce the generation of particles in the technique for forming the negative pattern that forms a fine (for example, nodes of 30 nm or lower) pattern particularly by using the organic developer can be provided.

The invention is described in detail with reference to specific embodiments, but it is obvious to a person having ordinary skill in the art that various changes or modifications can be performed without departing from the spirit or the scope of the invention.

This application claims priority based on JP2013-076735, filed on Apr. 2, 2013, and the content thereof is incorporated herein by reference in its entirety.

EXPLANATION OF REFERENCES

11: fluid tank
12: fluid amount adjusting valve
13: pressure/flow rate/fluid temperature meter
14: flow rate/fluid temperature meter
15: flow switching valve
16: pump
17: fluid extraction opening
21: filtration device
21a: fluid input portion
21b: fluid output portion
100: organic processing fluid manufacturing system
F1: first stage filter
F2: second stage filter
H1: first filter housing
H2: second filter housing
D1, D2, D3: drain

What is claimed is:

1. A method for manufacturing an organic processing fluid for patterning of a chemical amplification type resist film, the method comprising:
    a step of causing a fluid containing an organic solvent to pass through a filtration device having a fluid input portion, a fluid output portion, and a series of filtration filter films provided in a flow path that connects the fluid input portion and the fluid output portion with each other, the filtration filter films being mounted with a heat insulation equipment respectively,
    wherein an absolute value ($|T_I-T_o|$) of a difference between a temperature ($T_I$) of the fluid in a fluid input portion of a first filtration filter film of the series of filtration filter films and a temperature ($T_o$) of the fluid in a fluid output portion of a last filtration filter film of the series of filtration filter films is 3° C. or lower,
    a filtration speed of the fluid in the filtration device is 0.5 L/min/m$^2$ or greater, and
    a filtration pressure by the fluid in the filtration device is 0.10 MPa or lower.

2. The method for manufacturing an organic processing fluid for patterning of a chemical amplification type resist film according to claim 1,
    wherein the organic processing fluid is an organic developer.

3. The method for manufacturing an organic processing fluid for patterning of a chemical amplification type resist film according to claim 2,
    wherein the fluid containing the organic solvent is butyl acetate.

4. A pattern forming method, comprising:
    (A) a step of forming a film with a chemical amplification type resist composition;
    (B) a step of exposing the film; and
    (C) a step of developing the exposed film by using an organic developer,
    wherein the organic developer is an organic developer manufactured by the method for manufacturing an organic processing fluid for patterning of a chemical amplification type resist film according to claim 2.

5. The pattern forming method according to claim 4, further comprising:
    a step of washing the exposed film by using an organic rinse fluid after the step of developing the exposed film by using the organic developer,
    wherein the organic rinse fluid is an organic rinse fluid manufactured by a method for manufacturing an organic processing fluid for patterning of a chemical amplification type resist film, the method comprising:
    a step of causing a fluid containing an organic solvent to pass through a filtration device having a fluid input portion, a fluid output portion, and a series of filtration filter films provided in a flow path that connects the fluid input portion and the fluid output portion with each other, the filtration filter films being mounted with a heat insulation equipment respectively,
    wherein an absolute value ($|T_I-T_o|$) of a difference between a temperature ($T_I$) of the fluid in a fluid input portion of a first filtration filter film of the series of filtration filter films and a temperature ($T_o$) of the fluid in a fluid output portion of a last filtration filter film of the series of filtration filter films is 3° C. or lower,
    a filtration speed of the fluid in the filtration device is 0.5 L/min/m$^2$ or greater, and
    a filtration pressure by the fluid in the filtration device is 0.10 MPa or lower,
    wherein the organic processing fluid is an organic rinse fluid.

6. The pattern forming method according to claim 5,
    wherein the organic developer is an organic developer manufactured by a method for manufacturing an organic processing fluid for patterning of a chemical amplification type resist film, the method comprising:

a step of causing a fluid containing an organic solvent to pass through a filtration device having a fluid input portion, a fluid output portion, and a series of filtration filter films provided in a flow path that connects the fluid input portion and the fluid output portion with each other, the filtration filter films being mounted with a heat insulation equipment respectively, wherein an absolute value ($|T_f-T_o|$) of a difference between a temperature ($T_f$) of the fluid in a fluid input portion of a first filtration filter film of the series of filtration filter films and a temperature ($T_o$) of the fluid in a fluid output portion of a last filtration filter film of the series of filtration filter films is 3° C. or lower, a filtration speed of the fluid in the filtration device is 0.5 L/min/m² or greater, and a filtration pressure by the fluid in the filtration device is 0.10 MPa or lower, wherein the organic processing fluid is an organic developer, the fluid containing the organic solvent is butyl acetate, wherein the organic rinse fluid is an organic rinse fluid manufactured by a method for manufacturing an organic processing fluid for patterning of a chemical amplification type resist film, the method comprising:

a step of causing a fluid containing an organic solvent to pass through a filtration device having a fluid input portion, a fluid output portion, and a series of filtration filter films provided in a flow path that connects the fluid input portion and the fluid output portion with each other, the filtration filter films being mounted with a heat insulation equipment respectively, wherein an absolute value ($|T_f-T_o|$) of a difference between a temperature ($T_f$) of the fluid in a fluid input portion of a first filtration filter film of the series of filtration filter films and a temperature ($T_o$) of the fluid in a fluid output portion of a last filtration filter film of the series of filtration filter films is 3° C. or lower, a filtration speed of the fluid in the filtration device is 0.5 L/min/m² or greater, and a filtration pressure by the fluid in the filtration device is 0.10 MPa or lower, wherein the organic processing fluid is an organic rinse fluid, the fluid containing the organic solvent is 4-methyl-2-pentanol or butyl acetate.

7. The pattern forming method according to claim 4, wherein the step of developing the film by using the organic developer is a step of developing a film by using a developing device with a filter for the processing fluid, and the organic developer is used for development by being passed through the filter for the processing fluid.

8. A method for manufacturing an electronic device, comprising:

the pattern forming method according to claim 4.

9. An electronic device manufactured by the method for manufacturing an electronic device according to claim 8.

10. The method for manufacturing an organic processing fluid for patterning of a chemical amplification type resist film according to claim 1, wherein the organic processing fluid is an organic rinse fluid.

11. The method for manufacturing an organic processing fluid for patterning of a chemical amplification type resist film according to claim 10, wherein the fluid containing the organic solvent is 4-methyl-2-pentanol or butyl acetate.

12. The method for manufacturing an organic processing fluid for patterning of a chemical amplification type resist film according to claim 1, wherein the filtration filter films are polyethylene resin films, fluorine resin films, or polyimide resin films, of which a pore size is 50 nm or lower.

13. The method for manufacturing an organic processing fluid for patterning of a chemical amplification type resist film according to claim 1, wherein the temperature ($T_f$) of the fluid in the fluid input portion is in a range of 20° C. to 30° C.

14. An organic processing fluid for patterning of a chemical amplification type resist film, which is manufactured by the method for manufacturing an organic processing fluid for patterning of a chemical amplification type resist film according to claim 1.

15. The method for manufacturing an organic processing fluid for patterning of a chemical amplification type resist film according to claim 1, wherein the filtration filter films are made of fluorine resin.

16. The method for manufacturing an organic processing fluid for patterning of a chemical amplification type resist film according to claim 1, wherein the organic solvent is selected from the group consisting of a ketone-based solvent, an ester-based solvent, and an alcohol-based solvent.

17. The method for manufacturing an organic processing fluid for patterning of a chemical amplification type resist film according to claim 1, wherein the series of filtration filter films are two or three filtration filter films used in series.

18. The method for manufacturing an organic processing fluid for patterning of a chemical amplification type resist film according to claim 1, wherein the heat insulation equipment is a heater or a water jacket.

19. The method for manufacturing an organic processing fluid for patterning of a chemical amplification type resist film according to claim 1, wherein the filtration filter films are provided in filter housings respectively, and the filter housings are set to the same temperature.

* * * * *